US007943323B2

(12) United States Patent
Cantor et al.

(10) Patent No.: US 7,943,323 B2
(45) Date of Patent: May 17, 2011

(54) METHODS FOR DIFFERENTIATING AND MONITORING PARATHYROID AND BONE STATUS RELATED DISEASES

(75) Inventors: Thomas L. Cantor, El Cajon, CA (US); Ping Gao, San Diego, CA (US)

(73) Assignee: Scantibodies Laboratory, Inc., Santee, CA (US)

( * ) Notice: Subject to any disclaimer, the term of this patent is extended or adjusted under 35 U.S.C. 154(b) by 2272 days.

(21) Appl. No.: 10/641,780

(22) Filed: Aug. 15, 2003

(65) Prior Publication Data

US 2004/0185536 A1 Sep. 23, 2004

Related U.S. Application Data

(63) Continuation of application No. 09/344,639, filed on Jun. 26, 1999, now Pat. No. 6,743,590, which is a continuation-in-part of application No. 09/231,422, filed on Jan. 14, 1999, now Pat. No. 6,689,566.

(51) Int. Cl.
G01N 33/53 (2006.01)
(52) U.S. Cl. .......................................... 435/7.1; 435/7.2
(58) Field of Classification Search .................. 435/7.1, 435/7.2, 331; 530/388.1, 388.15, 388.24
See application file for complete search history.

(56) References Cited

U.S. PATENT DOCUMENTS

| | | |
|---|---|---|
| 4,086,196 A | 4/1978 | Tregear |
| 4,208,479 A | 6/1980 | Zuk et al. |
| 4,369,138 A | 1/1983 | Lindall ................. 260/112.5 |
| 4,423,037 A | 12/1983 | Rosenblatt et al. .......... 424/177 |
| 4,508,828 A | 4/1985 | Lindall et al. ................ 436/500 |
| 4,517,290 A | 5/1985 | Iwasa et al. |
| 4,656,250 A | 4/1987 | Morita et al. ................. 530/324 |
| 4,751,284 A | 6/1988 | Forssmann |
| 4,782,044 A | 11/1988 | Forssmann |
| 4,824,777 A | 4/1989 | Chang et al. |
| 4,851,356 A | 7/1989 | Canfield et al. |
| 4,895,932 A | 1/1990 | Forssmann |
| 4,968,669 A | 11/1990 | Rosenblatt et al. |
| 5,026,653 A | 6/1991 | Lee et al. |
| 5,075,218 A | 12/1991 | Jette et al. |
| 5,093,233 A | 3/1992 | Rosenblatt et al. |
| 5,116,952 A | 5/1992 | Martin et al. |
| 5,208,041 A | 5/1993 | Sindrey |
| 5,256,543 A | 10/1993 | Pouletty et al. |
| 5,317,010 A | 5/1994 | Pang et al. |
| 5,354,900 A | 10/1994 | Matsuo et al. |
| 5,382,658 A | 1/1995 | Kronis et al. |
| 5,434,246 A | 7/1995 | Fukuda et al. |
| 5,496,801 A | 3/1996 | Holthuis et al. |
| 5,545,553 A | 8/1996 | Gotschlich |
| 5,589,452 A | 12/1996 | Krstenansky et al. |
| 5,639,617 A | 6/1997 | Bohuon |
| 5,656,455 A | 8/1997 | Wood et al. |
| 5,695,955 A | 12/1997 | Krstenansky et al. |
| 5,723,577 A | 3/1998 | Dong |
| 5,744,444 A | 4/1998 | Forssmann |
| 5,747,456 A | 5/1998 | Chorev et al. |
| 5,783,558 A | 7/1998 | Duvos et al. |
| 5,792,455 A | 8/1998 | Chapman et al. |
| 5,798,225 A | 8/1998 | Krstenansky et al. |
| 5,807,823 A | 9/1998 | Krstenansky et al. |
| 5,840,831 A | 11/1998 | Hamachi et al. |
| 5,955,264 A | 9/1999 | Seed et al. |
| 5,958,384 A | 9/1999 | Holick et al. |
| 6,030,790 A | 2/2000 | Adermann et al. ............ 435/7.1 |
| 6,124,314 A | 9/2000 | Cameron et al. |
| 6,387,711 B1 | 5/2002 | Sundaram et al. |
| 6,524,788 B1 | 2/2003 | Cantor ............................. 435/4 |
| 6,548,066 B1 | 4/2003 | Michaeli et al. |
| 6,689,566 B1 | 2/2004 | Cantor et al. |
| 6,743,590 B1 | 6/2004 | Cantor |
| 6,756,480 B2 | 6/2004 | Kostenuik et al. |
| 6,838,264 B2 | 1/2005 | Zahradnik et al. |
| 7,056,655 B2 | 6/2006 | Cantor |
| 7,057,012 B1 | 6/2006 | Gardella et al. |
| 7,459,276 B2 | 12/2008 | Cantor et al. |
| 7,465,703 B1 | 12/2008 | Cantor |
| 7,723,042 B2 | 5/2010 | Cantor et al. |
| 2002/0025929 A1 | 2/2002 | Sato |
| 2002/0110871 A1 | 8/2002 | Zahradnik et al. |
| 2002/0160945 A1 | 10/2002 | Cantor ........................... 514/12 |
| 2003/0082179 A1 | 5/2003 | Hutchison |

(Continued)

FOREIGN PATENT DOCUMENTS

DE 33 47 548 7/1985

(Continued)

OTHER PUBLICATIONS

Segre et al., "Development and application of sequence-specific radioimmunoassays for analysis of the metabolism of parathyroid hormone." Methods Enzymol. 37(Pt. B):38-66 (1975).
U.S. Appl. No. 60/224,396, filed Aug. 10, 2000, Cantor.
U.S. Appl. No. 09/323,606, filed Jun. 2, 1999, Cantor.
U.S. Appl. No. 09/636,530, filed Aug. 10, 2001, Cantor.
U.S. Appl. No. 09/636,531, filed Aug. 10, 2000, Cantor.
Adermann et al., in: Innovations and Perspectives in Solid Phase Synthesis, Epton (ed.), Mayflower World Wide, Birmingham (1994) pp. 429-432.
Atkinson et al., Journal of Immunoassay (1982) 3(1):31-51.
Blind et al., Clin. Chem. (1987) 33(8):1376-1381.
Bouillon; R. et al. (1990) Clin Chem 36(2):271-276.
Bowie et al., Science (1990) 247:1306-1310.

(Continued)

*Primary Examiner* — Jacob Cheu
(74) *Attorney, Agent, or Firm* — Morrison & Foerster LLP

(57) ABSTRACT

The present invention relates to novel methods and devices for differentiating in a patient parathyroid diseases, such as hyperparathyroidism and related bone diseases, from normal or non-disease states. One detects whole or non-fragmented (1 to 84) parathyroid hormone in a biological sample and also a large non-whole parathyroid hormone peptide fragment that can function as a parathyroid hormone antagonist. By either comparing values or using independently the value of either the large non-whole parathyroid hormone peptide fragment, the whole parathyroid hormone, or the combination of these values one is able to differentiate parathyroid and bone related disease states, as well as differentiate such states from normal states.

19 Claims, 12 Drawing Sheets

U.S. PATENT DOCUMENTS

| | | | |
|---|---|---|---|
| 2003/0087822 A1 | 5/2003 | Cantor | |
| 2003/0138858 A1 | 7/2003 | Cantor | 435/7.9 |
| 2003/0157560 A1 | 8/2003 | Cantor | |
| 2003/0171288 A1 | 9/2003 | Stewart | |
| 2003/0175802 A1 | 9/2003 | Armbruster et al. | |
| 2004/0014095 A1 | 1/2004 | Gerber et al. | |
| 2004/0067526 A1 | 4/2004 | Cantor | |
| 2004/0185536 A1 | 9/2004 | Cantor | |
| 2004/0219598 A1 | 11/2004 | Cantor | |
| 2004/0229281 A1 | 11/2004 | Cantor | |
| 2005/0003493 A1 | 1/2005 | Hutchison | |
| 2005/0026839 A1 | 2/2005 | Gardella | |
| 2005/0069952 A1 | 3/2005 | Cantor et al. | |
| 2005/0095236 A1 | 5/2005 | Zahradnik et al. | |
| 2005/0095631 A1 | 5/2005 | Cantor | |
| 2005/0170443 A1 | 8/2005 | Cantor | |
| 2005/0202506 A1 | 9/2005 | Cantor | |
| 2005/0260191 A1 | 11/2005 | Zahradnik et al. | |
| 2006/0024772 A1 | 2/2006 | Hutchison | |
| 2006/0035282 A1 | 2/2006 | Cantor | |
| 2006/0223119 A1 | 10/2006 | Cantor | |
| 2006/0286107 A1 | 12/2006 | Hutchison | |
| 2007/0098726 A1 | 5/2007 | Cantor et al. | |
| 2007/0287668 A1 | 12/2007 | Cantor et al. | |
| 2008/0069828 A1 | 3/2008 | Cantor et al. | |
| 2008/0108086 A1 | 5/2008 | Cantor | |
| 2009/0047686 A1 | 2/2009 | Cantor | |
| 2009/0094704 A1 | 4/2009 | Zahradnik et al. | |

FOREIGN PATENT DOCUMENTS

| | | |
|---|---|---|
| DE | 44 34 551 | 4/1996 |
| DE | 10 236 631 | 7/2003 |
| EP | 0 783 522 | 12/2001 |
| EP | 1 151 307 | 2/2007 |
| JP | 4132677 | 6/2008 |
| WO | WO 91/06564 | 5/1991 |
| WO | WO 93/06845 | 4/1993 |
| WO | WO 94/03201 | 2/1994 |
| WO | WO 96/10041 | 4/1996 |
| WO | WO-00/42437 | 7/2000 |
| WO | WO-01/44818 | 6/2001 |
| WO | WO-03/039572 | 5/2003 |
| WO | WO-2004/011607 | 2/2004 |
| WO | WO-2004/028444 | 4/2004 |
| WO | WO-2004/031727 | 4/2004 |
| WO | WO-2005/018413 | 3/2005 |

OTHER PUBLICATIONS

Brossard et al., Journal of Clinical Endocrinology and Metabolism (1996) 81(11):3923-3929.
Campbell, Monoclonal Antibody and Immunosensor Technology, in Laboratory Techniques in Biochemistry and Molecular Biology, van der Vliet (ed.), Elsevier (1991) pp. 1-11, 42-45.
Caporale and Rosenblatt, Paraththyroid Hormone Antagonists Effective in vivo, in: Advances in Experimental Medicine and Biology, New York (1986)pp. 315-327.
Cardinal, H. et al. (1998) J of Clinical Endocrinology & Metabolism 83(11):3839-3844.
Clinical Chemistry (1999) 45(6)Suppl:A97 b, Abstract Nos. 339-341.
Cohen Solal, M.-E., et al. (1991) J of Clinical Endocrinology & Metabolism 73(3):516-524.
D'Amour et al., Am. J. Physiol. (1986) 251:E680-E687.
D'Amour, P. et al. (1992) J of Clinical Endocrinology & Metabolism 74(3):525-532.
Daniel et al., Virology (1994) 202:540-549.
Fischer et al., The Journal of Clinical Investigation (1974) 54:1382-1394.
Fournier, A. et al. (2001) J of Clinical Endocrinology & Metabolism 86(4):1840-1841.
Fournier, A. et al. (2002) Kidney Int 61(3):1181.
Gao et al., Clinica Chimica Acta (1996) 245:39-59.
Goodman, W.G., et al. (2001) J of Clinical Endocrinology & Metabolism 86(4):1841-1842.
Gordon et al., Parathyroid Hormone Domain for Protein Kinase C Stimulation Located within Amphiphilic Helix, in: Peptides: Chemistry and Biology, Proceedings of the Twelfth American Peptide Symposium, Jun. 16-21, 1991, Cambridge, MA, Smith and Rivier (eds.) Escom Science Publishers (1992) pp. 37-39.
Hashimoto et al., Journal of Cardiovascular Pharmacology (1981) 3(4):668-676.
Hehrmann et al., Journal of Immunoassay (1980) 1(2):151-174.
John et al., Journal of Clinical Endocrinology and Metabolism (1999) 84(11):4287-4290.
LePage et al., Clin. Chem. (1998) 44:805-810.
Logue et al., Journal of Immunological Methods (1991) 137:159-166.
Mägerlein et al., Arzneim.-Forsch./Drug Res. (1998) 48(I):197-204.
Mägerlein et al., Arzneim.-Forsch./Drug Res. (1998) 48(II):783-787.
Mallette, Journal of Clinical Endocrinology and Metabolism (1980) 50(1):201-203.
Nakamura et al., Endocrinol. JPN (1981) 28(4):547-549.
Ngo et al., The Protein Folding Problem and Tertiary Structure Prediction, Merz et al., (eds.), Birkhäuser Boston (1994) pp. 492-495.
Niall et al., Proc. Natl. Acad. Sci. USA (1974) 71(2):384-388.
Nussbaum et al., Chemical Abstracts (1982) 96(5):181-192.
Pang et al., Pharmacol. Exp. Ther. (1981) 216(3):567-571.
Qi et al., Am. J. Kidney Dis. (1995) 26:622-631.
Quarles et al., J. Clin. Endocrinol. Metab. (1992) 75:145-150.
Stadler, Homologous Radioimmunoassay for Human Parathyroid Hormone (Residues 1-34) with Biotinylated Peptide as Tracer, in Calcium Regulating Hormones, Vitamin D Metabolites, and Cyclic AMP Assays and their Clinical Application, Schmidt-Gayk et al., (eds.), Berlin/Heidelberg, Springer, (1990) pp. 137-150.
Tampe et al., J. Immunoassay (1992) 13(1):1-13.
Visser et al., Acta Endocrinology (1979) 90:90-102.
Wingender et al., Structure-Function Relationship in Parathyroid Hormone in: Advances in Protein Design, International Workshop, Blöcker et al. (eds.), VCH (1988) pp. 167-176.
Zanelli et al., Journal of Immunoassay (1983) 4(2):175-206.
Allegro Intact PTH, directional insert for PTH kit by Nichols Institute.
Cantor, Kidney Int. (2004) 66:461.
Coen et al., J. Lab. Clin. Med. (1993) 122:103-109.
D'Amour et al., Clin. Chem. (2003) 49:2037-2044.
D'Amour et al., Clin. Chem. (2005) 51:169-176.
Estepa et al., Equine Vet J. (2003) 35:291-295.
Estepa et al., Nephrol. Dial. Transplant. (2003) 18:1101-1107.
Fine and Zacharias, Kidney Int. (2002) 61:2210-2217.
Fournier et al., Nephrol. Dial. Transplant. (1999) 14:2772-2774.
Gao et al., J. Bone Mineral Res. (2001) 16:605-614.
Gao et al., "Recognition of the PTH(7-84) Fragment by 5 Commercial PTH 'Sandwich' Assays" presented at the ASMBR 22$^{nd}$ Annual Meeting, Sep. 22-26, 2000, Toronto, Canada.
Goltzman et al., J. Clin. Invest. (1980) 65:1309-1317.
Goodman et al., Nephrol. Dial. Transplant. (2002) 17:1731-1736.
Harlow and Lane, Antibodies: A Laboratory Manual, Cold Spring (1988) pp. 313-315.
Kazama et al., Nephrol. Dial. Transplant. (2004) 19:892-897.
Kifor et al., J. Clin. Endocrinology Metab. (2003) 88:60-72.
Kifor et al., J. Clin. Endocrinology Metab. (2003) 88:4455-4464.
Kifor et al., J. Clin. Endocrinology Metab. (2004) 89:548-556.
Kohno et al., J. Clin, Lab. Anal. (1998) 12:268-275.
Magerlein et al., European Journal of Pharmaceutical Sciences (1994) vol. 2 pt. ½ at 154.
Marx et al., Journal of Biological Chemistry (1995) 270:15194-15202.
Marx, Medical Progress (2000) 343:1863-1875.
Monier-Faugere et al., Kidney Int. (2001) 60:1460-1468.
Nichols Advantage Bio-Intact PTH (1-84), Directional Insert for the test kit.
Nguyen-Yamamoto et al., Eur. J. Endocrinol. (2002) 147:123-131.
Salomon et al., Pediatr. Nephrol. (2001) 16:1011-1014.
Sanchez and Salusky, Adv. Ren. Replace. Ther. (1996) 3:14-23 (Abstract only).
Santamaria et al., Kidney Int. (2003) 64:1867-1873.

Silverberg et al., J. Clin. Endocrinology Metab. (2003) 88:4725-4730.
Slatopolsky et al., Kidney Int. (2000) 58:753-761.
Souberbielle et al., J. Clin. Endocrinology Metab. (2001) 86:3086-3090.
Uddin et al., Clinical Chemistry (1999) 45:A97 (340).
Waller et al., "What is the parathyroid hormone level?" pamphlet.
Waller et al., Pediatr. Nephrol. (2003) 18:1242-1248.
Waller et al., Pediatr. Nephrol. (2005) 20:197-199.
Yamashita et al., Ann. Surg. (2002) 236:105-111.
Yamashita et al., Eur. J. Endocrinol. (2003) 149:301-306.
Yamashita et al., Surgery (2004) 135:149-156.
Opposition Documents against EP Patent No. 0 783 522, dated Sep. 4, 2002.
Opposition Documents against EP Patent No. 0 783 522, dated Sep. 5, 2002.
Opposition Documents against EP Patent No. 0 783 522, dated Dec. 10, 2003.
Official communication issued by the EPO on Jul. 8, 2004 in the opposition against EP Patent No. 0 783 522.
English translation of the official communication issued by the EPO on Jul. 8, 2004 in the opposition against EP Patent No. 0 783 522.
Summons to Oral Proceedings—Patent No. 95934629.7-2405/0783522—Ref. G1263 EP/OPP OPPO.01, mailed Mar. 18, 2005.
Certified English translation of Summons to Oral Proceedings—Patent No. 95934629.7-2405/0783522—Ref. G1263 EP/OPP OPPO.01, mailed Mar. 18, 2005.
Opposition Documents against JP Patent No. 3457004, Opposition No. 2003-73801, dated Dec. 29, 2003.
Opposition Documents against JP Patent No. 3457004, Opposition No. 2003-73801, dated Apr. 13, 2004.
Notification of Reasons for Revocation, dated Jul. 9, 2004.
Notification of Invalid Judgment of Patent 3457004 by Japanese Patent Office, Mar. 2005.
English translation of Notification of Invalid Judgment of Patent 3457004 by Japanese Patent Office, Mar. 2005.
Request for Reexamination Under 37 C.F.R. § 1.510 for US Patent No. 6,030,790, filed Feb. 4, 2005.
Ex Parte Reexamination Communication Transmittal Form for US Patent No. 6,030,790, and Order Granting Reexamination, mailed Mar. 30, 2005.
Complaint for Patent Infringement, *Nichols Institute Diagnostics, Inc. v. Scantibodies Clinical Laboratory, Inc. and Scantibodies Laboratory, Inc.*, filed Jan. 8, 2002 in the United States District Court for the Southern District of California, Case No. 02 CV 0046 B (LAB).
Answer and Counterclaims of Defendants Scantibodies Clinical Laboratory, Inc. and Scantibodies Laboratory, Inc., filed May 9, 2002.
Notice of Motion and Motion for Summary Judgment Pursuant to 35 U.S.C. § 102(f) for Nonjoinder of Co-Inventor, filed on May 16, 2002.
Scantibodies Clinical Laboratory, Inc. and Scantibodies Laboratory, Inc.'s Memorandum of Points and Authorities in Support of Motion for Summary Judgment Pursuant to 35 U.S.C. § 102(f) for NonJoinder of Co-Inventor, filed May 16, 2002.
Declaration of M. Andrew Woodmansee in Support of Scantibodies Clinical Laboratory, Inc. and Scantibodies Laboratory Inc.'s Motion for Summary Judgment Pursuant to 35 U.S.C. § 102(f) for NonJoinder of Co-Inventor, filed May 16, 2002.
Plaintiff/Counterdefendant Nichols Institute Diagnostics, Inc.'s Reply to Defendants' Counterclaims, filed May 29, 2002.
Defendant Scantibodies Clinical Laboratory's Initial Disclosure, filed Jul. 16, 2002 in 02 CV 0046 B (LAB).
Nichols Institute Diagnostics, Inc.'s Initial Disclosures Pursuant to Fed. R. Civ. P. 26(a)(1), filed on Jul. 16, 2002 in 02 CV 0046 B (LAB).
Plaintiff's Memorandum of Points and Authorities in Support of Opposition to Defendants' Motion for Summary Judgment Pursuant to 35 U.S.C. § 102(f) fo NonJoinder of Co-Inventor, filed Jul. 22, 2002.
Declaration of Vicki G. Norton in Support of Plaintiff's Opposition to Motion for Summary Judgment Pursuant to 35 U.S.C. § 102(f) for NonJoinder of Co-Inventor, filed Jul. 22, 2002.

Declaration of James T. Carmichael in Support of Plaintiff's Opposition to Motion for Summary Judgment Pursuant to 35 U.S.C. § 102(f) for NonJoinder of Co-Inventor, filed Jul. 22, 2002.
Scantibodies Clinical Laboratory, Inc. and Scantibodies Laboratory, Inc.'s Reply in Support of Motion for Summary Judgment Pursuant to 35 U.S.C. § 102(f) for NonJoinder of Co-Inventor, filed Jul. 29, 2002.
Declaration of David C. Doyle in Support of Scantibodies Clinical Laboratory, Inc. and Scantibodies Laboratory Inc.'s Reply in Support of Motion for Summary Judgment Pursuant to 35 U.S.C. § 102(f) for NonJoinder of Co-Inventor, filed Jul. 29, 2002.
Plaintiff's Sur-Reply in Opposition to Defendants' Reply to Plaintiff's Opposition to Motion for Summary Judgment Pursuant to 35 U.S.C. § 102(f) for NonJoinder of Co-Inventor, filed Aug. 16, 2002.
Declaration of Vicki G. Norton in Support of Plaintiff's Sur-Reply in Opposition to Defendants' Reply to Opposition to Motion for Summary Judgment Pursuant to 35 U.S.C. § 102(f) for NonJoinder of Co-Inventor, filed Aug. 16, 2002.
Scantibodies Clinical Laboratory, Inc. and Scantibodies Laboratory, Inc.'s Response to Plaintiff's Sur-Reply, filed Aug. 20, 2002.
Declaration of David C. Doyle in Support of Scantibodies Clinical Laboratory, Inc. and Scantibodies Laboratory Inc.'s Response to Plaintiff's Sur-Reply, filed Aug. 20, 2002.
Order Denying as Moot Defendants' Motion for Summary Judgment Pursuant to 35 U.S.C. § 102(f) for NonJoinder of Co-Inventor, Denying Request for Stay, and Ordering Plaintiff to File Amended Complaint, issued Sep. 6, 2002.
Amended Complaint for Patent Infringement, Case No. 02-CV-0046 B (LAB), filed Sep. 20, 2002.
Scantibodies Clinical Laboratory, Inc. and Scantibodies Laboratory, Inc.'s Notice of Appeal, filed Oct. 4, 2002.
Notice of Document Discrepancies rejecting the original Answer and Counterclaims filed by Scantibodies on May 9, 2002, notice dated Oct. 15, 2002.
Answer and Counterclaims of Defendants Scantibodies Clinical Laboratory, Inc. and Scantibodies Laboratory Inc. to Nichols' Amended Complaint for Patent Infringement, filed Oct. 17, 2002.
Plaintiff/Counterdefendant Nichols Institute Diagnostics, Inc.'s Reply to Defendants' Counterclaims, filed Nov. 4, 2002.
Plaintiffs' Brief on Claim Construction for the '790 Patent, filed Nov. 12, 2002.
Declaration of Vicki G. Norton in Support of Plaintiffs' Brief on Claim Construction for the '790 Patent, filed Nov. 12, 2002.
Scantibodies Clinical Laboratory, Inc. and Scantibodies Laboratory, Inc.'s Claim Construction Brief for U.S. Patent No. 6,030,790, filed Nov. 12, 2002.
Declaration of M. Andrew Woodmansee in Support of Scantibodies Clinical Laboratory, Inc. and Scantibodies Laboratory Inc.'s Claim Construction Brief for U.S. Patent No. 6,030,790, filed Nov. 12, 2002.
Declaration of Dr. Richard A. Lerner in Support of Scantibodies Clinical Laboratory, Inc. and Scantibodies Laboratory Inc.'s Claim Construction Brief for U.S. Patent No. 6,030,790, filed Nov. 12, 2002.
Declaration of Thomas G. Wiseman in Support of Scantibodies Clinical Laboratory, Inc. and Scantibodies Laboratory Inc.'s Claim Construction Brief for U.S. Patent No. 6,030,790, filed Nov. 12, 2002.
Nichols Institute Diagnostics, Inc.'s Supplemental Brief in Support of Motion for Judgment on the Pleadings, filed Dec. 2, 2002.
Reply of Scantibodies Clinical Laboratory, Inc. and Scantibodies Laboratory, Inc. in Support of Motion for Reconsideration of Dismissal for Want of Jurisdiction, filed Dec. 3, 2002.
Notice of Document Discrepancies, filed Dec. 5, 2002.
Report and Recommendation, filed Dec. 31, 2002 in United States District Court for the Southern District of Florida, Miami Division.
ESRD'S Verified Motion to Tax Costs as Prevailing Party, filed Jan. 3, 2003 in United States District Court for the Southern District of Florida, Miami Division.
Plaintiff's Supplemental Brief on Claim Construction for the '790 Patent, filed Jan. 8, 2003.
Declaration of Vicki G. Norton in Support of Plaintiff's Supplemental Brief on Claim Construction for the '790 Patent, filed Jan. 8, 2003.

Declaration of Joseph O. Falkinham III, Ph.D. in Support of Plaintiffs' Supplemental Brief on Claim Construction for the '790 Patent, filed Jan. 8, 2003.
[Proposed] Order Granting Nichols Institute Diagnostics Inc.'s Ex Parte Application for Order Allowing Exhibit 9 to Plaintiff's Supplemental Brief on Claim Construction for the '790 Patent to be Filed Under Seal, filed Jan. 8, 2003.
Scantibodies Clinical Laboratory, Inc. and Scantibodies Laboratory Inc.'s Supplemental Brief in Advance of Claim Construction Hearing on U.S. Patent No. 6,030,790, filed Jan. 8, 2003.
Declaration of M. Andrew Woodmansee in Support of Scantibodies Clinical Laboratory, Inc. and Scantibodies Laboratory, Inc.'s Supplemental Claim Construction Brief for U.S. Patent No. 6,030,790, filed Jan. 8, 2003.
Parties Joint Claim Construction Chart, filed Jan. 8, 2003.
Notice of Document Discrepancies, filed Jan. 10, 2003.
Scantibodies Clinical Laboratory Inc. and Scantibodies Laboratory Inc.'s Brief in Advance of Jan. 30, 2003 Hearing on the Terms "Suitable Carrier" and "Peptide" for U.S. Patent No. 6,030,790, filed Jan. 22, 2003.
Declaration of M. Andrew Woodmansee in Support of Scantibodies Clinical Laboratory, Inc. and Scantibodies Laboratory, Inc.'s Brief in Advance of Jan. 30, 2003 Hearing on the Terms "Suitable Carrier" and "Peptide" for the U.S. Patent No. 6,030,790, filed Jan. 22, 2003.
Plaintiff Nichols Institute Diagnostics, Inc.'s Second Supplemental Claim Construction Brief, filed Jan. 22, 2003.
Declaration of Vicki G. Norton in Support of Plaintiff's Second Supplemental Brief on Claim Construction for the '790 Patent, filed Jan. 22, 2003.
Declaration of Dr. Leonard J. Deftos in Support of Plaintiff Nichols Institute Diagnostics, Inc.'s Second Supplemental Claim Construction Brief, filed Jan. 22, 2003.
Notice of Motion and Motion for Summary Judgment Pursuant to 35 U.S.C. § 102(b), filed Feb. 25, 2003.
Memorandum of Points and Authorities in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Statement of Undisputed Material Facts in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Declaration of Richard A. Lerner, M.D., in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Declaration of J. Stuart Woodhead, Ph.D., in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Declaration of Andrew William Smith in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Declaration of Kimberly L. Briggs in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Declaration of Hans H. Linden in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Order Construing Patent Claims and Terms for Jury Trial, filed Mar. 10, 2003.
Scantibodies Clinical Laboratory, Inc. and Scantibodies Laboratory, Inc.'s Notice of Motion and Motion for Reconsideration of Court's Mar. 10, 2003 Order Construing Patent Claims and Terms for Jury Trial, filed Mar. 24, 2003.
Scantibodies Clinical Laboratory, Inc. and Scantibodies Laboratory, Inc.'s Motion for Reconsideration of Court's Mar. 10, 2003 Order Construing Patent Claims and Terms for Jury Trial, filed Mar. 24, 2003.

Declaration of M. Andrew Woodmansee in Support of Scantibodies Clinical Laboratory, Inc. and Scantibodies Laboratory, Inc.'s Motion for Reconsideration of Court's Mar. 10, 2003 Order Construing Patent Claims and Terms for Jury Trial, filed Mar. 24, 2003.
Re-Notice of Motion and Motion for Summary Judgment Pursuant to 35 U.S.C. § 102(b), or in the Alternative, 35 U.S.C. § 103(a), filed Apr. 2, 2003.
Scantibodies Clinical Laboratory, Inc. and Scantibodies Laboratory, Inc.'s Supplemental Memorandum of Points and Authorities in Support of Motion for Summary Judgment Pursuant to 35 U.S.C. § 102(b), or in the Alternative, 35 U.S.C. § 102(a), filed Apr. 2, 2003.
Nichols Institute Diagnostics, Inc. Opposition to Defendants' Motion for Reconsideration of the Court's Mar. 10, 2003 Order Construing Patent Claims and Terms for Jury Trial, filed Apr. 8, 2003.
Declaration of Julia A. Miller in Support of Nichols Institute Diagnostics, Inc. Opposition to Defendants' Motion for Reconsideration of the Court's Mar. 10, 2003 Order Construing Patent Claims and for Jury Trial, filed Apr. 8, 2003.
Declaration of Dr. Leonard J. Deftos in Support of Nichols Institute Diagnostics, Inc. Opposition to Defendants' Motion for Reconsideration of Court's Mar. 10, 2003 Order Construing Patent Claims and Terms for Jury Trial, filed Apr. 8, 2003.
Scantibodies Clinical Laboratory, Inc. and Scantibodies Laboratory, Inc.'s Reply to Opposition to Motion for Reconsideration of Court's Mar. 10, 2003 Order Construing Patent Claims and Terms for Jury Trial, filed Apr. 14, 2003.
Order Granting Motion for Reconsideration and Confirming Original Order Construing Patent Claims Filed Mar. 10, 2003, filed Apr. 29, 2003.
Nichols Institute Diagnostics, Inc.'s Opposition to Motion for Summary Judgment Pursuant to 35 U.S.C. § 102(b) or in the Alternative 35 U.S.C. § 103(a) by Defendants Scantibodies Clinical Laboratory, Inc. and Scantibodies Laboratory, Inc., filed May 7, 2003.
Declaration of Julia a. Miller in Support of Nichols Institute Diagnostics, Inc.'s Opposition to Motion for Summary Judgment Pursuant to 35 U.S.C. § 102(b) or in the Alternative 35 U.S.C. § 103(a) by Defendants Scantibodies Clinical Laboratory, Inc. and Scantibodies Laboratory, Inc, filed May 7, 2003.
Declaration of Leonard J. Deftos in Support of Nichols Institute Diagnostics' Opposition to Motion for Summary Judgment Pursuant to 35 U.S.C. § 102(b), or in the Alternative, 35 U.S.C. § 103(a), filed May 7, 2003.
Declaration of Douglas E. Olson in Support of Nichols' Application Under Federal Rule of Civil Procedure 56(f), filed May 7, 2003.
Declaration of Peter R. Munson in Support of Nichols Institute Diagnostics, Inc.'s Opposition to Motion for Summary Judgment Pursuant to 35 U.S.C. § 102(b) or in the Alternative 35 U.S.C. § 103(a) by Defendants Scantibodies Clinical Laboratory, Inc. and Scantibodies Laboratory, Inc., filed May 8, 2003.
Nichols Institute Diagnostics, Inc.'s Response to Defendants' Statement of Undisputed Material Facts in Support of Motion for Summary Judgment Pursuant to 35 U.S.C. § 102(b) or Alternatively Under 35 U.S.C. § 103(a), filed May 8, 2003.
Nichols Institute Diagnostics, Inc.'s Notice of Motion and Motion to Strike the Briggs, Linden, and Smith Declarations Submitted by Defendants in Support of Motion for Summary Judgment, filed May 8, 2003.
Nichols Institute Diagnostics, Inc.'s Memorandum in Support of Motion to Strike the Briggs, Linden, and Smith Declarations Submitted by Defendants in Support of Motion for Summary Judgment, filed May 8, 2003.
Scantibodies Clinical Laboratory, Inc. and Scantibodies Laboratory, Inc.'s Reply in Support of Motion for Summary Judgment Pursuant to 35 U.S.C. § 102(b), or in the Alternative, 35 U.S.C. § 102(a), filed May 14, 2003.
Reply Declaration of M. Andrew Woodmansee in Support of Motion for Summary Judgment Pursuant to 35 U.S.C. § 102(b), or in the Alternative 35 U.S.C. § 103(a), filed May 14, 2003.
Declaration of Paul Ayris in Support of Motion for Summary Judgment Pursuant to 35 U.S.C. § 102(b) by Defendants Scantibodies Clinical Laboratory, Inc. and Scantibodies Laboratory, Inc., filed May 14, 2003.

Declaration of Marianne Kranenborg in Support of Motion for Summary Judgment Pursuant to 35 U.S.C. § 102(b) by Defendants Scantibodies Clinical Laboratory, Inc. and Scantibodies Laboratory, Inc., filed May 14, 2003.

Declaration of Roderick Morrison in Support of Motion for Summary Judgment Pursuant to 35 U.S.C. § 102(b) by Defendants Scantibodies Clinical Laboratory, Inc. and Scantibodies Laboratory Inc, filed May 14, 2003.

Scantibodies Clinical Laboratory, Inc. and Scantibodies Laboratory, Inc.'s Opposition to Nichols' Motion to Strike Affidavits of Briggs, Linden, and Smith, filed May 14, 2003.

Scantibodies Clinical Laboratory, Inc's and Scantibodies Laboratory, Inc.'s Evidentiary Objections to Declaration of Julia Miller, filed May 14, 2003.

Nichols Institute Diagnostics, Inc.'s Notice of Motion and Motion to Strike the Kranenborg Declaration Submitted by Defendants in Support of Reply to Nichols' Opposition to Motion for Summary Judgment, filed May 16, 2003.

Nichols Institute Diagnostics, Inc.'s Memorandum in Support of Motion to Strike the Kranenborg Declaration Submitted by Defendants in Support of their Reply to Nichols' Opposition to Motion for Summary Judgment, filed May 16, 2003.

Nichols Institute Diagnostics, Inc.'s Errata Sheet Regarding Responses to Scantibodies' Undisputed Fact Nos. 6 and 41, filed May 20, 2003.

Scantibodies Clinical Laboratory, Inc. and Scantibodies Laboratory Inc.'s Objections to Nichols Institute Diagnostics, Inc's Errata Sheet Regarding Responses to Scantibodies' Undisputed Fact Nos. 6 and 41, filed May 21, 2003.

Order Denying Defendants' Motion for Summary Judgment and Granting Summary Adjudication, filed Jun. 2, 2003.

Scantibodies' Notice of Motion and Motion for Judgment on the Pleadings for Lack of Standing and Failure to Join an Indispensable Party or, in the Alternative, to Join a Necessary Party Pursuant to FRCP 19, filed Jul. 16, 2003.

Memorandum of Points and Authorities in Support of Scantibodies' Motion for Judgment on the Pleadings for Lack of Standing and Failure to Join an Indispensable Party or, in the Alternative, to Join a Necessary Party Pursuant to FRCP 19, filed Jul. 16, 2003.

Nichols Institute Diagnostics, Inc.'s Opposition to Scantibodies' Motion for Judgment on the Pleadings for Lack of Standing and Failure to Join an Indispensable Party or, in the Alternative, to Join a Necessary Party Pursuant to FRCP 19, filed Sep. 18, 2003.

Declaration of K. Ramakrishnan, filed Sep. 18, 2003.

Declaration of Randall Ringold, filed Sep. 18, 2003.

Declaration of Dr. Michael Harder, filed Sep. 18, 2003.

Reply in Support of Scantibodies' Motion for Judgment on the Pleadings for Lack of Standing and Failure to Join an Indispensable Party or, in the Alternative, to Join a Necessary Party Pursuant to FRCP 19, Sep. 24, 2003.

Declaration of Thomas Cantor in Support of Scantibodies' Motion for Judgment on the Pleadings for Lack of Standing and Failure to Join an Indispensable Party or, in the Alternative, to Join a Necessary Party Pursuant to FRCP 19, filed Sep. 24, 2003.

Nichols Institute Diagnostics, Inc.'s Notice of Motion and Motion to Permit Service of its Supplemental Amended Complaint Under F.R.C.P. 15(d), filed Nov. 24, 2003.

Memorandum of Points and Authorities in Support of Nichols Institute Diagnostics, Inc.'s Motion to Permit Service of its Supplemental Amended Complaint Under F.R.C.P. 15(d), filed Nov. 24, 2003.

Order Granting Defendants' Motion on the Pleadings and Dismissing Case with Leave to Amend, filed Dec. 1, 2003.

Nichols Institute Diagnostics, Inc.'s Notice of Motion and Motion for Leave to File Amended Complaint, filed Jan. 26, 2004.

Nichols Institute Diagnostics, Inc.'s Memorandum of Points and Authorities in Support of its Motion for Leave to File Amended Complaint, filed Jan. 26, 2004.

Nichols Institute Diagnostics, Inc's Notice of Application and Ex Parte Application for Order Sealing Exhibit 2 to its Second Amended Complaint, Exhibit A to the Declaration of Julia A. Miller in Support of Nichols Institute Diagnostics, Inc.'s Motion for Leave to File Amended Complaint, filed Jan. 26, 2004.

Declaration of Julia A. Miller in Support of Nichols' Ex Parte Application for Order Sealing Exhibit 2 to its Second Amended Complaint, Exhibit A to the Declaration of Julia A. Miller in Support of Nichols Institute Diagnostics, Inc.'s Motion for Leave to File Amended Complaint, filed Jan. 26, 2004.

Scantibodies' Notice of Motion and Motion for Judgment on the Pleadings for Lack of Standing and for Attorneys' Fees, filed Jan. 26, 2004.

Memorandum of Points and Authorities in Support of Scantibodies' Motion for Judgment on the Pleadings for Lack of Standing and for Attorneys' Fees, filed Jan. 26, 2004.

Scantibodies Laboratory, Inc., and Scantibodies Clinical Laboratory, Inc.'s Opposition to Nichols Institute Diagnostics, Inc.'s Motion to Amend Complaint, filed Feb. 9, 2004.

Nichols Institute Diagnostics, Inc.'s Reply to Scantibodies Laboratory, Inc. and Scantibodies Clinical Laboratory, Inc.'s Opposition to Motion for Leave to File Amended Complaint, filed Feb. 23, 2004.

Declaration of Julia A. Miller in Support of Nichols Institute Diagnostics, Inc.'s Reply to Scantibodies Laboratory, Inc. and Scantibodies Clinical Laboratory, Inc's Opposition to Motion for Leave to File Amended Complaint, filed Feb. 23, 2004.

Scantibodies' Reply to Nichols Institute Diagnostics, Inc.'s Opposition to Motion for Judgment on the Pleadings for Lack of Standing and for Attorneys' Fees, filed Feb. 23, 2004.

Order Granting Plaintiff's Motion for Leave to File a Supplemental Amended Complaint, filed Mar. 8, 2004.

Order Denying Defendant's Motion for Judgment on the Pleadings and Denying Defendant's Motion for Attorneys' Fees, filed Mar. 8, 2004.

Answer and Counterclaims of Defendants Scantibodies Clinical Laboratory, Inc. and Scantibodies Laboratory, Inc. to Nichols' Second Amended Complaint for Patent Infringement, filed Apr. 6, 2004.

Plaintiff/Counter-defendant Nichols Institute Diagnostics, Inc.'s Reply to Defendants' Counterclaim, filed Apr. 26, 2004.

Notice of Motion and Motion for Nichols Institute Diagnostics, Inc.'s Motion for Summary Judgment That the '790 Patent Claims are Valid and Infringed, filed Feb. 28, 2005.

Memorandum of Points and Authorities in Support of Nichols Institute Diagnostics, Inc.'s Motion for Summary Judgment that the '790 Patent Claims are Valid and Infringed, filed Feb. 28, 2005.

Declaration of John E. Peterson in Support of Nichols Institute Diagnostics, Inc.'s Motion for Summary Judgment that the '790 Patent Claims are Valid and Infringed, filed Feb. 28, 2005.

Declaration of Shelby J. Hall, Ph.D., in Support of Nichols Institute Diagnostics, Inc.'s Motion for Summary Judgment that the '790 Patent Claims are Valid and Infringed, filed Feb. 28, 2005.

Declaration of Joseph O. Falkinham III, Ph.D., in Support of Nichols Institute Diagnostics, Inc.'s Motion for Summary Judgment that the '790 Patent Claims are Valid and Infringed, filed Feb. 28, 2005.

Nichols Institute Diagnostics, Inc.'s Notice of and Ex Parte Application for Order to File Documents Under Seal with Motion for Summary Judgment, filed Feb. 28, 2005.

Declaration of April M. Alex in Support of Nichols' Ex Parte Application for Order to File Documents Under Seal with Motion for Summary Judgment, filed Feb. 28, 2005.

Notice of Decisions on Plaintiff's and Defendants' Cross Motions for Summary Judgment Regarding United States Patent No. 6,030,790 and Defendants' Motion to Stay the Trial and Defendants' Motion to Sequence Evidence of Liability and Damages at Trial, filed Mar. 30, 2005.

Scantibodies' Notice of Motion and Motion for Reconsideration of Order Denying Motion to Stay, or in the Alternative, Motion for Certification Under 28 U.S.C. § 1292(b), filed Apr. 1, 2005.

Memorandum of Points and Authorities in Support of Scantibodies' Motion for Reconsideration of Order Denying Motion to Stay, or in the Alternative, Motion for Certification Under 28 U.S.C. § 1292(b), filed Apr. 1, 2005.

Declaration of M. Andrew Woodmansee in Support of Scantibodies' Motion for Reconsideration of Order Denying Motion to Stay, or in the Alternative, Motion for Certification Under 28 U.S.C. § 1292(b), filed Apr. 1, 2005.

Expert Report of Michael R. Hamrell, Ph.D.

Defendants Scantibodies Clinical Laboratory, Inc., and Scantibodies Laboratory, Inc.'s Rebuttal Expert Witness Report by Steven Jones.
Rebuttal Expert Report of Richard A. Lerner, M.D.
Initial Expert Report of Randolph Wall, Ph.D.
Rebuttal Expert Report of Randolph Wall, Ph.D.
Expert Report of Thomas G. Wiseman, Esq.
Supplemental Expert Report of Thomas G. Wiseman, Esq.
Rebuttal Expert Report of Thomas G. Wiseman, Esq.
Expert Report of J. Stuart Woodhead Ph.D., FRCPath.
Supplemental Report of J. Stuart Woodhead Ph.D., FRCPath.
Rebuttal Expert Report of Claude Arnaud, M.D., FACE.
Rebuttal Expert Report of Gerald Bjorge.
Expert Report of Larry W. Evans Pursuant to Rule 26(A)(2)(B), Fed. R. Civ. P.
Expert Report of L.J. Deftos, MD, JD, LLM.
Complaint for Direct Patent Infringement, 35 U.S.C. § 271(a); and Inducing Patent Infringement, 35 U.S.C. § 271(b), filed Oct. 26, 2004 in *Scantibodies Laboratory, Inc.* v. *Immutopics, Inc.*, Case No. CV04-8871 GPS (MANx) United States District Court for the Central District of California.
Plaintiff Scantibodies Laboratory, Inc.'s Certificate of Interested Parties and Corporate Disclosure Statement (Fed. R. Civ. Proc. 7.1 and Central District Local Rule 7.1-1), filed Oct. 26, 2004.
Plaintiff Scantibodies Laboratory, Inc.'s Notice of Related Cases Pursuant to Central District Local Rule 83-1.3, filed Oct. 26, 2004.
Report on the Filing or Determination of an Action Regarding a Patent, Filed Oct. 26, 2004.
Defendants' Answer to Plaintiff's Complaint and Counterclaims, filed Dec. 3, 2004.
Certification and Notice of Interested Parties, filed Dec. 3, 2004.
Defendants' First Amended Answer to Plaintiff's Complaint and Counterclaims, filed Dec. 21, 2004.
Defendants' Second Amended Answer to Plaintiff's Complaint and Counterclaims, filed Dec. 31, 2004.
Plaintiff's Reply to Defendants' Counterclaims, filed Jan. 27, 2005.
Joint Report of Rule 26(f) Conference of Counsel, filed Feb. 7, 2005.
Civil Minutes—General, filed Feb. 14, 2005.
Initial Rule 26(A) Disclosure by Plaintiff Scantibodies Laboratory, Inc., filed Feb. 28, 2005.
Defendant's Initial Disclosures Pursuant to Fed. R. Civ. P. 26(a), filed Feb. 28, 2005.
Why Nichols is our PTH Vendor, submitted in Defendant's Supplemental Initial Disclosures.
Scantibodies' First Set of Interrogatories to Defendants/Counterclaimants Immutopics, Inc. and Immutopics International, LLC (Nos. 1-14), filed Mar. 7, 2005.
Scantibodies' First Request for Production of Documents to Defendants/Counterclaimants Immutopics, Inc. and Immutopics International, LLC (Nos. 1-63), filed Mar. 7, 2005.
Defendants' First Set of Interrogatories to Plaintiff Pursuant to Fed. R. Civ. P. 33 (Nos. 1-4), filed Mar. 9, 2005.
Defendants' First Request for Admissions to Plaintiff Pursuant to Fed. R. Civ. P. 36 (Nos. 1-11), filed Mar. 9, 2005.
Defendants' First Requests for Production of Documents and Things Pursuant to Fed. R. Civ. P. 34 (Nos. 1-51), filed Mar. 9, 2005.
Stipulation and Protective Order Regarding Confidential Information, filed Mar. 18, 2005.
Order Denying Defendants' Motion for Summary Judgment of Invalidity of United States Patent No. 6,030,790 and Granting Summary Adjudication That the Patent is Not Anticipated or Rendered Obvious by Certain Prior Art References, filed May 3, 2005.
Order Denying Defendants' Motion for Summary Judgment of Noninfringement and Denying Plaintiff's Motion for Summary Judgment of Infringement of United States Patent No. 6,030,790, filed May 3, 2005.
Certificate of Correction pertaining to inventorship for U.S. Patent No. 6,030,790, dated Aug. 6, 2002.
Certificate of Correction pertaining to text for U.S. Patent No. 6,030,790, dated Aug. 27, 2002.
Delmas et al., Molecular Immunology (1985) 22:675-679.
Desplan et al., The Lancet (Jul. 1977):198-199.
Habener and Potts, Endocrinology (1979) 105:115-119.
Habener et al., Endocrine Research Comminications (1974) 1:1-17.
Hanley and Wellings, Journal of Immunoassay (1985) 6:245-259.
Hendy et al., Proceedings of the Society for Endocrinology 26P-27P.
John et al., Journal of Clinical Endocrinology and Metabolism (1999) 84(11):4287-4290.
Kohno et al., J. Clin. Lab. Anal. (1998) 12:268-275.
Nussbaum et al., Methods in Enzymology (1985) 109:625-638.
Rapley et al., Immunology (1993) 78:379-386.
Tampe et al., J. Immunoassay (1992) 13(1):1-13.
Vieira et al., Brazilian J. Med. Biol. Res. (1987) 20:721-729.
Xie and Abou-Samra, Endocrinology (1998) 139:4563-4567.
Subpoena in a Civil Case for Dr. Claude Arnaud, filed May 4, 2005.
Subpoena in a Civil Case for Dr. Ellen Vitetta, filed May 4, 2005.
Subpoena in a Civil Case for Joseph O. Falkinham, III, filed May 4, 2005.
Subpoena in a Civil Case for Gerald Bjorge, filed May 4, 2005.
Subpoena in a Civil Case for Larry W. Evans, filed May 4, 2005.
Subpoena in a Civil Case for Dr. Wolf-Georg Forsmann, filed May 4, 2005.
Subpoena in a Civil Case for Dr. Knut Adermann, filed May 4, 2005.
Subpoena in a Civil Case for Dr. Dieter Hock, filed May 4, 2005.
Subpoena in a Civil Case for Dr. Markus Magerlein, filed May 4, 2005.
Subpoena in a Civil Case for Dr. Thomas Godemeyer, filed May 4, 2005.
Subpoena in a Civil Case for Dr. Michael Harder, filed May 4, 2005.
Subpoena in a Civil Case for Dr. Randy Ringold, filed May 4, 2005.
Subpoena in a Civil Case for Dr. K. Ramakrishan, filed May 4, 2005.
Subpoena in a Civil Case for Eva Guthrie, filed May 4, 2005.
Subpoena in a Civil Case for Julie Lu, filed May 4, 2005.
Nichols' Opposition to Scantibodies' Motion in Limine No. 1 (That Seeks to Exclude Dr. Hall's Experiments), filed May 5, 2005.
Nichols Institute Diagnostics, Inc.'s Opposition to Scantibodies' Motion in Limine No. 2, Nichols' Opposition to Scantibodies Motion in Limine to Exclude Expert Opinion and Other Evidence Regarding Opinion of Counsel, filed May 5, 2005.
Nichols Institute Diagnostics, Inc.'s Opposition to Scantibodies' Motion in Limine No. 3 to Preclude Nichols' Reliance on Doctrine of Equivalents, filed May 5, 2005.
Declaration of Jane Babin in Support of Nichols Institute Diagnostics, Inc.'s Opposition to Scantibodies' in Limine Motion No. 3, filed May 5, 2005.
Nichols Institute Diagnostics, Inc.'s Opposition to Scantibodies' in Limine Motion No. 5, Opposition to Scantibodies' Motion to Preclude Evidence of a Hypothetical Negotiation Between Scantibodies and Nichols, filed May 5, 2005.
Declaration of April Alex in Support of Nichols Institute Diagnostics, Inc.'s Opposition to Scantibodies' in Limine Motion No. 5, filed May 5, 2005.
Nichols Institute Diagnostics, Inc.'s Opposition to Scantibodies' Motion in Limine No. 7 to Exclude Evidence Regarding Medicare Billing, filed May 5, 2005.
Order Granting Nichols Institute Diagnostics Inc.'s Ex Parte Application to Accept Nichols' in Limine Motion No. 21 as Timely Filed, filed May 5, 2005.
Scantibodies' Opposition to Nichols' Motion in Limine No. 1, filed May 5, 2005.
Scantibodies' Opposition to Nichols' Motion in Limine No. 2, filed May 5, 2005.
Scantibodies' Opposition to Nichols' Motion in Limine No. 3, filed May 5, 2005.
Scantibodies' Opposition to Nichols' Motion in Limine No. 4, filed May 5, 2005.
Scantibodies' Opposition to Nichols' Motion in Limine No. 5, filed May 5, 2005.
Scantibodies' Opposition to Nichols' Motion in Limine No. 6, filed May 5, 2005.
Scantibodies' Opposition to Nichols' Motion in Limine No. 7, filed May 5, 2005.
Scantibodies' Opposition to Nichols' Motion in Limine No. 8, filed May 5, 2005.
Scantibodies' Opposition to Nichols' Motion in Limine No. 10, filed May 5, 2005.

Scantibodies' Opposition to Nichols' Motion in Limine No. 11, filed May 5, 2005.
Scantibodies' Opposition to Nichols' Motion in Limine No. 13, filed May 5, 2005.
Scantibodies' Opposition to Nichols' Motion in Limine No. 14, filed May 5, 2005.
Scantibodies' Opposition to Nichols' Motion in Limine No. 15, filed May 5, 2005.
Scantibodies' Opposition to Nichols' Motion in Limine No. 16, filed May 5, 2005.
Scantibodies' Opposition to Nichols' Motion in Limine No. 17, filed May 5, 2005.
Scantibodies' Opposition to Nichols' Motion in Limine No. 18, filed May 5, 2005.
Scantibodies' Opposition to Nichols' Motion in Limine No. 19, filed May 5, 2005.
Scantibodies' Opposition to Nichols' Motion in Limine No. 20, filed May 5, 2005.
Stipulation and Notice of Withdrawal Regarding Four Motions in Limine, filed May 5, 2005.
Supplemental Subpoena in a Civil Case for Ping Gao, filed May 6, 2005.
Supplemental Subpoena in a Civil Case for Scantibodies Laboratory, Inc., filed May 6, 2005.
Supplemental Subpoena in a Civil Case for Scantibodies Clinical Laboratory, Inc., filed May 6, 2005.
Scantibodies' Ex Parte Application Requesting Correction of Order Denying Defendants' Motion for Summary Judgment of Invalidity, filed May 9, 2005.
Declaration of Katherine L. Parker in Support of Scantibodies' Ex Parte Application Requesting Correction of Order Denying Defendants' Motion for Summary Judgment of Invalidity, filed May 9, 2005.
[Proposed] Order Granting Scantibodies' Ex Parte Application Requesting Correction of Order Denying Defendants' Motion for Summary Judgment of Invalidity, filed May 9, 2005.
Transcript of Motion in Limine Hearing/Pretrial Conference, May 9, 2005.
Transcript of Motions in Limine Hearing, May 10, 2005.
Transcript of Motions in Limine Hearing, May 11, 2005.
Scantibodies Clinical Laboratory, Inc., and Scantibodies Laboratory, Inc.'s Second Supplemental Exhibit List, filed May 11, 2005.
Objections to Nichols' Subpoena in a Civil Case and Request for Production of Documents to Vivian Shen, filed May 11, 2005.
Objections to Nichols' Subpoena in a Civil Case and Request for Production of Documents to Stephen Scheibel, filed May 11, 2005.
Objections to Nichols' Subpoena in a Civil Case and Request for Production of Documents to Dr. Richard Lerner, filed May 11, 2005.
Objections to Nichols' Subpoena in a Civil Case and Request for Production of Documents to Randolph Wall, Ph.D., filed May 11, 2005.
Objections to Nichols' Subpoena in a Civil Case and Request for Production of Documents to Mark Gray, filed May 11, 2005.
Objections to Nichols' Subpoena in a Civil Case and Request for Production of Documents to Allen Garrett, filed May 11, 2005.
Objections to Nichols' Subpoena in a Civil Case and Request for Production of Documents to Steven Jones, filed May 11, 2005.
Objections to Nichols' Subpoena in a Civil Case and Request for Production of Documents to Zan Yang, filed May 11, 2005.
Objections to Nichols' Subpoena in a Civil Case and Request for Production of Documents to Thomas G. Wiseman, filed May 11, 2005.
Objections to Nichols' Subpoena in a Civil Case and Request for Production of Documents to Damon Cook, filed May 11, 2005.
Objections to Nichols' Subpoena in a Civil Case and Request for Production of Documents to Frank Hall, filed May 11, 2005.
Objections to Nichols' Subpoena in a Civil Case and Request for Production of Documents to Janet Sharp, filed May 11, 2005.
Objections to Nichols' Subpoena in a Civil Case and Request for Production of Documents to Michael Nordstrom, filed May 11, 2005.
Objections to Nichols' Subpoena in a Civil Case and Request for Production of Documents to Thomas Cantor, filed May 11, 2005.
Objections to Nichols' Subpoena in a Civil Case and Request for Production of Documents to Dr. J. Stuart Woodhead, filed May 11, 2005.
Objections to Nichols' Subpoena in a Civil Case and Request for Production of Documents to Ping Gao, filed May 11, 2005.
Objections to Nichols' Subpoena in a CivilCase and Request for Production of Documents to Scantibodies Laboratory, Inc., filed May 11, 2005.
Objections to Nichols' Subpoena in a Civil Case and Request for Production of Documents to Scantibodies Clinical Laboratory, Inc., filed May 11, 2005.
Objections to Nichols' Supplemental Subpoena in a Civil Case and Request for Production of Documents to Ping Gao, filed May 11, 2005.
Objections to Nichols' Supplemental Subpoena in a Civil Case and Request for Production of Documents to Scantibodies Laboratory Inc., filed May 11, 2005.
Objections to Nichols' Supplemental Subpoena in a Civil Case and Request for Production of Documents to Scantibodies Clinical Laboratory Inc., filed May 11, 2005.
Stipulation and [Proposed] Order Re Early Access to Courtroom 2 and Set Up of Audio Visual Equipment, filed May 11, 2005.
Scantibodies' Proposed Voir Dire Questions, filed May 12, 2005.
Nichols Proposed Voir Dire Questions, filed May 12, 2005.
Transcript of Status Conference, May 12, 2005.
Scantibodies' Supplemental Briefing in Support of Scantibodies' Motion in Limine No. 5 Re Timing and Parties to Hypothetical Negotiation, filed May 13, 2005.
Plaintiff's Memorandum Concerning Freedom of Contract and Retroactivity (in Connection with Defendant's Motion in Limine #5), filed May 13, 2005.
Nichols' Amended Exhibit List to Memorandum of Fact and Law, filed May 13, 2005.
Scantibodies' Trial Brief on Inequitable Conduct, filed May 13, 2005.
Response to Trial Subpoena Request for Production for Claude Arnaud, M.D., filed May 16, 2005.
Response to Trial Subpoena Request for Production for Larry W. Evans, filed May 16, 2005.
Response to Trial Subpoena Request for Production for Gerald H. Bjorge, filed May 16, 2005.
Response to Trial Subpoena Request for Production for Ellen S. Vitetta, filed May 16, 2005.
Response to Trial Subpoena Request for Production for Joseph O. Falkinham, filed May 16, 2005.
Scantibodies Clinical Laboratory, Inc., and Scantibodies Laboratory, Inc.'s Third Supplemental Exhibit List, filed May 16, 2005.
Notice of Deposition of Allan Garret, filed May 16, 2005.
Notice of Deposition of Stephen Jones, filed May 16, 2005.
Notice of Document Discrepancies, Supplemental Exhibit List, filed by Scantibodies, May 17, 2005.
Notice of Document Discrepancies, Supplemental Briefing, filed by Scantibodies, May 17, 2005.
Scantibodies' Objections to Nichols' Amended Exhibit List, filed May 17, 2005.
Bench Trial Transcript—vol. I, May 16, 2005.
Bench Trial Transcript—vol. II, May 17, 2005.
Bench Trial Transcript—vol. III, May 18, 2005.
Bench Trial Transcript—vol. IV, May 19, 2005.
Bench Trial Transcript—vol. V, May 23, 2005.
Bench Trial Transcript—vol. VI, May 24, 2005.
Bench Trial Transcript—vol. VII, May 25, 2005.
Bench Trial Transcript—vol. VIII, May 27, 2005.
Order on Motion in Limine Nichols No. 3, filed May 19, 2005.
Nichols' Objections to Scantibodies' Amended Exhibit Lists, filed May 20, 2005.
[Proposed] Jury Instructions of Plaintiff Nichols, filed May 25, 2005.
Nichols Institute Diagnostics, Inc.'s [Proposed] Verdict Form Regarding Infringement and Validity, filed May 25, 2005.
Nichols Institute Diagnostics, Inc.'s [Proposed] Verdict Form Regarding Damages and Willfulness, filed May 25, 2005.
Scantibodies' Notice of Motion and Motion for Judgment on Inequitable Conduct and Invalidity, filed May 25, 2005.

Scantibodies' Memorandum of Points and Authorities in Support of Motion for Judgment on Inequitable Conduct and Invalidity, filed May 25, 2005.
Declaration of Katherine L. Parker in Support of Scantibodies' Motion for Judgment on Inequitable Conduct and Invalidity, filed May 25, 2005.
Scantibodies' Proposed Jury Instructions, filed May 25, 2005.
Scantibodies' Proposed Jury Instructions on Damages and Willfulness, filed May 25, 2005.
Scantibodies' Proposed Special Verdict Form, filed May 25, 2005.
Scantibodies' Proposed Special Verdict Form on Damages and Willfulness, filed May 25, 2005.
Notice of Document Discrepancies, Supplemental Exhibit List filed by Scantibodies, May 26, 2005.
Scantibodies' Brief Regarding Materiality of Rejection by Foreign Patent Office, filed May 26, 2005.
Scantibodies' Bench Memorandum Requesting Corrective Jury Instruction, filed May 26, 2005.
Nichols' Second Amended Exhibit List to Memorandum of Fact and Law, filed May 27, 2005.
Jury Trial Transcript—Day 1, May 25, 2005.
Jury Trial Transcript—Day 2, May 26, 2005.
Jury Trial Transcript—Day 3, May 31, 2005.
Jury Trial Transcript—Day 4, Jun. 1, 2005.
Jury Trial Transcript—Day 5, Jun. 2, 2005.
Jury Trial Transcript—Day 6, Jun. 6, 2055.
Jury Trial Transcript—Day 7, Jun. 7, 2005.
Jury Trial Transcript—Day 8, Jun. 8, 2005.
Jury Trial Transcript—Day 9, Jun. 9, 2005.
Jury Trial Transcript—Day 10, Jun. 13, 2005.
Jury Trial Transcript—Day 11, Jun. 14, 2005.
Jury Trial Transcript—Day 12, Jun. 15, 2005.
Jury Trial Transcript—Day 13, Jun. 16, 2005.
Jury Trial Transcript—Day 14, Jun. 20, 2005.
Jury Trial Transcript—Day 15, Jun. 21, 2005.
Jury Trial Transcript—Day 16, Jun. 22, 2005.
Jury Trial Transcript—Day 17, Jun. 23, 2005.
Jury Trial Transcript—Day 18, Jun. 27, 2005.
Scantibodies' Proposed Supplemental Jury Instruction Regarding "Idea" of a Patent, filed Jun. 2, 2005.
Notice of Document Discrepancies, Second Amended Exhibit List, filed by Nichols Institute, Jun. 3, 2005.
Nichols' Third Amended Exhibit List to Memorandum of Fact and Law, filed Jun. 5, 2005.
Nichols Institute Diagnostics, Inc.'s Notice of and Ex Parte Application for Order to File Third Amended Exhibit List to Memorandum of Fact and Law, filed Jun. 6, 2005.
Declaration of April M. Alex in Support of Nichols' Ex Parte Application for Order to File Third Amended Exhibit List to Memorandum of Fact and Law, filed Jun. 6, 2005.
[Proposed] Order Granting Nichols Institute Diagnostics, Inc.'s Ex Parte Application to File Its Third Amended Exhibit List to Memorandum of Fact and Law, filed Jun. 6, 2005.
Scantibodies Clinical Laboratory, Inc. and Scantibodies Laboratory, Inc.'s Fourth Supplemental Exhibit List, filed Jun. 6, 2005.
Scantibodies' Second Proposed Supplemental Jury Instruction (Regarding Inventorship), filed Jun. 8, 2005.
Scantibodies' Amended Proposed Special Verdict Form, filed Jun. 8, 2005.
Nichols Institute Diagnostics, Inc.'s Notice of and Ex Parte Application for Order to File Its [Proposed] Second Supplemental Jury Instructions of Plaintiff Nichols, filed Jun. 9, 2005.
Declaration of Joshua G. Gigger in Support of Nichols' Ex Parte Application for Order to File [Proposed] Second Supplemental Jury Instructions of Plaintiff Nichols, filed Jun. 9, 2005.
[Proposed] Second Supplemental Jury Instructions of Plaintiff Nichols, filed Jun. 9, 2005.
[Proposed] Order Granting Nichols Institute Diagnostics, Inc.'s Ex Parte Application to File [Proposed] Second Supplemental Jury Instructions of Plaintiff Nichols, filed Jun. 9, 2005.
Deposition of Knut Adermann, Exhibit No. 11.
Deposition of James T. Carmichael, Exhibit No. 15.
Deposition of Roger T. Frost, Exhibit No. 18.
Deposition of Allen Garrett, Exhibit 20.
Deposition of Allen Garrett vol. 2, Exhibit No. 21.
Deposition of Michael Harder, Exhibit No. 23.
Deposition of Dieter Hock, Exhibit No. 24.
Deposition of Hartmut H. Malluche, No. 27.
Deposition of Vivian Shen, Exhibit No. 34.
Deposition of Ellen S. Vitetta, Exhibit No. 35.
Judgment Following Court and Jury Trial, Filed Jun. 29, 2005.
Brossard et al., Journal of Clinical Endocrinology and Metabolism (1993) 77:413-419.
Caetano et al., Equus Genome Res. (1999) 9(12):1239-1249.
D'Amour et al., J. Bone Miner. Res. (1996) 11:1075-1085.
Fuhr et al., Klin Wochenschr (1955) 33:729-730.
Fujimori et al., Therapeutic Apheresis and Dialysis (2004) 8(6):474-479.
K/DOQI Clinical Practice Guidelines for Bone Metabolism and Disease in Chronic Kidney Disease, Draft Guideline Statements and Treatment Algorithms, Feb. 2003.
Kohler and Milstein, Nature (1975) 256:495-497.
Magerlein, Ph.D. Dissertation, Oct. 31, 1995, Ruprecht Karls University of Heidelberg (Original in German).
Magerlein, Ph.D. Dissertation, Oct. 31, 1995, Ruprecht Karls University of Heidelberg (English Translation).
Malluche, The Importance of Bone Health in ERSD: Out of the Frying Pan, Into the Fire?, World Congress on Nephrology, Berlin, Germany, Jun. 2003.
Mayer et al., Endocrinology (1979) 104:1778-1784.
Watson et al., Molecular Biology of the Gene, 4$^{th}$ edition, (1987) The Bejamin/Cummings Pub. Co., p. 224.
Wood et al., PNAS USA (1985) 82:1585-1588.
Woodhead, Clin. Biochem. (1990) 23:17-21.
Scantibodies' Notice of Motion and Motion for Summary Judgment of Invalidity and Noninfringement, filed Feb. 18, 2005.
Declaration of Randolph Wall, PHD in Support of Scantibodies' Memorandum of Points and Authorities in Support of Motion for Summary Judgment of Invalidity and Noninfringement, filed Feb. 18, 2005.
Declaration of Dr. Wolf Grosskopf in Support of Motion for Summary Judgment of Invalidity and Noninfringement, filed Feb. 18, 2005.
[Proposed] Order Granting Scantibodies' Motion for Summary Judgment of Invalidity and Noninfringement, filed Feb. 18, 2005.
Declaration of K. Ramakrishan, Ph.D. in Support of Nichols Institute Diagnostics, Inc.'s Opposition to Motion for Summary Judgment of Invalidity and Non-Infringement, filed Mar. 7, 2005.
Declaration of Eva Guthrie in Support of Nichols Institute Diagnostics, Inc.'s Opposition to Motion for Summary Judgment of Invalidity and Non-Infringement, filed Mar. 7, 2005.
Declaration of John E. Peterson in Support of Nichols Institute Diagnostics, Inc.'s Opposition to Motion for Summary Judgment of Invalidity and Non-Infringement, filed Mar. 7, 2005.
Reply Memorandum of Points and Authorities in Support of Scantibodies' Motion For Summary Judgment of Invalidity and Noninfringement, filed Mar. 14, 2005.
Notice of Motion and Motion For Nichols Institute Diagnostics, Inc.'s Renewed Motion For Judgment As A Matter Of Law, filed Jul. 13, 2005.
Memorandum of Points and Authorities in Support of Nichols Institute Diagnostics, Inc.'s Renewed Motion for Judgment As a Matter of Law, filed Jul. 13, 2005.
Declaration of April M. Alex In Support Of Nichols Institute Diagnostics, Inc.'s Renewed Motion For Judgment As A Matter Of Law, filed Jul. 13, 2005.
[Proposed] Order Granting Nichols Institute Diagnostics, Inc.'s Renewed Motion for Judgment As A Matter of Law, filed Jul. 13, 2005.
Memorandum Of Points and Authorities In Support Of Nichols Institute Diagnostics, Inc.'s Motion For A New Trial, filed Jul. 13, 2005.
Declaration of Charles B. Cohler In Support Of Nichols Institute Diagnostics, Inc.'s Motion For A New Trial, filed Jul. 13, 2005.
Declaration of Julia A. Miller in Support of Nichols Institute Diagnostics, Inc.'s Motion for a New Trial, filed Jul. 13, 2005.

Scantibodies' Notice of Motion and (1) Motion For Relief From Judgment of Infringement As To Claims 17 and 21 and (2) Renewed Motion For Judgment As A Matter of Law, filed Jul. 14, 2005.

Scantibodies' Memorandum Of Points And Authorities In Support Of (1) Motion for Relief From Judgment of Infringement As To Claims 17 and 21 and (2) Renewed Motion For Judgment As A Matter Of Law, filed Jul. 14, 2005.

Declaration of M. Andrew Woodmansee In Support Of (1) Motion For Relief From Judgment Of Infringement As To Claims 17 and 21 and (2) Renewed Motion For Judgment As A Matter of Law, filed Jul. 14, 2005.

Declaration of M. Andrew Woodmansee In Support Of Scantibodies' Application To Tax Costs, filed Jul. 14, 2005.

Scantibodies' Consolidated Opposition To Nichols' Motion For Judgment As a Matter Of Law And Nichols' Motion for New Trial, filed Aug. 1, 2005.

Declaration Of M. Andrew Woodmansee In Support Of Scantibodies' Consolidated Opposition To Nichols' Motion For Judgment As A Matter Of Law and Nichols' Motion for New Trial, filed Aug. 1, 2005.

Nichols Institute Diagnostics, Inc.'s Opposition To Scantibodies' (1) Motion For Relief From Judgment Of Infringement As To Claims 17 and 21 And (2) Motion For Judgment As A Matter of Law, filed Aug. 1, 2005.

Declaration of April M. Alex in Support Of Nichols Institute Diagnostics, Inc.'s Opposition to Scantibodies' (1) Motion For Relief From Judgment Of Infringement As To Claims 17 and 21 And (2) Motion For Judgment As A Matter Of Law, filed Aug. 1, 2005.

[Proposed] Order Denying Scantibodies' Motion for Judgment As a Matter of Law, filed Aug. 1, 2005.

Opposition Of Nichols Institute Diagnostics, Inc. To Application To Tax Costs, filed Aug. 1, 2005.

Scantibodies' Reply Brief In Support Of (1) Motion For Relief From Judgment Of Infringement As To Claims 17 and 21 And (2) Renewed Motion For Judgment As A Matter Of Law, filed Aug. 8, 2005.

Declaration of M. Andrew Woodmansee In Support Of Scantibodies' Reply Brief In Support Of (1) Motion For Relief From Judgment Of Infringement As To Claims 17 and 21 And (2) Renewed Motion For Judgment As A Matter Of Law, filed Aug. 8, 2005.

Nichols Institute Diagnostics, Inc.'s Reply To Scantibodies' Opposition To Nichols Renewed Motion For Judgment As A Matter Of Law, filed Aug. 8, 2005.

Declaration of April M. Alex In Support of Nichols Institute Diagnostics, Inc.'s Reply To Scantibodies' Opposition To Nichols Renewed Motion For Judgment As A Matter Of Law, filed Aug. 8, 2005.

Reply to Scantibodies' Opposition To Nichols Motion For A New Trial, filed Aug. 8, 2005.

Declaration of Katherine L. Parker In Support Of Scantibodies' Opposition To Nichols' Motion To Retax Costs, filed Aug. 23, 2005.

Reply Memorandum In Support Of Nichols Institute Diagnostics, Inc.'s Motion To Retax Costs, filed Aug. 29, 2005.

Order Re: Post-Verdict Motions, filed Aug. 30, 2005.

Request For Ex Parte ReExamination of United States Patent No. 6,689,566, filed Aug. 22, 2005.

Colford et al., The Endocrine Society, Programs & Abstracts, 79th Annual Meeting, Jun. 11-14, 1997, Minneapolis Minnesota, "Isolation and Characterization of Large Molecular Weight Fragments of PTH".

Colford et al., J. Bone & Miner. Res. (1997) 12(Supp. 1):S318 (F368).

Colford et al., Clin. Chem. (1997) 43(6):S189 (381).

Colford et al., 10th International Congress of Endocrinology Program and Abstracts (1996), entitled "Data Suggesting the Presence of a Circulating Inhibitor to PTH".

Colford et al., Meeting of the Endocrine Society (1996), entitled "Comparing Specificity for Intact Human Parathyroid Hormone Between INCSTAR PTHSP and Nichols Intact PTH Assays".

Kohno et al., J. Clin. Lab. Anal. (1998) 12:268-275.

Defendants' Second Amended Answer To Plaintiff's Complaint And Counterclaims, filed Dec. 31, 2004.

Letter from Immutopics' counsel to Scantibodies' counsel dated Aug. 5, 2005.

Colford 1997 Abstract Presentation.

Jensen et al., poster from the 1996 Annual Meeting of the Endocrine Society, San Francisco, CA, entitled "Comparing Specificity for Intact Human Parathyroid Hormone Between INCSTAR PTHSP and Nichols Intact PTH Assays".

Declaration of John Colford.

Gao et al., J. Bone Miner. Res. (2001) 16(4):605-614.

Order Granting Request for Ex Parte Reexamination for U.S. Patent No. 6,689,566, mailed on Sep. 14, 2005, Control No. 90/007,685.

Written Submissions In Preparation Of The Oral Proceedings Scheduled For Nov. 15, 2005, submissions dated Sep. 15, 2005.

Petition Filed by Von Kreisler Selting Werner with the European Patent Office on Sep. 15, 2005.

English Translation of the Petition Filed by Von Kreisler Setting Werner with the European Patent Office on Sep. 15, 2005.

Official Communication by the European Patent Office on Sep. 29, 2005.

English Translation of the Official Communication by the European Patent Office on Sep. 29, 2005.

Petition filed by Patentee in response to the Official Communication dated Sep. 29, 2005 (in German).

Brief Communication from the Opposition Division dated Oct. 5, 2005 (in German).

Office Action in Ex Parte Reexamination of U.S. Patent 6,030,790, Control No. 90/007,412, mailed on Sep. 28, 2005.

Harlow et al., Antibodies, 1988, pp. 366, 428, 584, and 579.

First Amendment and Response to Reexamination Office Action, filed Nov. 28, 2005.

Information Disclosure Statement for Reexamination No. 90/007,412, filed Nov. 28, 2005.

Request for Ex Parte Reexamination of U.S. Patent 6,689,566 per Rule 1.501 et seq., filed on Sep. 28, 2005 by Immutopics.

Order Granting Request for Reexamination of U.S. Patent 6,689,566, mailed on Oct. 27, 2005, control No. 90/007,732.

Declaration of John E. Peterson in Support of Nichols Institute Diagnostics. Inc.'s Motion for Permanent Injunction, filed Sep. 22, 2005.

Settled Findings of Fact and Conclusions of Law on Inequitable Conduct and Order Adjudicating Patent Enforceable, filed Oct. 14, 2005.

Scantibodies' Memorandum of Points and Authorities in Support of Opposition to Nichols' Motion for Permanent Injunction, filed Oct. 14, 2005.

Declaration of Katherine L. Parker in Support of Scantibodies' Opposition to Nichols' Motion for Permanent Injunction, filed Oct. 14, 2005.

Declaration of Allen Garrett in Support of Scantibodies' Opposition to Nichols' Motion for Permanent Injunction, filed Oct. 14, 2005.

Declaration of Dr. Hartmut Malluche in Support of Scantibodies' Opposition to Nichols' Motion for Permanent Injunction, filed Oct. 14, 2005.

Declaration of Dr. Richard Amerling in Support of Scantibodies' Opposition to Nichols' Motion for Permanent Injunction, filed Oct. 14, 2005.

Declaration of Dr. James Tumlin in Support of Scantibodies' Opposition to Nichols' Motion for Permanent Injunction, filed Oct. 14, 2005.

Declaration of Dr. Hassan Fehmi in Support of Scantibodies' Opposition to Nichols' Motion for Permanent Injunction, filed Oct. 14, 2005.

Declaration of Dr. Clarence Wheeler in Support of Scantibodies' Opposition to Nichols' Motion for Permanent Injunction, filed Oct. 14, 2005.

Nichols Institute Diagnostics, Inc.'s Reply Motion for a Permanent Injunction, filed Oct. 24, 2005.

Declaration of Dr. Delbert A. Fisher in Support of Nichols Institute Diagnostics, Inc.'s Reply Motion for a Permanent Injunction, filed Oct. 24, 2005.

Declaration of Dr. Claude Arnaud in Support of Nichols Institute Diagnostics, Inc.'s Reply Motion for a Permanent Injunction, filed Oct. 24, 2005.

Declaration of Katherine L. Parker in Support of Opposition to Nichols' Motion for Clarification of the Court's Order Dated Aug. 30, 2005 Regarding Motion in Limine No. 5, filed Oct. 24, 2005.

Nichols Institute Diagnostics, Inc.'s Objections To and Ex Parte Application to Strike Statements Filed in Support of Scantibodies' Opposition to Nichols' Motion for a Permanent Injunction, filed Oct. 25, 2005.
Scantibodies' Opposition to Nichols' Objections To and Ex Parte Application to Strike Statements Filed in Support of Scantibodies' Opposition to Nichols' Motion for a Permanent Injunction, filed Oct. 27, 2005.
Scantibodies' Emergency Motion To Stay Injunction and Damages/Willfulness Trial Pending Appeal, filed Nov. 17, 2005.
Appellant's Appendix to Scantibodies' Emergency Motion To Stay Injunction and Trial Pending Appeal, filed Nov. 17, 2005.
Federal Circuit Appeal Information Sheet, filed Nov. 17, 2005.
Office Action—Examination Report dated Jul. 14, 2003 for EP application No. 00 902 406.8-2404.
Response to Office Action—Examination Report dated Jul. 14, 2003, response dated Jan. 23, 2004.
Office Action—Examination Report dated Mar. 16, 2004, for EP application No. 00 902 406.8-2404.
Response to Office Action—Examination Report dated Mar. 16, 2004, response dated Sep. 8, 2004.
Office Action—Examination Report dated May 6, 2005, for EP application No. 00 902 406.8-2404.
Written Submissions prior to the Oral Proceedings, dated Sep. 15, 2005.
Letter from counsel following phone conference with examiner and in anticipation of Oral Proceedings, dated Oct. 4, 2005.
Result of Consultation of Sep. 29, 2005, dated Oct. 12, 2005.
Result of Consultation of Oct. 4, 2005, dated Oct. 12, 2005.
Minutes of the Oral Proceedings on Oct. 17, 2005, dated Nov. 9, 2005.
Official Action (and English Translation) for Japanese Patent Application No. 2000-593958, mailed on Aug. 13, 2004.
Partial Translation of the Response filed Feb. 9, 2005.
Decision of Rejection (and English Translation) for Japanese Patent Application No. 2000-593958, mailed on Aug. 9, 2005.
Plaintiff's Responses To Defendants' First Set Of Interrogatories Pursuant to Fed. R. Civ. P. 33 (Nos. 1-4), filed Apr. 22, 2005.
Plaintiff's Responses To Defendants' First Set Of Requests For Admissions Pursuant To Fed. R. Civ. P. 36 (Nos. 1-11), filed Apr. 22, 2005.
Defendants' Second Request For Admissions To Plaintiff Pursuant To Fed. R. Civ. P. 36 (No. 12-21), filed Jun. 8, 2005.
Application For An Order For The Issuance Of Letter Rogatory; Memorandum Of Points And Authorities; Declaration Of Dan P. Sedor, filed Jun. 9, 2005.
Letter Rogatory, filed Jun. 9, 2005.
Scantibodies' Second Set Of Interrogatories To Defendants/Counterclaimants Immutopics, Inc. And Immutopics International, LLC (Nos. 15-19) filed Jun. 10, 2005.
Scantibodies' Second Request For Production Of Documents To Defendants/Counterclaimants Immutopics, Inc. And Immutopics International, LLC (Nos. 64-69) filed Jun. 10, 2005.
Scantibodies' First Request For Admissions To Defendants/Counterclaimants Immutopics, Inc. And Immutopics International, LLC )Nos. 1-110), filed Jun. 10, 2005.
Objections Of Third-party Respondent Richard E. Reitz. M.D., filed Jun. 13, 2005.
Notice Of Deposition Of Scantibodies Laboratory, Inc. Pursuant to F.R.C.P. 30(b)(6), filed Jun. 17, 2005.
Scantibodies' Third Request For Production Of Documents To Defendants/Counterclaimants Immutopics, Inc. And Immutopics International, LLC (No. 70) filed Jul. 1, 2005.
Plaintiff/Counterdefendant's Objections To Defendant/Counterclaimant's Deposition Notice Pursuant To F.R.C.P. 30(B)(6), filed Jul. 8, 2005.
Plaintiff's Responses To Defendants' Second Set of Interrogatories Pursuant to Fed. R. Civ. P. 33 (No. 5), filed Jul. 12, 2005.
Responses to Defendants' Second Request For Admissions To Plaintiff Pursuant To Fed. R. Civ. P. 36 (Nos. 12-21), filed Jul. 12, 2005.
Defendants' Third Request For Admissions To Plaintiff Pursuant To Fed. R. Civ. P. 36 (Nos. 22-23), filed Jul. 12, 2005.
Defendants/Counterclaimants' Response To Scantibodies' First Requests For Admissions (Nos. 1-110), filed Jul. 12, 2005.
Defendants/Counterclaimants' Response To Scantibodies' Second Request For Production Of Documents (Nos. 64-69), filed Jul. 13, 2005.
Defendants' Fourth Request For Admissions To Plaintiff Pursuant To Fed. R. Civ. P. 36 (Nos. 24-37), filed Jul. 15, 2005.
Objections To Subpoena And Notice Of Deposition Of Peng Chen, filed Jul. 25, 2005.
Defendants' Fifth Request For Admissions To Plaintiff Pursuant To Fed. R. Civ. P. 36 (Nos. 38-47), filed Jul. 27, 2005.
Scantibodies' Third Set of Interrogatories to Defendants/Counterclaimants Immutopics, Inc. And Immutopics International, LLC (Nos. 20-24), filed Aug. 1, 2005.
Scantibodies' Second Request For Admissions To Defendants/Counterclaimants Immutopics, Inc. And Immutopics International, LLC (Nos. 111-276), filed Aug. 1, 2005.
Scantibodies' Fourth Request For Production Of Documents And Things To Defendants/Counterclaimants Immutopics, Inc. And Immutopics International, LLC (Nos. 71-88), filed Aug. 1, 2005.
Defendants/Counterclaimants' Response To Scantibodies' Third Request For Production Of Documents (No. 70), filed Aug. 1, 2005.
Plaintiff's Response To Defendants' Third Request For Admissions Pursuant To Fed. R. Civ. P. 36 (Nos. 22-23), filed Aug. 11, 2005.
Plaintiff's Response to Defendants' Fourth Request For Admissions Pursuant To Fed. R. Civ. P. 36 (Nos. 24-37), filed Aug. 15, 2005.
Notice of Service Deposition Subpoena and Subpoena Duces Tecum on Michael A. Levine, filed Aug. 16, 2005.
Notice of Service Subpoena Duces Tecum On Lori J. Sokoll, filed Aug. 16, 2005.
Notice of Service of Subpoena Duces Tecum On Diasorin Inc., filed Aug. 16, 2005.
Notice of Service of Subpoena Duces Tecum On The Johns Hopkins Medical Institutions, filed Aug. 16, 2005.
Defendants/Counterclaimants' Response to Scantibodies' Second Set of Interrogatories (Nos. 15-19), filed Aug. 16, 2005.
Notice of Service of Deposition Subpoena and Subpoena Duces Tecum on John W. Colford, filed Aug. 17, 2005.
Notice of Service of Deposition Subpoena and Subpoena Duces Tecum on Michael Salvati, filed Aug. 17, 2005.
Declaration of M. Andrew Woodmansee in Support of Motion to Quash Immutopics' Subpoena to Third-Party Dr. Richard Lerner And For Attorneys' Fees, filed Aug. 18, 2005.
Notice of Service of Deposition Subpoena And Subpoena Duces Tecum on Gordon D. Macfarlane, filed Aug. 18, 2005.
Declaration Of John Colford, dated Aug. 18, 2005.
Memorandum Of Points And Authorities In Support Of Plaintiff's Motion To Stay Action Pending Resolution Of Plaintiff's Request To Patent And Trademark Office For Reexamination Of Patent-In-Suit, filed Aug. 22, 2005.
Declaration Of Brian W. Kasell In Support Of Plaintiff's Motion To Stay Action Pending Resolution Of Plaintiff's Request To Patent And Trademark Office For Reexamination Of Patent-In-Suit, filed Aug. 22, 2005.
Stipulation Regarding Briefing Schedule For Plaintiff's Motion To Stay Action Pending Resolution Of Plaintiff's Request To Patent And Trademark Office For Reexamination Of Patent-In-Suit [Proposed] Order Thereon, filed Aug. 22, 2005.
Notice of Service of Subpoena Duces Tecum On Diasorin Inc., filed Aug. 24, 2005.
Notice of Service of Subpoena Duces Tecum On Todd Jensen, filed Aug. 24, 2005.
Notice of Service of Subpoena Duces Tecum On Jon Spring, filed Aug. 24, 2005.
Plaintiff's Response to Defendants' Fifth Request For Admissions Pursuant To Fed. R. Civ. P. 36 (Nos. 38-47), filed Aug. 25, 2005.
Defendants/Counterclaimants' Response to Scantibodies' Third Set Of Interrogatories (Nos. 20-24), filed Aug. 31, 2005.
Defendants/Counterclaimants' Response to Scantibodies' Fourth Request For Production Of Documents (Nos. 71-88), filed Aug. 31, 2005.
Defendant/Counterclaimants' Response To Scantibodies' Second Request For Admissions (Nos. 111-276), filed Aug. 31, 2005.

Defendant's Opposition To Motion To Stay Action Pending Resolution Of Re-examination Of Patent-In-Suit, filed Sep. 2, 2005.
Declaration Of Matthew Newboles In Support Of Defendant's Opposition For Motion To Stay, filed Sep. 2, 2005.
Declaration Of Richard Zahradnik In Support Of Defendants' Opposition For Motion To Stay, filed Sep. 2, 2005.
Plaintiff's Evidentiary Objections To And Request To Strike The Declarations Of Matthew Newboles And Richard Zahradnik And A Portion of Defendants' Opposition Memorandum In Support Of Defendants' Opposition To Plaintiff's Motion For Stay, filed Sep. 12, 2005.
Declaration Of David Cantor In Support Of Plaintiff's Reply To Defendants' Opposition To Plaintiff's Motion To Stay, filed Sep. 12, 2005.
Supplemental Declaration Of Richard Zahradnik In Support of Defendants' Opposition For Motion To Stay, filed Sep. 15, 2005.
Request For Judicial Notice of Recently Discovered Ruling, Re: Motion For Stay, filed Sep. 15, 2005.
Plaintiff's Evidentiary Objections To And Request To Strike The Supplemental Declaration Of Richard Zahradnik In Support Of Defendants' Opposition To Plaintiff's Motion For Stay, filed Sep. 19, 2005.
Order Granting Plaintiff's Motion To Stay Proceedings, filed Sep. 20, 2005.
Notice Of Patent And Trademark Office's Grant Of Plaintiff's Request for Reexamination, filed Sep. 22, 2005.
Bate Stamped Documents Index.
BioActive Intact PTH Assays, bate stamped IMU-2839-2840.
Human BioActive Intact PTH ELISA Kit, bate stamped IMU-2841-2844.
Human BioActive PTH 1-84 ELISA Kit, bate stamped IMU-2845-2846.
PTH (1-84) Specific Label, bate stamped SC 010159.
Human BioActive PTH 1-84 ELISA Kit Label, bate stamped SC 010163.
Whole PTH (1-84) Specific Label, bate stamped SC 010168.
NKF 2004 PTH Abstracts, bate stamped SC 01483-01496.
The Rise in Adynamic Bone Disease in ERSD Patients and the Changing Spectrum of Renal Osteodystrophy, bate stamped SC 001268-001276.
Judgment for the Invalidation of Japanese Patent No. 3457004, cover letter dated Dec. 7, 2005.
Petition For Writ Of Mandamus, filed Nov. 23, 2005.
Nichols Institute Diagnostics, Inc.'s Proposed Single Paragraph Informing Jury Of Posture Of The Case, filed Nov. 29, 2005.
[Proposed] Jury Instructions of Plaintiff Nichols Institute Diagnostics, Inc., filed Nov. 29, 2005.
Scantibodies' Proposed Jury Instructions for Dec. 5, 2005 Damages and Willfulness Trial, filed Nov. 29, 2005.
Declaration of April M. Alex in Support of Plaintiff's Statement of Position on Scantibodies' Claims of Privilege, As the Result of the Court's Statements About Knorr-Bremse At the Hearing of Nov. 7, 2005, filed Nov. 30, 2005.
Nichols' Response to Scantibodies' Emergency Motion to Stay Injunction Pending Appeal, field Dec. 1, 2005.
Appendix to Nichols' Response To Scantibodies' Emergency Motion To Stay Injunction Pending Appeal, field Dec. 1, 2005.
Nichols' Seventh Amended Exhibit List To Memorandum Of Fact And Law, filed Dec. 4, 2005.
Nichols' Eighth Amended Exhibit List To Memorandum Of Fact And Law, filed Dec. 4, 2005.
Scantibodies' Reply in Support Of Its Emergency Motion To Stay Injunction Pending Appeal, filed Dec. 5, 2005.
Scantibodies Clinical Laboratory, Inc. And Scantibodies Laboratory, Inc.'s Witness List & Sixth Supplemental Exhibit List For Damages/Willfulness Trial, filed Dec. 5, 2005.
Nichols' Ninth Amended Exhibit List to Memorandum of Fact And Law, filed Dec. 6, 2005.
Plaintiff Nichols Institute Diagnostics, Inc.'s First Proposed Supplemental Jury Instructions To The Court's Instructions For The Damages Phase Of The Trial, filed Dec. 13, 2005.
Order Granting Nichols' Motion For Entry Of Permanent Injunction And Staying Injunction Pending Appeal, filed Nov. 16, 2005.

Transcript Of Trial Before The Honorable Rudi M. Brewster, vol. VIII Dec. 16, 2005.
D'Amour et al., J. Clinical Endocrinology & Metabolism (2006) 91(1):283-289.
Deposition of Knut Adermann, taken on Jun. 26, 2003.
Deposition of James T. Carmichael, taken on Jun. 26, 2003.
Deposition of Roger T. Frost, taken on Jun. 25, 2003.
Deposition of Allen Garrett, taken on Nov. 6, 2002.
Deposition of Allen Garrett (30(b)(6)), taken on Sep. 19, 2003.
Deposition of Frank Hall, M.D., taken on Sep. 9, 2003.
Deposition of Michael R. Hamrell, taken on Jan. 26, 2005.
Deposition of Michael Harder, taken Jun. 27, 2003.
Deposition of Dieter Hock, Ph.D., taken on Nov. 18, 2002.
Deposition of Hartmut Malluche, M.D., taken on Sep. 26, 2003.
Deposition of Vivian Shen, taken on Jun. 25, 2003.
Deposition of Ellen Vitetta, taken on Jan. 20, 2005.
Deposition of Thomas Wiseman, taken on Jan. 25, 2005.
Scantibodies' Motion to Dismiss Nichols' Cross-Appeal, filed Jan. 10, 2006.
Appellant's Appendix to Scantibodies' Motion to Dismiss Nichols' Cross-Appeal, filed Jan. 10, 2006.
Final Judgment and Stay of Enforcement, filed Jan. 19, 2006.
Declaration of Katherine L. Parker in Support of Scantibodies' Supplemental Brief in Support of Emergency Motion to Stay Injunction Pending Appeal, filed Jan. 19, 2006.
Nichols' Response to Scantibodies' Motion to Dismiss Nichols' Cross-Appeal, filed Jan. 23, 2006.
Plaintiff-Cross Appellant's Appendix to Nichols' Response to Scantibodies' Motion to Dismiss Nichols' Cross-Appeal, filed Jan. 23, 2006.
Scantibodies' Reply in Support of Motion to Dismiss Nichols' Cross-Appeal, filed Jan. 25, 2006.
Declaration of John E. Peterson in Support of Nichols Institute Diagnostics, Inc.'s Motion for Judgment as a Matter of Law on Damages, filed Jan. 27, 2006.
Notice of Motion and Motion for Nichols Institute Diagnostics, Inc.'s Motion for Judgment as a Matter of Law on Damages, filed Jan. 27, 2006.
Memorandum of Points and Authorities in Support of Nichols Institute Diagnostics, Inc.'s Motion for Judgment as a Matter of Law on Damages, filed Jan. 27, 2006.
Nichols Institute Diagnostics, Inc.'s Notice of Motion and Motion for Judgment as a Matter of Law Re: Willfulness and in the Alternative for a New Trial, filed Jan. 27, 2006.
Nichols Institute Diagnostics, Inc.'s Motion for Judgment as a Matter of Law Re: Willfulness and in the Alternative for a New Trial, filed Jan. 27, 2006.
Declaration of April M. Alex in Support of Nichols Institute Diagnostics, Inc.'s Motion for Judgment as a Matter of Law Re: Willfulness and in the Alternative for a New Trial, filed Jan. 27, 2006.
Nichols Institute Diagnostics, Inc.'s Notice of Motion and Motion for Enhancement of Damages, filed Jan. 27, 2006.
Nichols Institute Diagnostics, Inc.'s Memorandum of Points and Authorities in Support of Motion for Enhancement of Damages, filed Jan. 27, 2006.
Declaration of April M. Alex in Support of Motion for Enhancement of Damages, filed Jan. 27, 2006.
Appellants Scantibodies' Opening Brief, filed Jan. 30, 2006.
Order Granting Stay Pending Appeal and Dismissing Nichols' Cross-Appeal, filed Feb. 1, 2006.
Declaration of April M. Alex in Support of Nichols Institute Diagnostics, Inc.'s Application for Award of Attorney's Fees and Expenses, filed Feb. 2, 2006.
Notice of Motion and Motion in Support of Nichols Institute Diagnostics, Inc.'s Memorandum of Points and Authorities in Support of Application for Award of Attorneys' Fees and Expenses, filed Feb. 2, 2006.
Nichols Institute Diagnostics, Inc.'s Memorandum of Points and Authorities in Support of Application for Award of Attorneys' Fees, filed Feb. 2, 2006.
Declaration of April M. Alex in Support of Nichols Institute Diagnostics, Inc.'s Memorandum in Support of Application to Tax Costs, filed Feb. 2, 2006.

Scantibodies' Memorandum of Points and Authorities in Support of Opposition to Nichols' Motion for Prejudgment Interest, filed Feb. 17, 2006.
Consolidated Declaration of Katherine L. Parker in Support of Scantibodies' Oppositions to Nichols' Motions Re 1) Willfulness; 2)Enhanced Damages; and 3) Attorneys' Fees, filed Feb. 17, 2006.
Scantibodies' Memorandum of Points and Authorities in Support of Opposition to Nichols' Motion for Judgment as a Matter of Law Re: Willfulness and in the Alternative for a New Trial, filed Feb. 17, 2006.
Scantibodies' Memorandum of Points and Authorities in Support of Opposition to Nichols' Motion for Application for Award of Attorneys' Fees and Expenses, filed Feb. 17, 2006.
Nichols Institute Diagnostics, Inc.'s Reply in Support of its Application for Award of Attorneys' Fees and Expenses, filed Feb. 27, 2006.
Nichols Institute Diagnostics, Inc.'s Reply Memorandum of Points and Authorities in Support of Motion for Enhancement of Damages, filed Feb. 27, 2006.
Nichols Institute Diagnostics, Inc.'s Reply Motion for Prejudgment Interest, filed Feb. 27, 2006.
Nichols Institute Diagnostics, Inc.'s Reply Motion for Judgment as a Matter of Law Re: Willfulness and in the Alternative for a New Trial, filed Feb. 27, 2006.
Office Action for U.S. Appl. No. 09/344,639 mailed on Sep. 20, 2000.
Petition for Extension of time of Two Months and Amendment for U.S. Appl. No. 09/344,639, dated Feb. 7, 2001.
Declaration of Dr. Ping Gao dated Feb. 7, 2001.
Supplemental Amendment for U.S. Appl. No. 09/344,639 dated Jul. 11, 2001.
Supplemental Amendment Under 37 CFR 1.111 for U.S. Appl. No. 09/344,639 dated May 20, 2002.
Second Supplemental Amendment for U.S. Appl. No. 09/344,639 dated Mar. 18, 2003.
Third Supplemental Amendment for U.S. Appl. No. 09/344,639 dated Mar. 28, 2003.
Notice of Allowability for U.S. Appl. No. 09/344,639 mailed on Apr. 7, 2003.
Interview Summary for U.S. Appl. No. 09/344,639 dated Mar. 11, 2003.
Amendment Under 37 CFR 1.312 for U.S. Appl. No. 09/344,639, dated Jul. 8, 2003.
Comments on Statements of Reasons for Allowance for U.S. Appl. No. 09/344,639, dated Jul. 8, 2003.
Office Communication for U.S. Appl. No. 09/344,639 mailed on Dec. 29, 2003.
Application and Preliminary Amendment for U.S. Appl. No. 10/641,780 filed Aug. 15, 2003.
Second Preliminary Amendment for U.S. Appl. No. 10/641,780 filed Jan. 3, 2006.
Petition to Make Special for U.S. Appl. No. 10/617,489 filed Dec. 30, 2003.
Statement of Substance of Interview for U.S. Appl. No. 10/617,489, filed Nov. 12, 2004.
Office Action for U.S. Appl. No. 10/617,489 mailed on Jan. 24, 2005 for U.S. Appl. No. 10/617,486.
Amendment in Response to Non-Final Office Action for U.S. Appl. No. 10/617,489, filed Mar. 28, 2005.
Supplemental Amendment for U.S. Appl. No. 10/617,489 mailed on Oct. 28, 2005.
Office Action for U.S. Appl. No. 10/617,489 mailed on Dec. 5, 2005.
Amendment in Response to Non-Final Office Action for U.S. Appl. No. 10/617,489, filed Mar. 6, 2006.
Application and Preliminary Amendment for U.S. Appl. No. 10/760,091, filed Jan. 16, 2004.
Application and Preliminary Amendment for U.S. Appl. No. 10/945,608, filed Sep. 20, 2004.
International Preliminary Examination Report for PCT/US00/00855, mailed on Feb. 16, 2001 (WO 00/42437).
Written Opinion for PCT/US04/21896 mailed on Mar. 7, 2005 (WO 05/01843).
PCT Demand and Response to the Written Opinion for PCT/US04/21896, mailed on Jun. 6, 2005 (WO 05/01843).
International Preliminary Report on Patentability for PCT/US04/21896, mailed on Sep. 20, 2005 (WO 05/01843).

Miscellaneous Communication for Reexam Control No. 90/007,412, filed Mar. 1, 2006.
Supplemental Amendment to Reexam Control No. 90/007,412, filed Mar. 7, 2006.
Miscellaneous Communication for Reexam Control No. 90/007,412, filed Mar. 9, 2006.
Receipt stamp from the National Diet Library of Japan showing that the Sep. 1994 issue of the European Journal of Pharmaceutical Sciences was received by the library on Sep. 26, 1995.
Note from the Bibliotheque Interuniversitaire de Pharmacie in Paris indicating that the library received the Sep. 1994 issue of the European Journal of Pharmaceutical Sciences on Sep. 27, 1994.
The copied register received from the Bibliotheque Universitaire Lyon, France indicating that the library received the Sep. 1994 issue of the European Journal of Pharmaceutical Sciences on Sep. 21, 1994.
Appellee Nichols' Brief, filed Mar. 27, 2006.
Appellants Scantibodies' Reply Brief, filed Apr. 21, 2006.
Response to Notice of Defective Paper in Ex Parte Reexamination, mailed on Mar. 14, 2006, in the Reexamination of U.S. Patent No. 6,030,790, Control No. 90/007,412.
Ex Parte Reexamination Interview Summary dated Apr. 20, 2006, in the Reexamination of U.S. Patent No. 6,030,790, Control No. 90/007,412.
Statement of Substance of Interview Under 37 C.F.R. § 1.560(b), dated May 8, 2006, in the Reexamination of U.S. Patent No. 6,030,790, Control No. 90/007,412.
Final Office Action mailed on May 11, 2006, in the Reexamination of U.S. Patent No. 6,030,790, Control No. 90/007,412.
Court Docket from Pacer for *Nichols Institute Diagnostics, Inc.* v. *Scantibodies Clinical Laboratory, Inc.*, from the US District Court for the Southern District of California, docket accessed May 25, 2006.
Court Docket from Pacer for *Nichols Institute Diagnostics, Inc.* v. *Scantibodies Clinical Laboratory, Inc.*, from the US Court of Appeals for the Federal Circuit, docket accessed May 25, 2006.
Court Docket from Pacer for *Scantibodies Laboratory, Inc.*, v. *Immutopics, Inc.*, from the US District Court for the Central District of California, docket accessed May 25, 2006.
Jensen et al., Clinical Chemistry (1996) 42(6):S172 Abstract 320 "Comparing Specificity for Intact Human Parathyroid Hormone Between INCSTAR PTHSP and Nichols Intact PTH Assays".
Magerlein et al., Calcified Tissue International (1995) 56:471 Abstract 193.
Amendment and Reply Under 37 C.F.R. § 1.116, filed Jul. 10, 2006, from the Reexamination of U.S. Patent No. 6,030,790, Control No. 90/007,412.
Court Docket from Pacer for *Nichols Institute Diagnostics, Inc.* v. *Scantibodies Clinical Laboratory, Inc.*, from the US District Court for the Southern District of California, docket accessed Jul. 21, 2006 (for 2006 dates only).
Court Docket from Pacer for *Nichols Institute Diagnostics, Inc.* v. *Scantibodies Clinical Laboratory, Inc.*, from the US Court of Appeals for the Federal Circuit, Case No. 06-1087, docket accessed Jul. 21, 2006.
Court Docket from Pacer for *Nichols Institute Diagnostics, Inc.* v. *Scantibodies Clinical Laboratory, Inc.*, from the US Court of Appeals for the Federal Circuit, Case No. 06-1443, docket accessed Jul. 21, 2006.
Court Docket from Pacer for *Scantibodies Laboratory, Inc.*, v. *Immutopics, Inc.*, from the US District Court for the Central District of California, docket accessed Jul. 21, 2006.
Ex Parte Reexamination Advisory Action, mailed Aug. 3, 2006.
Communication and Request for an Interview, filed Aug. 8, 2006.
Petition for an Extension of Time, filed Aug. 8, 2006.
Statement of Substance of Interview Under 37 CFR § 1.560(b), filed Aug. 9, 2006.
Miscellaneous Communication, filed Aug. 11, 2006.
Court Docket from Pacer for *Nichols Institute Diagnostics, Inc.* v. *Scantibodies Clinical Laboratory, Inc.*, from the US District Court for the Southern District of California, docket accessed Aug. 17, 2006 (for 2006 dates only).

Court Docket from Pacer for *Nichols Institute Diagnostics, Inc.* v. *Scantibodies Clinical Laboratory, Inc.*, from the US Court of Appeals for the Federal Circuit, Case No. 06-1087, docket accessed Aug. 17, 2006.
Court Docket from Pacer for *Nichols Institute Diagnostics, Inc.* v. *Scantibodies Clinical Laboratory, Inc.*, from the US Court of Appeals for the Federal Circuit, Case No. 06-1443, docket accessed Aug. 17, 2006.
Court Docket from Pacer for *Scantibodies Laboratory, Inc.*, v. *Immutopics, Inc.*, from the US District Court for the Central District of California, docket accessed Aug. 17, 2006.
D'Amour, Kidney International (2006) 70:S29-S33.
D'Amour et al., Kidney International (2005) 68:998-1007.
Gardella et al., J. Biol. Chem. (1995) 270:6584-6588.
Huan et al., J. Am. Soc. Nephrol. (2006) 17:1923-1930.
Kunii and Vieira, Braz. J. Med. Biol. Res. (2001) 34(12):1547-1550.
Amendment and Reply Under 37 CFR 1.116 and Statement of Substance of Interview Under 37 CFR § 1.560(b), filed Aug. 16, 2006.
Ex Parte Reexamination Interview Summary, mailed Aug. 16, 2006.
Appellant Nichols Institute of Diagnostics, Inc.'s Opening Brief, US Court of Appeals for the Federal Circuit, Case No. 06-1443, filed Aug. 22, 2006.
Appellant Nichols Institute of Diagnostics, Inc.'s Corrected Opening Brief, US Court of Appeals for the Federal Circuit, Case No. 06-1443, filed Aug. 30, 2006.
Transcription of the Aug. 9, 2006 Oral Argument, US Court of Appeals for the Federal Circuit, Case No. 06-1087.
Petition for Extension of Time, Control No. 90/007,412, filed Sep. 7, 2006.
Statement of Substance of Interview, Control No. 90/007,412, filed Sep. 11, 2006.
Decision Granting Petition for Extension of Time, Control No. 90/007,412, mailed on Sep. 12, 2006.
Decision from the US Court of Appeals for the Federal Circuit, Case No. 06-1087, *Nichols Institute Diagnostics, Inc.*, v. *Scantibodies Clinical Laboratory, Inc., and Scantibodies Laboratory, Inc.*, Decided Sep. 20, 2006.
Decision Merging Reexamination Proceedings Control No. 90/007,685 and 90/007,732, mailed on Feb. 16, 2006.
Office Action in the Reexamination of US Patent No. 6,689,566, Control Nos. 90/007,685 and 90/007,732, mailed on Apr. 20, 2006.
Harlow and Lane, Antibodies: A Laboratory Manual, Cold Spring Harbor (1988) p. 612.
Office Action in Ex Parte Reexamination of US Patent No. 6,689,566, Control Nos. 90/007,685 and 90/007,732, mailed on May 24, 2006.
Ex Parte Reexamination Interview Summary, Jun. 5, 2006.
Ex Parte Reexamination Interview Summary, Jul. 10, 2006.
Amendment in Response to Non-Final Office Action (and Exhibits 1-12 and Replacement Sheet Figure 5), filed in the Ex Parte Reexamination of US Patent No. 6,689,566, Control Nos. 90/007,685 and 90/007,732, filed on Jul. 24, 2006.
Restriction Requirement for U.S. Appl. No. 10/760,091, mailed on Jun. 26, 2006, and Response to Restriction Requirement, filed on Jul. 26, 2006.
Final Office Action for Control No. 90/007,685 and 90/007,732, mailed on Sep. 21, 2006.
Joint Notice of Status of Reexamination of Patent-In-Suit, filed Sep. 29, 2006 in *Scantibodies* v. *Immutopics*, USDC for the Central District of California, Case No. CV 04-8871 GPS (MANx).
Notice of Litigation Activity, submitted by the third party requestor, Oct. 6, 2006.
Ex Parte Reexamination Advisory Action, Control No. 90/007,412, mailed on Sep. 19, 2006.
Miscellaneous Communication—Notice of Concurrent Proceeding, Control No. 90/007,412, filed Sep. 22, 2006.
Ex Parte Reexamination Interview Summary, Control No. 90/007,412, mailed on Oct. 10, 2006.
Notice of Appeal From the Examiner to the Board of Patent Appeals and Interferences, Control No. 90/007,412, filed Oct. 10, 2006.
Order Granting Stay, filed Oct. 12, 2006, US Court of Appeals for the Federal Circuit, Case No. 2006-1443.
Non-Final Office Action, from U.S. Appl. No. 10/641,780, mailed on Oct. 5, 2006.

Statement of Substance of Interview, from U.S. Appl. No. 10/760,091, filed on Oct. 17, 2006.
Result of Consultation, from EP Application No. 00 902 406.8-2404, dated Dec. 19, 2005.
Communication Under Rule 51(4) EPC, from EP Application No. 00 902 406.8-2404, dated Dec. 19, 2005.
Request for correction After IGRA, from EP Application No. 00 902 406.8-2404, dated Apr. 27, 2006.
Documents for Grant, from EP Application No. 00 902 406.8-2404, dated May 24, 2006.
Brief Communication, from EP Application No. 00 902 406.8-2404, dated Jun. 12, 2006.
Receipt of Third Party Observations, from EP Application No. 00 902 406.8-2404, dated Jul. 6, 2006 (and English Translation).
Communication Pursuant to Article 115(2) EPC, from EP Application No. 00 902 406.8-2404, dated Jul. 18, 2006.
Non-Final Office Action, from U.S. Appl. No. 10/617,489, mailed on Oct. 23, 2006.
Rucinski et al., Calcif. Tissue Int. (1995) 56:83-87.
Non-Final Office Action, from U.S. Appl. No. 10/760,091, mailed on Oct. 23, 2006.
Order Denying Petition for Panel Rehearing and Petition for Rehearing En Banc, United States Court of Appeals for the Federal Circuit, *Nichols Institute Diagnostics, Inc.* v. *Scantibodies Clinical Laboratory, Inc., and Scantibodies Laboratory, Inc.*, Case No. 06-1087, order issued on Nov. 20, 2006.
Supplemental Amendment from U.S. Appl. No. 10/617,489, filed Nov. 28, 2006.
Terminal Disclaimer from U.S. Appl. No. 10/617,489, filed Nov. 28, 2006.
Non-Final Office Action from U.S. Appl. No. 10/945,608, mailed on Nov. 15, 2006.
Born et al., Endocrinology (1988) 123(4):1848-1853.
Born et al., Mol. Endocrinol. (1987) 1:5-14.
Bringhurst et al., Am. J. Physiol. (1988) 255(6 Pt 1):E886-93.
Bringhurst et al., Endocrinology (1981) 108:103-108.
Gardella et al., Journal of Biological Chemistry (1991) 266:13141-13146.
Goltzmann et al., Journal of Biological Chemistry (1975) 250:3199-3203.
Horiuchi et al., Am. J. Physiol. (1983) 244(6):E589-95.
Keutmann et al., Endocrinology (1985) 117(3):1230-1234.
Neer et al., J. Clin. Endocrinol. Metab. (1977) 44(2):420-423.
Reeve et al., Br. Med. J. (1980) 280:1340-1344.
Rosenblatt et al., Biochemistry (1981) 20(25):7246-7250.
Rosenblatt et al., Endocrinology (1978) 103(3):978-984.
Segre et al., Endocrinology (1985) 116(3):1024-1029.
Shigeno et al., Journal of Biological Chemistry (1988) 263:3864-3871.
Tregear et al., Endocr. Res. Commun. (1975) 2(8):561-570.
Case concerning petition for revocation of court ruling No. 10406, 2006, Plaintiff's Brief, Nov. 9, 2006 (Japanese litigation document and English translation, requesting withdrawal of the Japanese Patent Office's invalidation of JP Patent No. 3457004).
Written Answer, Nov. 9, 2006 (Japanese litigation document and English translation, requesting withdrawal of the Japanese Patent Office's invalidation of JP Patent No. 3457004).
Description of Evidence, Nov. 9, 2006 (Japanese litigation document and English translation, requesting withdrawal of the Japanese Patent Office's invalidation of JP Patent No. 3457004).
Brief (The first), Nov. 14, 2006 (Japanese litigation document and English translation, requesting withdrawal of the Japanese Patent Office's invalidation of JP Patent No. 3457004).
Notice of Allowance from U.S. Appl. No. 10/617,489, mailed on Jan. 4, 2007.
Amendment in Response to Non-Final Office Action, from U.S. Appl. No. 10/641,780, filed Jan. 5, 2007.
Final Office Action, from the Reexamination of U.S. Patent No. 6,689,566, Control Nos. 90/007,685 and 90/007,732, mailed on Sep. 21, 2006.
Response to Final Office Action from the Reexamination of U.S. Patent No. 6,689,566, Control Nos. 90/007,685 and 90/007,732, filed on Nov. 10, 2006.

Supplemental Response to Final Office Action, from the Reexamination of United States Patent No. 6,689,566, having Control Nos. 90/007,685 and 90/007,732, filed Nov. 20, 2006.
Second Supplemental Response to Final Office Action from the Reexamination of United States Patent No. 6,689,566, having Control Nos. 90/007,985 and 90/007,732, filed Dec. 1, 2006.
Notice of Intent to Issue Ex Parte Reexamination Certificate, from the Reexamination of US Patent No. 6,689,566, Control Nos. 90/007,685 and 90/007,732, mailed Jan. 8, 2007.
Court Docket from Pacer for *Scantibodies Laboratory, Inc.* v. *Immutopics, Inc.*, currently pending at the United States District Court, Central District of California (Western Division), Case No. 2:04-cv-08871-GPS-MAN, docket accessed Jan. 29, 2007.
Decision of the European Patent Office regarding revocation of European Patent No. 0 783 522, dated Jan. 10, 2007.
Amendment in Response to Non-Final Office Action, from U.S. Appl. No. 10/945,608, filed on Feb. 15, 2007.
Amendment in Response to Non-Final Office Action, from U.S. Appl. No. 10/760,091, filed on Mar. 23, 2007.
Gronwald et al., Biol. Chem. (1996) 377:175-186.
Fiskin et al., The Journal of Biological Chemistry (1977) 252:8261-8268.
Pellegrini et al., The Journal of Biological Chemistry (1998) 273:10420-10427.
Non-Final Office Action, from U.S. Appl. No. 09/898,398, mailed on Nov. 12, 2003.
Amendment in Response to Nov. 12, 2003 Office Action, from U.S. Appl. No. 09/898,398, filed on Feb. 12, 2004.
Final Office Action, from U.S. Appl. No. 09/898,398, mailed on Apr. 28, 2004.
Amendment in Response to Apr. 28, 2004 Office Action, from U.S. Appl. No. 09/898,398, filed on Jun. 28, 2004.
Notice of Allowance, from U.S. Appl. No. 09/898,398, mailed on Jul. 19, 2004.
Non-Final Office Action, from U.S. Appl. No. 10/921,368, mailed on Dec. 13, 2004.
Non-Final Office Action, from U.S. Appl. No. 11/146,598, mailed on Dec. 19, 2005.
Non-Final Office Action, from U.S. Appl. No. 11/437,428, mailed on Oct. 16, 2006.
Amendment and Reply Under 37 CFR 1.111. from U.S. Appl. No. 11/437,428, filed on Mar. 16, 2007.
Preliminary Amendment, from U.S. Appl. No. 09/730,174, filed on Jan. 9, 2002.
Restriction Requirement, from U.S. Appl. No. 09/730,174, mailed on Jul. 2, 2002.
Response to Restriction Requirement, from U.S. Appl. No. 09/730,174, filed on Jul. 19, 2002.
Non-Final Office Action, from U.S. Appl. No. 09/730,174, mailed on Oct. 1, 2002.
Amendment, from U.S. Appl. No. 09/730,174, filed on Dec. 19, 2002.
Final Office Action, from U.S. Appl. No. 09/730,174, mailed on Mar. 24, 2003.
Amendment After Final Rejection, from U.S. Appl. No. 09/730,174, filed on Jun. 23, 2003.
Advisory Action, from U.S. Appl. No. 09/730,174, mailed on Jul. 15, 2003.
Amendment & Response to Advisory Action, from U.S. Appl. No. 09/730,174, filed on Aug. 14, 2003.
Non-Final Office Action, from U.S. Appl. No. 09/730,174, mailed on Jun. 15, 2004.
Amendment & Response to Advisory Action, from U.S. Appl. No. 09/730,174, filed on Jun. 30, 2004.
Notice of Allowance, from U.S. Appl. No. 09/730,174, mailed on Sep. 21, 2004.
Restriction Requirement, from U.S. Appl. No. 10/954,695, mailed on Sep. 21, 2005.
Non-Final Office Action, from U.S. Appl. No. 10/954,695, mailed on Dec. 7, 2005.
Amendment, from U.S. Appl. No. 10/954,695, filed on May 30, 2006.
Final Office Action, from U.S. Appl. No. 10/954,695, mailed on Aug. 24, 2006.
RCE and Preliminary Amendment, from U.S. Appl. No. 10/954,695, filed on Oct. 26, 2006.
Non-Final Office Action, from U.S. Appl. No. 10/954,695, mailed on Jan. 3, 2007.
Response to Office Action, from U.S. Appl. No. 10/954,695, filed on Mar. 12, 2007.
Non-Final Office Action, from U.S. Appl. No. 10/998,927, mailed on Dec. 21, 2006.
Response to Office Action, from U.S. Appl. No. 10/998,927, filed on Jan. 2, 2007.
Preliminary Amendment, from U.S. Appl. No. 10/168,185, filed on Mar. 21, 2003.
Restriction Requirement, from U.S. Appl. No. 10/168,185, mailed on Jan. 26, 2006.
Response to Restriction Requirement, from U.S. Appl. No. 10/168,185, filed on Jul. 26, 2006.
Non-Final Office Action, from U.S. Appl. No. 10/168,185, mailed on Oct. 23, 2006.
Examiner Interview Summary, from U.S. Appl. No. 10/168,185, mailed on Feb. 27, 2007.
Final Office Action from U.S. Appl. No. 10/945,608, mailed on May 2, 2007.
Statement of Substance of Interview Under 37 CFR 1.560(b), from Reexamination Control No. 90/007,412, filed on Nov. 8, 2006.
Appeal Brief, from Reexamination Control No. 90/007,412, filed on Dec. 11, 2006.
Examiner's Answer to Appeal Brief, from Reexamination Control No. 90/007,412, filed on Feb. 28, 2007.
Reply Brief, from Reexamination Control No. 90/007,412, filed on Apr. 30, 2007.
Request for Oral Hearing, from Reexamination Control No. 90/007,412, filed on Apr. 30, 2007.
Court Docket from Pacer for *Nichols Institute Diagnostics, Inc.* v. *Scantibodies Clinical Laboratory, Inc.*, from the US District Court for the Southern District of California, docket accessed May 23, 2007.
Court Docket from Pacer for *Nichols Institute Diagnostics, Inc.* v. *Scantibodies Clinical Laboratory, Inc.*, from the US Court of Appeals for the Federal Circuit, Case No. 06-1087, docket accessed May 23, 2007.
Court Docket from Pacer for *Nichols Institute Diagnostics, Inc.* v. *Scantibodies Clinical Laboratory, Inc.*, from the US Court of Appeals for the Federal Circuit, Case No. 06-1443, docket accessed May 23, 2007.
Court Docket from Pacer for *Scantibodies Laboratory, Inc.*, v. *Immutopics, Inc.*, from the US District Court for the Central District of California, docket accessed May 23, 2007.
Non-Final Office Action, from U.S. Appl. No. 10/760,091, mailed on Jun. 15, 2007.
Office Action from Canadian Patent Application No. 2,360,020, mailed on Mar. 12, 2007.
Statement of Substance of Interview, from Control No. 90/007,685 and 90/007,732, filed on Jun. 29, 2007.
Declaration of Julia A. Miller in Support of Nichols Institute Diagnostics, Inc.'s Motion for Leave to File Amended Complaint, filed Jan. 26, 2004.
Nichols Institute Diagnostics, Inc.'s Notice of Lodgement of Corrected Copy of Proposed Second Amended Complaint, Exhibit A to Declaration of Julia A. Miller in Support of Nichols' Jan. 26, 2004 Motion for Leave to File Amended Complaint, filed Feb. 23, 2004.
Declaration of Julia A. Miller in Support of Nichols Institute Diagnostics, Inc.'s Motion for Summary Judgment that the '790 Patent Claims are Valid and Infringed, filed Feb. 28, 2005.
Declaration of M. Andrew Woodmansee in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Declaration of Brigham A. Fordham in Support of Scantibodies' Motion for Judgment on the Pleadings for Lack of Standing and Failure to Join an Indispensable Party or, in the Alternative, to Join a Necessary Party Pursuant to FRCP 19, filed Jul. 16, 2003.
Declaration of Peter R. Munson in Support of Nichols Institute Diagnostics, Inc.'s Opposition to Scantibodies' Motion for Judgment on the Pleadings for Lack of Standing and Failure to Join an Indispensable Party or, in the Alternative, to Join a Necessary Party Pursuant to FRCP 19, filed Sep. 18, 2003.
Declaration of M. Andrew Woodmansee in Support of Scantibodies' Motion for Judgment on the Pleadings for Lack of Standing and Failure to Join an Indispensable Party or, in the Alternative, to Join a Necessary Party Pursuant to FRCP 19, filed Sep. 24, 2003.
Declaration of Julia A. Miller in Support of Nichols Institute Diagnostics, Inc.'s Motion to Permit Service of its Supplemental Amended Complaint Under F.R.C.P. 15(d), filed Nov. 24, 2003.
Declaration of Katherine L. Parker in Support of Scantibodies' Reply to Nichols' Opposition to Motion for Judgment on the Pleadings and for Attorneys' Fees, filed Feb. 23, 2004.
Supplemental Expert Report of Larry W. Evans Pursuant to Rule 26(A)(2)(B), Fed. R. Civ. P.
Supplemental Expert Report of L. J. Deftos, MD, JD, LLM.
Expert Report of Joseph O. Falkinham, III, Ph.D. Adopting Supplemental Expert Report of L. J. Deftos, MD, JD, LLM.
Rebuttal Expert Report of Joseph O. Falkinham, III, Ph.D.
Rubuttal Expert Report of Ellen S. Vitetta, Ph.D.
Order Granting Scantibodies' Ex Parte Application for Leave to File Documents Under Seal, filed May 4, 2005.
Nichols Institute Diagnostics, Inc.'s Notice of and Ex Parte Application for Order to File Its Confidential Consolidated Declaration of April Alex in Support of Nichols' Opposition to Scantibodies' in Limine Motion Nos. 2 and 5 Under Seal, filed May 5, 2005.
Declaration of April Alex in Support of Nichols' Ex Parte Application for Order Sealing Its Confidential Consolidated Declaration of April Alex in Support of Nichols' Opposition to Scantibodies' in Limine Motion Nos. 2 and 5 Under Seal, filed May 5, 2005.
Confidential Consolidated Declaration of April Alex in Support of Nichols Institute Diagnostics, Inc.'s Opposition to Scantibodies' in Limine Motion Nos. 2 and 5, filed May 5, 2005.
Scantibodies' Ex Parte Application For Leave to File Documents Under Seal With Oppositions to Nichols' Motions in Limine, Filed May 5, 2005.
Declaration of Katherine L. Parker in Support of Scantibodies' Ex Parte Application for Leave to File Documents Under Seal, filed May 5, 2005.
Declaration of M. Andrew Woodmansee in Support of Scantibodies' Oppositions to Nichols' Motions in Limine, filed May 5, 2005.
Supplemental Exhibits to Joint Trial Brief [vol. 1 of 5], filed May 4, 2005.
Nichols Institute Diagnostics, Inc.'s Notice of and Ex Parte Application for Order to File Exhibits 12-14, 16-17, 19, 22, 25-26 and 28-33 of the Supplemental Exhibits to Joint Trial Brief Under Seal, filed May 4, 2005.
Declaration of April M. Alex in Support of Nichols' Ex Parte Application for Order to File Exhibits 12-14, 16-17, 19, 22, 25-26 and 28-33 of the Supplemental Exhibits to Joint Trial Brief Under Seal, filed May 4, 2005.
[Proposed] Order Granting Nichols Institute Diagnostics, Inc.'s Ex Parte Application to File Exhibits 12-14, 16-17, 19, 22, 25-26 and 28-33 of the Supplemental Exhibits to Joint Trial Brief Under Seal, filed May 4, 2005.
Deposition of Claude Arnaud, Exhibit No. 12.
Deposition of Thomas Cantor, Exhibit No. 13.
Deposition of Thomas Cantor, Exhibit No. 14.
Deposition of Damon Cook, Exhibit No. 16.
Deposition of Wolf-Georg Forssmann, Exhibit No. 17.
Deposition of Ping Gao, Exhibit No. 19.
Deposition of Thomas Godemeyer, Exhibit No. 22.
Deposition of Markus Magerlein, Exhibit No. 25.
Deposition of Markus Magerlein, Exhibit No. 26.
Deposition of Michael Nordstrom, Exhibit No. 28.
Deposition of K. Ramakrishan, Exhibit No. 29.
Deposition of K. Ramakrishan, Exhibit No. 30.
Deposition of Randall Ringold, Exhibit No. 31.
Deposition of Stephen Scheibel, Exhibit No. 32.
Deposition of Janet Sharp, Exhibit No. 33.
Order Granting Nichols Institute Diagnostics, Inc.'s Ex Parte Application to File the Declaration of James V. Fazio, III in Support of Nichols Institute Diagnostics, Inc.'s Motion in Limine No. 10 to Preclude Counsel From Objecting to Rule 30(B)(6) Designations Under Seal, filed May 4, 2004.
Order Granting Nichols Institute Diagnostics, Inc.'s Ex Parte Application to File Exhibits A, B, C, D, F, G, H, and J to the Consolidated Declaration of April Alex in Support of Nichols Institute Diagnostics, Inc.'s in Limine Motions Nos. 15-17 Under Seal, filed May 4, 2005.
Order Granting Nichols Institute Diagnostics, Inc.'s Ex Parte Application to File Exhibits B and C of the Consolidated Declaration of Jane K. Babin in Support of Nichols Institute Diagnostics, Inc.'s in Limine Motions Nos. 19-20 Under Seal, filed May 4, 2005.
Memorandum of Points and Authorities in Support of Scantibodies' Motion for Summary Judgment of Invalidity and Noninfringement, filed Feb. 18, 2005.
Declaration of Katherine L. Parker in Support of Scantibodies' Motion for Summary Judgment of Invalidity and Noninfringement, with Exhibits 1-39, filed Feb. 18, 2005.
Nichols Institute Diagnostics, Inc.'s Opposition to Motion for Summary Judgment of Invalidity and Non-Infringement, filed Mar. 7, 2005.
Declaration of Julia A. Miller in Support of Nichols Institute Diagnostics, Inc.'s Opposition to Motion for Summary Judgment of Invalidity and Non-Infringement, with Exhibits A-E, filed Mar. 7, 2005.
Declaration of Katherine L. Parker in Support of Scantibodies' Reply Motion for Summary Judgment of Invalidity and Noninfringement, with Exhibits 1-4, filed Mar. 14, 2005.
Deposition of Claude D. Arnaud, taken on Feb. 1, 2005.
Deposition of Gerald Bjorge, taken on Jan. 27, 2005.
Deposition of Thomas Cantor, taken on Aug. 27, 2003.
Deposition of Thomas Cantor (30(B)(6)), taken on Sep. 11, 2003.
Deposition of Damon Cook, taken on Jun. 16, 2003.
Deposition of Damon Cook (30(B)(6)), taken on Sep. 12, 2003.
Deposition of Joseph O. Falkinham, taken on Jan. 21, 2005.
Deposition of Wolf-Georg Forssmann, Ph.D., taken on Aug. 25, 2003.
Deposition of Ping Gao, M.D., taken on Jun. 18, 2003.
Deposition of Allen Garrett, taken on May 20, 2005.
Deposition of Thomas Godemeyer, taken on Oct. 6, 2004.
Deposition of Mark Gray, taken on Jun. 16, 2003.
Deposition of Dr. Richard Lerner, taken on Jan. 13, 2005.
Deposition of Dr. Richard Lerner, taken on Mar. 16, 2005.
Deposition of Markus Magerlein, Ph.D., taken on May 28, 2003.
Deposition of Markus Magerlein, Ph.D., taken on Aug. 10, 2004.
Deposition of Michael Nordstrom (30(B)(6)), taken on Sep. 17, 2003.
Deposition of K. Ramakrishan, Ph.D., (30(B)(6)), taken on Aug. 13, 2003.
Deposition of K. Ramakrishan, Ph.D., (30(B)(6)), taken on Sep. 3, 2003.
Deposition of Stephen Scheibel, taken Aug. 8, 2003.
Deposition of Janet Sharp, taken on Aug. 19, 2003.
Deposition of Randolph Wall, taken Jan. 31, 2005.
Deposition of J. Stuart Woodhead, taken Jan. 18, 2005.
Deposition of Zan Yang, Ph.D., taken on Jun. 16, 2003.
Nichols Institute Diagnostics, Inc.'s Notice of and Ex Parte Application for Order to File Its Consolidated Confidential Declaration of April M. Alex in Support of (1) Nichols Institute Diagnostics, Inc.'s Motion for Judgment as a Matter of Law Re: Willfulness and in the Alternative for a New trial and (2) Nichols Institute Diagnostics, Inc.'s Motion for Enhanced Damages Under Seal, filed Jan. 27, 2006.
Consolidated Confidential Declaration of April M. Alex in Support of (1) Nichols Institute Diagnostics, Inc.'s Motion for Judgment as a Matter of Law Re: Willfulness and in the Alternative for a New trial and (2) Nichols Institute Diagnostics, Inc.'s Motion for Enhanced Damages, filed Jan. 27, 2006.
[Proposed] Order Granting Nichols Institute Diagnostics, Inc.'s Ex Parte Application to File Its Consolidated Confidential Declaration of April M. Alex in Support of (1) Nichols Institute Diagnostics, Inc's Motion for Judgement as a Matter of Law Re: Willfulness and in the Alternative for a New Trial and (2) Nichols Institute Diagnostics, Inc's Motion For Enhanced Damages Under Seal, filed Jan. 27, 2006, order signed Judge Brewster Jan. 31, 2006.
Confidential Deposition of Tom Cantor, taken on Jul. 11, 2005.

Declaration of Thomas L. Cantor with Exhibit A, executed on Apr. 7, 2005.
Advisory Action from U.S. Appl. No. 10/945,608, mailed on Jul. 23, 2007.
Restriction Requirement from U.S. Appl. No. 10/799,476, mailed on Jan. 10, 2007.
Response to Restriction Requirement from U.S. Appl. No. 10/799,476, filed Jan. 24, 2007.
Non-Final Office Action from U.S. Appl. No. 10/799,476, mailed on Apr. 17, 2007.
Restriction Requirement from U.S. Appl. No. 10/265,276, mailed on Aug. 20, 2004.
Response to Restriction Requirement from U.S. Appl. No. 10/265,276, filed on Dec. 18, 2004.
Non-Final Office Action from U.S. Appl. No. 10/265,276, mailed on Jan. 24, 2005.
Amendment in Response to Non-Final Office Action from U.S. Appl. No. 10/265,276, filed on Apr. 25, 2005.
Non-Final Office Action from U.S. Appl. No. 10/265,276, mailed on Jun. 28, 2005.
Amendment in Response to Non-Final Office Action from U.S. Appl. No. 10/265,276, filed on Oct. 7, 2005.
Final Rejection from U.S. Appl. No. 10/265,276, mailed on Jan. 4, 2006.
Amendment After Final Action (37 CFR Section 1.116) from U.S. Appl. No. 10/265,276, filed on Apr. 4, 2006.
Advisory Action from U.S. Appl. No. 10/265,276, mailed on May 18, 2006.
Pre-Appeal Brief Request for Review from U.S. Appl. No. 10/265,276, filed on Jun. 13, 2006.
Notice of Panel Decision from Pre-Appeal Brief Review from U.S. Appl. No. 10/265,276, mailed on Aug. 4, 2006.
Non-Final Office Action from U.S. Appl. No. 10/265,276, mailed on Oct. 20, 2006.
Amendment in Response to Non-Final Office Action from U.S. Appl. No. 10/265,276, filed on Jan. 19, 2007.
Final Rejection from U.S. Appl. No. 10/265,276, mailed on Apr. 19, 2007.
Restriction Requirement from U.S. Appl. No. 10/674,294, mailed on Jun. 2, 2006.
Response to Restriction Requirement from U.S. Appl. No. 10/674,294, filed on Jun. 28, 2006.
Non-Final Office Action from U.S. Appl. No. 10/674,294, mailed on Sep. 11, 2006.
Amendment in Response to Non-Final Office Action from U.S. Appl. No. 10/674,294, filed on Dec. 13, 2006.
Final Rejection from U.S. Appl. No. 10/674,294, mailed on Feb. 15, 2007.
Amendment After Final Action Under 37 CFR 1.116 from U.S. Appl. No. 10/674,294, filed on Apr. 13, 2007.
Advisory Action from U.S. Appl. No. 10/674,294, mailed on Apr. 27, 2007.
Examiner Interview Summary from U.S. Appl. No. 10/674,294, mailed on May 17, 2007.
Amendment After Final Action Under 37 CFR 1.116 from U.S. Appl. No. 10/674,294, filed on May 18, 2007.
Substance of Examiner Interview from U.S. Appl. No. 10/674,294, filed on Jun. 14, 2007.
Non-Final Office Action from U.S. Appl. No. 10/674,294, mailed on Jun. 18, 2007.
Restriction Requirement from U.S. Appl. No. 10/958,541, mailed on Mar. 7, 2007.
Response to Restriction Requirement from U.S. Appl. No. 10/958,541, filed on Apr. 4, 2007.
Non-Final Office Action from U.S. Appl. No. 10/958,541, mailed on Aug. 3, 2007.
Restriction Requirement from U.S. Appl. No. 11/516,912, mailed on Jul. 31, 2007.
Canfield et al., Endocrinology (1982) 110(5):1555-1563.
Motte et al., Journal of Immunology (1987) 138(10):3332-3338.
Kuriyama et al., Blood Purification (1998) 16:43-48.
Monier-Faugere et al., Journal of the American Society of Nephrology (1999) 11:1093-1099.
Nissenson et al., J. Biol. Chem. (1988) 263(26):12866-12871.
Parthemore et al., J. Clin. Endocrinol. Metab. (1978) 47(2):284-289.
Podbesek et al., Endocrinology (1983) 112:1000-1006.
Richards et al., Clin. Nephrol. (1999) 51(2):126-127.
Stafford-Johnson et al., J. Comput. Assist. Tomogr. (1998) 22(2):295-299.
Stewart et al., J. Clin. Invest. (1988) 81(2):596-600.
Thompson et al., PNAS USA (1988) 85(15):5673-5677.
Yates et al., J. Clin. Invest. (1988) 81(3):932-938.
Bhaskaran and Ponnuswamy, Int. J. Pept. Protein Res. (1988) 32:242-255.
D'Amour et al., Endocrinology (1985) 117:127-134.
D'Amour et al., J. Immunoassay (1989) 10:191-205.
Deleage and Roux, Protein Engineering (1987) 1:289-294.
Ghillani et al., Cancer Res. (1989) 49(23):6845-6851.
Henikoff et al., PNAS USA (1992) 89:10915-10919.
Hopp and Woods, PNAS USA (1981) 78:3824-3828.
Janin, Nature (1979) 277:491-492.
Kyte and Doolittle, J. Mol. Biol. (1982) 157:105-132.
Lei et al., J. Biol. Chem. (1995) 270(20):1182-1186.
Loveridge et al., Endocrinology (1991) 128(4):1938-1946.
Merrifield et al., Biochemistry (1982) 21:5020.
Niall et al., PNAS USA (1969) 64:771-778.
Rabbani et al., J. Biol. Chem. (1984) 259:2949-2955.
Stevens et al., Journal of Immunological Methods (1988) 108:271-278.
Stryer, (ed.), Biochemistry $2^{nd}$ ed., (1981) pp. 13-16.
Janeway et al., Immunobiology, $5^{th}$ ed., Appendix I, pp. 624-625.
Berson et al., J. Clin. Invest. (1956) 35:170-190.
Berson et al., PNAS USA (1963) 49:613-617.
Broadus et al., J. Clin. Invest. (1977) 60:771-783.
Brossard et al., J. Bone and Miner. Res. (1999) 14:S444.
Canterbury et al., J. Clin. Invest. (1975) 55:1245-1253.
Dambacher et al., Clinical Science (1979) 57:435-443.
Endres et al., Kidney International (1982) 21:132.
Flueck et al., Proceedings of the 58th American Meeting of the Endocrine Society, Jun. 1976.
Freitag et al., New England Journal of Medicine (1978) 298:29-32.
Gallagher et al., J. Lab. Clin. Med. (1980) 95:373-385.
Habener and Potts, New England Journal of Medicine (1978) 299:580-585, 635-644.
Kao et al., Clin. Chem. (1982) 28:69-74.
Keutmann et al., Biochemistry (1978) 17:5723-5729.
Lafferty, Medicine (1966) 45:247-260.
Mallette et al., J. Clin. Endocrinology Metab. (1982) 54:1017-1024.
Mallette, Ligand Review (1979) 1:18-19.
Nussbaum et al., Clin. Chem. (1988) 33(8):1364-1367.
Raisz et al., Annals International Medicine (1979) 91:739-740.
Rodbard and Hutt, "Statistical Analysis of Radioimmunoassays and Immunoradiometric (labeled antibody) Assays" in Assays, Radioimmunoassays and Related Procedures in Medicine, vol. 1, Vienna: International Atomic Energy Agency, Vienna, (1974) pp. 165-192.
Rodbard et al., J. Clin. Endocrinology Metab. (1968) 28:1412-1418.
Roos et al., J. Clin. Endocrinology and Metab. (1981) 53:709-721.
Segre et al., American Journal of Medicine (1974) 56:774-784.
Segre et al., Biochemistry (1977) 16:2417-2427.
Segre et al., J. Clin. Invest. (1981) 67:439-448.
Segre et al., J. Clin. Invest. (1981) 67:449-457.
Segre et al, J. Clin. Invest. (1972) 51:3163-3172.
Silverman and Yalow, J. Clin. Invest. (1973) 52:1958-1971.
Slatopolsky et al., Journal of American Society of Nephrology (1999) 10:625A.
Travis, (ed.), "Clinical Radioimmunoassay" in State-of-the-Art Scientific Newsletter, Inc., Anaheim, CA 92803, (1980) pp. 13-16.
Wood et al., J. Clin. Chem. Biochemistry (1980) 18:789-795.
Request for Continued Examination from U.S. Appl. No. 10/945,608, filed on Aug. 2, 2007.
Non-Final Office Action from U.S. Appl. No. 11/437,428, mailed on Jun. 6, 2007.
Amendment in Response to Non-Final Office Action from U.S. Appl. No. 10/760,091, filed Sep. 17, 2007.
Aka et al., International Journal of Adolescent Medicine and Health (2000) 12(4):331-335.

Cavaco et al., Journal of Endocrinological Investigation (1999) 22(11):829-834.
Corbetta et al., Clinical Endocrinology (2000) 52(3):339-348.
Fujimori et al., Endocrinology (1992) 130:29-36.
Harvey et al., Journal of Biological Chemistry (1999) 274(33):23249-23255.
Jara et al., Journal of Bone and Mineral Research (1994) 9(10):1629-1633.
Mittal et al., Kidney International (1999) 55(5):1912-1919.
Schultz et al., Bone and Mineral (1994) 27:121-132.
Schultz et al., Journal of Bone and Mineral Research (1993) 8(Supp. 1):S202.
Takano et al., Acta Endocrinologica (1988) 118:551-558.
Tam et al., PNAS USA (1988) 85(15):5409-5413.
Zahradnik et al., Clinical Chemistry (1986) 32(6):1154.
Response to the Grounds of Appeal, from Opposition to EP 0 783 522, filed Oct. 9, 2007.
Declaration of Hans H. Linden (D22), dated Oct. 9, 2007.
Concession Report for 1994 of the Dutch Mailing Service KPN (D23).
Non-Final Office Action from U.S. Appl. No. 10/945,608, mailed on Oct. 16, 2007.
Sukovaty et al., Journal of Pharmaceutical and Biomedical Analysis (2006) 42:261-271.
Amendment and Reply Under 37 CFR 1.111 from U.S. Appl. No. 11/437,428, filed on Nov. 6, 2007.
Memorandum of Points and Authorities in Support of Plaintiff's Motion for Partial Summary Judgment on Defendants' Counterclaim of Patent Invalidity Under 35 U.S.C. §§ 102 and 103, filed Nov. 14, 2007.
Plaintiff's Statement of Uncontroverted Facts and Conclusions of Law in Support of Its Motion for Partial Summary Judgment on Defendants' Counterclaim of Patent Invalidity Under 35 U.S.C. §§ 102 and 103, filed Nov. 14, 2007.
Declaration of Brian W. Kasell in Support of Plaintiff's Motion for Partial Summary Judgment on Defendants' Counterclaim of Patent Invalidity Under 35 U.S.C. §§ 102 and 103, filed Nov. 14, 2007.
U.S. Appl. No. 09/231,422, filed Jan. 14, 1999.
Office Action from U.S. Appl. No. 09/231,422, mailed on Sep. 20, 2000.
Amendment from U.S. Appl. No. 09/231,422, filed on Feb. 7, 2001.
Supplemental Amendment from U.S. Appl. No. 09/231,422, filed on Jul. 11, 2001.
Supplemental Amendment Under 37 C.F.R. § 1.111 from U.S. Appl. No. 09/231,422, filed on May 20, 2002.
Amendment Under 37 C.F.R. § 1.111 from U.S. Appl. No. 09/231,422, filed on Jan. 14, 2003.
Notice of Allowance and Interview Summary from U.S. Appl. No. 09/231,422, mailed on Feb. 12, 2003.
Amendment Under 37 C.F.R. § 1.312 from U.S. Appl. No. 09/231,422, filed on May 2, 2003.
Comments on Statements of Reasons for Allowance from U.S. Appl. No. 09/231,422, filed on May 2, 2003.
Response to Rule 312 Communication from U.S. Appl. No. 09/231,422, mailed on Dec. 5, 2003.
Statement of Substance of Interview from Reexamination Control No.'s 90/007,685 and Control No. 90/007,732, filed Nov. 26, 2007.
Miscellaneous Communication from Reexamination Control No. 90/007,685 and 90/007,732, mailed on Nov. 30, 2007.
Final Office Action from U.S. Appl. No. 10/760,091, mailed on Dec. 13, 2007.
Moreau et al., Bioinformatics (2006) 22:1088-1095.
Regenmortel et al., Methods in Enzymology (1996) 9:465-472.
Communication of a Notice of Opposition against EP Patent No. 1 151 307, dated Dec. 3, 2007.
Memorandum of Points and Authorities in Support of Plaintiff's Opposition to Defendants' Motion for Summary Judgment of Patent Invalidity for Lack of Enablement, filed Dec. 18, 2007.
Memorandum of Points and Authorities in Support of Plaintiff's Opposition to Defendants' Motion for Summary Judgment of Patent Invalidity for Violation of On Sale Bar and for Obviousness Over the Prior Art, filed Dec. 18, 2007.
Memorandum of Points and Authorities in Support of Plaintiff's Opposition to Defendants' Motion for Summary Judgment for Failing to Disclose the Best Mode, filed Dec. 18, 2007.
Declaration of Brian W. Kasell in Support of Plaintiff's Oppositions to Defendants' Summary Judgment Motions for: 1. Failing to Disclose the Best Mode; 2. Violation of On Sale Bar and for Obviousness; 3. Lack of Enablement; and 4. Non-Infringement, filed Dec. 18, 2007.
Declaration of Thomas L. Cantor in Support of Plaintiff's Opposition to Defendants' Motions for Summary Judgment, filed Dec. 18, 2007.
Plaintiff's Statement of Genuine Issues of Material Fact in Support of its Opposition to Defendants' Motion for Summary Judgment of Patent Invalidity for Violation of On Sale Bar and Obviousness Over the Prior Art, filed Dec. 18, 2007.
Plaintiff's Statement of Genuine Issues of Material Fact in Support of its Opposition to Defendants' Motion for Summary Judgment of Patent Invalidity for Lack of Enablement, filed Dec. 18, 2007.
Plaintiff's Statement of Genuine Issues of Material Fact in Support of its Opposition to Defendants' Motion for Summary Judgment for Failing to Disclose the Best Mode, filed Dec. 18, 2007.
Order Denying Scantibodies' Motion for Partial Summary Judgment on Defendants' Counterclaim of Patent Invalidity, filed Dec. 28, 2007.
Plaintiff's Amendment to Statement of Genuine Issues of Material Fact in Support of its Opposition to Defendants' Motion for Summary Judgment for Failing to Disclose the Best Mode, filed Jan. 30, 2008.
Immutopics' Response to Plaintiff's Amendment to Statement of Genuine Issues of Material Fact in Support of its Opposition to Defendants' Motion for Summary Judgment for Failing to Disclose the Best Mode and Request for Sanctions, filed Jan. 31, 2008.
Petition to Withdraw Application from Issue Pursuant to 37 CFR 1.313(c)(2) and Preliminary Amendment, from U.S. Appl. No. 10/617,489, filed on Jan. 25, 2008.
Communication of a Notice of Opposition against EP Patent No. 1 151 307, dated Dec. 3, 2007 (with Briefing Paper—Opposition Proceedings at the EPO English translation).
Joint Statement of Contentions Re Meaning of Terms in Reexamination Claims of U.S. Patent No. 6,689,566; Proposed Schedule Re Markman Hearing, filed Feb. 11, 2008.
Plaintiff's Ex Parte Application Regarding Handling and Use of Documents Filed Under Seal; Memorandum of Points and Authorities; Declaration of Brian W. Kasell, filed Feb. 12, 2008.
[Corrected] Plaintiff's Ex Parte Application Regarding Handling and Use of Documents Filed Under Seal; Memorandum of Points and Authorities; Declaration of Brian W. Kasell, filed Feb. 12, 2008.
Defendants' Opposition Memorandum to Plaintiff's Ex Parte Application Regarding Handling and Use of Documents Filed Under Seal, filed Feb. 12, 2008.
Declaration of Matthew A. Newboles in Support of Defendants' Opposition to Plaintiff's Ex Parte Application Regarding Handling and Use of Documents Filed Under Seal, filed Feb. 12, 2008.
Plaintiff's Response to Defendants' Opposition to Plaintiff's Ex Parte Application Regarding Handling and Use of Documents Filed Under Seal; Supplemental Declaration of Brian W. Kasell, filed Feb. 13, 2008.
Statement of Substance of Interview, from U.S. Appl. No. 10/617,489, filed on Feb. 26, 2008.
Statement of Substance of Interview, from U.S. Appl. No. 10/617,489, filed on Mar. 6, 2008.
Response to Final Office Action from the Reexamination of U.S. Patent No. 6,689,566, Control Nos. 90/007,685 and 90/007,732, filed on Nov. 10, 2006.
Decision on Petition from the Reexamination of U.S. Patent No. 6,689,566, Control Nos. 90/007,685 and 90/007,732, mailed on Feb. 11, 2008.
Decision Returning Papers from the Reexamination of U.S. Patent No. 6,689,566, Control Nos. 90/007,685 and 90/007,732, mailed on Feb. 11, 2008.
Statement of Substance of Interview from the Reexamination of U.S. Patent No. 6,689,566, Control Nos. 90/007,685 and 90/007,732, filed on Mar. 6, 2008.
English Translation of Opposition Documents, Opposition to European Patent No. EP 1 151 307 B1, dated Nov. 19, 2007.

Minutes (Decision) from the Supreme Judicial Court of Japan, 2007 Case # 333 and 371, dated Feb. 5, 2008 (with English translation).
Habener et al., Nature New Biology (1972) 238:152-154.
Immutopics, Inc. and Immutopics International, LLC's Claim Construction Brief, filed Mar. 19, 2008.
Declaration of Matthew A. Newboles in Support of Immutopics, Inc. and Immutopics International, LLC's Claim Construction Brief, filed Mar. 19, 2008.
Plaintiff's Brief in Support of Construction of Terms in Reexamination Claims of U.S. Patent No. 6,689,566, filed Mar. 19, 2008.
Declaration of Brian W. Kasell in Support of Plaintiff's Brief in Support of Construction of Terms in Reexamination Claims of U.S. Patent No. 6,689,566, filed Mar. 19, 2008.
Declaration of Monica Ranes-Goldberg, Ph.D., filed Mar. 19, 2008.
Tizard, Immunology, An Introduction (Saunders College Publishing) $3^{rd}$ ed. (1992) p. 17.
Rich et al., Clinical Immunology Principles and Practice (Mosby) ($2^{nd}$ ed. 2001) at 14.4.
Notice of Allowance and Examiner Interview Summary from U.S. Appl. No. 10/617,489, mailed on Apr. 4, 2008.
Non-Final Office Action, from U.S. Appl. No. 11/437,428, mailed on Jun. 6, 2007.
Amendment and Reply Under 37 CFR 1.111, from U.S. Appl. No. 11/437,428, filed on Nov. 6, 2007.
Final Office Action, from U.S. Appl. No. 11/437,428, mailed on Jan. 25, 2008.
Amendment in Response to Non-Final Office Action, from U.S. Appl. No. 10/168,185, filed on Apr. 23, 2007.
Final Office Action, from U.S. Appl. No. 10/168,185, mailed on Jul. 25, 2007.
Amendment After Final Action Under 37 C.F.R. 1.116, from U.S. Appl. No. 10/168,185, filed on Jan. 25, 2008.
Advisory Action, from U.S. Appl. No. 10/168,165, mailed on Apr. 1, 2008.
Supplemental Response to Office Action, from U.S. Appl. No. 10/954,695, filed on Apr. 18, 2007.
Final Office Action, from U.S. Appl. No. 10/954,695, mailed on Jul. 27, 2007.
Request for Continued Examination, from U.S. Appl. No. 10/954,695, filed on Jan. 4, 2008.
Non-Final Office Action, from U.S. Appl. No. 10/954,695, mailed on Feb. 28, 2008.
Notice of Allowance, from U.S. Appl. No. 10/998,927, mailed on Apr. 3, 2007.
Decision on Petition, from U.S. Appl. No. 90/007,685 and 90/007,732, mailed on Apr. 3, 2008.
Court Docket From Pacer for *Scantibodies Laboratory, Inc.* v. *Immutopics, Inc.*, currently pending at the United States District Court for the Central District of California (Western Division), Case No. CV 04-08871 MRP (MANx), docket accessed Apr. 16, 2008.
Amendment in Response to Non-Final Office Action, from U.S. Appl. No. 10/945,608, filed Apr. 16, 2008.
Declaration of Interference, between U.S. Appl. No. 10/641,780 and U.S. Patent No. 6,838,264, Patent Interference No. 105,575 (MPT), mailed on Aug. 30, 2007.
Cantor Power of Attorney and Designation of Lead and Backup Counsel, filed Sep. 12, 2007.
Cantor Notice of Related Proceedings, filed Sep. 12, 2007.
Cantor Notice of Real Party-in-Interest, filed Sep. 12, 2007.
Cantor Request for File Copies, filed Sep. 12, 2007.
Cantor Clean Copy of Claims, filed Sep. 12, 2007.
Zahradnik Power of Attorney and Designation of Lead Counsel, filed Sep. 13, 2007.
Zahradnik Notice of Related Proceedings, filed Sep. 13, 2007.
Zahradnik Notice of Lead and Backup Counsel, filed Sep. 13, 2007.
Zahradnik Notice of Real Party-in-Interest, filed Sep. 13, 2007.
Zahradnik Request for File Copies, filed Sep. 13, 2007.
Zahradnik Clean Copy of Claims, filed Sep. 13, 2007.
Order Authorizing Copies of Office Records, filed Sep. 18, 2007.
Cantor Annotated Copy of Claims, filed Sep. 26, 2007.
Zahradnik Substitute Clean Copy of Claims, filed Sep. 27, 2007.
Zahradnik Annotated Copy of Claims, filed Sep. 27, 2007.
Notice to the Board Re: Incomplete Copy of Files, filed Oct. 9, 2007.
Cantor List of Intended Motions, filed Oct. 11, 2007.
Zahradnik List of Motions, filed Oct. 11, 2007.
Order Motion Times—Bd.R. 104(c), from Patent Interference No. 105,575 (MPT), filed Oct. 22, 2007.
Joint Stipulation Extending Time Periods 1 and 2, from Patent Interference No. 105,575 (MPT), filed Nov. 19, 2007.
Joint Statement Regarding Settlement Discussions, from Patent Interference No. 105,575 (MPT), filed Nov. 30, 2007.
Cantor Exhibit List and Exhibits, filed Dec. 14, 2007.
Cantor Substantive Motion 1—Motion for Benefit to Priority Applications, filed Dec. 14, 2007.
Cantor Substantive Motion 2—Motion to Change the Count, filed Dec. 14, 2007.
Cantor Substantive Motion 3—Motion to Correct Inventorship, filed Dec. 14, 2007.
Notice of Request to Correct Inventorship, filed Dec. 14, 2007.
Notice of Filing Cantor Priority Statement, filed Dec. 14, 2007.
Notice of Filing of Zahradnik Priority Statement, filed Dec. 14, 2007.
Zahradnik List of Exhibits and Exhibits, filed Dec. 14, 2007.
Zahradnik Substantive Motion 1 (Motion for Judgment Under 35 U.S.C. § 135(b)), filed Dec. 14, 2007.
Zahradnik Substantive Motion 2 (Judgment for No Interference in Fact), filed Dec. 14, 2007.
Zahradnik Substantive Motion 3 (Judgment for Lack of Written Description), filed Dec. 14, 2007.
Zahradnik Substantive Motion 4 (Judgment for Lack of Enablement), filed Dec. 14, 2007.
Cantor Contingent Responsive Motion 1, Contingent Motion to Substitute Claim 47 for Claims in Interference, filed Jan. 18, 2008.
Deposition of J. Stuart Woodhead, Ph.D., taken on Feb. 21, 2008.
Deposition of J. Scott Hutchison, Ph.D., taken on Feb. 15, 2008.
Deposition of Thomas L. Cantor, taken on Feb. 8, 2008.
Cantor Opposition 1 (Opposition to Motion for Judgment Under 35 U.S.C. § 135(b)), Patent Interference No. 105,575 (MPT), filed Mar. 21, 2008.
Cantor Opposition 2 (Opposition to Motion for Judgment of No Interference-in-Fact), Patent Interference No. 105,575 (MPT), filed Mar. 21, 2008.
Cantor Opposition to Zahradnik Motion 3, Judgment for Lack of Written Description, Patent Interference No. 105,575 (MPT), filed Mar. 21, 2008.
Cantor Opposition to Zahradnik Motion 4, Judgment for Lack of Enablement, Patent Interference No. 105,575 (MPT), filed Mar. 21, 2008.
Cantor Exhibit List and Exhibits, Patent Interference No. 105,575 (MPT), filed Mar. 21, 2008.
Supplemental Affidavit of J. Stuart Woodhead, Ph.D., dated Mar. 19, 2008.
Zahradnik Opposition 1 (Opposition to Cantor Substantive Motion 1—Motion for Benefit to Priority Applications), Patent Interference No. 105,575 (MPT), filed Mar. 21, 2008.
Zahradnik Opposition 2 (Opposition to Cantor Substantive Motion 2 to Change the Count), Patent Interference No. 105,575 (MPT), filed Mar. 21, 2008.
Zahradnik Opposition 3 (Opposition to Cantor Contingent Responsive Motion—Contingent Motion to Substitute Claim 47 for Claims in Interference), Patent Interference No. 105,575 (MPT), filed Mar. 21, 2008.
Zahradnik List of Exhibits as of Mar. 21, 2008, Patent Interference No. 105,575 (MPT), filed Mar. 21, 2008.
Declaration of J. Scott Hutchison, dated Mar. 20, 2008.
Cantor Reply 1 (In Support of Motion for Benefit to Priority Applications) from Patent Interference No. 105,575 (MPT), filed May 19, 2008.
Cantor Reply 2 (In Support of Motion to Change the Count) from Patent Interference No. 105,575 (MPT), filed May 19, 2008.
Cantor Reply 3 In Response to Zahradnik Opposition 3 (In Support of Cantor Contingent Responsive Motion 1 to Substitute Claim 47 for Claims in Interference) from Patent Interference No. 105,575 (MPT), filed May 19, 2008.
Zahradnik List of Exhibits as of May 19, 2008 from Patent Interference No. 105,575 (MPT), filed May 19, 2008.

Zahradnik Reply 1 (Reply to Cantor Opposition to Zahradnik Motion 1—§ 135(b)) from Patent Interference No. 105,575 (MPT), filed May 19, 2008.
Zahradnik Reply 2 (Reply to Cantor Opposition to Zahradnik Motion 2—No Interference-In-Fact) from Patent Interference No. 105,575 (MPT), filed May 19, 2008.
Zahradnik Reply 3 (Reply to Cantor Opposition to Zahradnik Motion 3—Written Description) from Patent Interference No. 105,575 (MPT), filed May 19, 2008.
Zahradnik Reply 4 (Reply to Cantor Opposition to Zahradnik Motion 4—Enablement) from Patent Interference No. 105,575 (MPT), filed May 19, 2008.
Zahradnik Service of Demonstrative Exhibits, Patent Interference No. 105,575 (MPT), Jul. 16, 2008.
Cantor Service of Demonstrative Exhibits, Patent Interference No. 105,575 (MPT), Jul. 16, 2008.
Order—Bd. R. 104 Regarding Demonstrative Aids, Patent Interference No. 105,575 (MPT), filed Jul. 24, 2008.
Patentee's Response to Grounds of Opposition, EP Patent No. 1 151 307, dated Jul. 14, 2008.
Affidavit of J. Stuart Woodhead, Ph.D., FRC.Path., dated Dec. 13, 2007.
"Assays for Antibody Production" in Current Protocols in Immunology, (1991) section 2.1.
Notice of Allowance and Examiner's Amendment from U.S. Appl. No. 10/945,608, mailed on Jul. 23, 2008.
Claim Construction Order from *Scantibodies Laboratory, Inc.*, v. *Immutopics, Inc.*, filed May 1, 2008.
Order Granting Immutopics' Motion for Summary Judgment of Non-Infringement of the '566 Patent; Denying Immutopics' Motions for Summary Judgment Based on Invalidity of the '566 Patent, filed May 16, 2008.
Plaintiff's Notice of Motion and Motion for Relief Under Protective Order Regarding Confidential Information, filed Jul. 11, 2008.
Rule 37 Joint Stipulation Re Plaintiff's Motion for Relief Under Protective Order Regarding Confidential Information, filed Jul. 11, 2008.
Declaration of Brian W. Kasell in Support of Rule 37 Joint Stipulation Re Plaintiff's Motion for Relief Under Protective Order Regarding Confidential Information, filed Jul. 11, 2008.
Declaration of Matthew A. Newboles in Support of Defendants' and Counterclaimants' Opposition to Joint Stipulation Re Plaintiff's Motion for Relief Under Protective Order Regarding Confidential Information, filed Jul. 11, 2008.
Minutes of Status Conference, filed Jul. 18, 2008.
Plaintiff's Supplemental Memorandum in Support of Its Motion for Relief Under Protective Order Regarding Confidential Information, filed Jul. 22, 2008.
Judgment, filed Jul. 30, 2008.
Report on the Determination of an Action Regarding a Patent or Trademark, filed Jul. 31, 2008.
Court Docket From Pacer for *Scantibodies Laboratory, Inc.* v. *Immutopics, Inc.*, currently pending at the United States District Court for the Central District of California (Western Division), Case No. CV 04-08871 MRP (MANx), docket accessed Aug. 4, 2008.
Non-Final Office Action from U.S. Appl. No. 11/799,726, mailed on Apr. 28, 2008.
Campbell et al., Laboratory Techniques in Biochemistry and Molecular Biology (1986) vol. 13, pp. 1-19.
Amendment in Response to Non-Final Office Action from U.S. Appl. No. 10/799,476, filed Aug. 29, 2007.
Final Office Action from U.S. Appl. No. 10/799,476, mailed on Nov. 6, 2007.
Request for Continued Examination and Amendment from U.S. Appl. No. 10/799,476, filed Mar. 6, 2008.
Final Office Action from U.S. Appl. No. 10/799,476, mailed on Apr. 21, 2008.
Notice of Appeal and Reasons for Requesting Pre-Appeal Brief Review from U.S. Appl. No. 10/265,276, filed Oct. 10, 2007.
Notice of Decision from Pre-Appeal Brief Review from U.S. Appl. No. 10/265,276, mailed on Nov. 30, 2007.
Amendment in Response to Non-Final Office Action from U.S. Appl. No. 10/674,294, filed Sep. 17, 2007.

Non-Final Office Action from U.S. Appl. No. 10/674,294, mailed on Nov. 29, 2007.
Amendment in Response to Non-Final Office Action from U.S. Appl. No. 10/674,294, filed Apr. 29, 2008.
Response to Restriction Requirement from U.S. Appl. No. 11/516,912, filed Sep. 19, 2007.
Non-Final Office Action from U.S. Appl. No. 11/516,912, mailed on Nov. 13, 2007.
Amendment in Response to Non-Final Office Action from U.S. Appl. No. 11/516,912, filed May 13, 2008.
Statement of Substance of Interview from U.S. Appl. No. 10/617,489, filed May 15, 2008.
Statement of Substance of Interview from U.S. Appl. No. 90/007,685 and U.S. Appl. No. 90/007,732, filed May 15, 2008.
Amendment After Final Action Under 37 C.F.R. 1.116 from U.S. Appl. No. 10/760,091, filed Jun. 12, 2008.
European Search Report for EP 06 00 8181, mailed on May 29, 2008, 14 pages.
Statement of Substance of Interview from U.S. Appl. No. 10/945,608, filed Aug. 7, 2008.
Response to Office Action from U.S. Appl. No. 10/954,695, filed May 5, 2008.
Submission Accompanying a Request for Continued Examination Under 37 CFR 1.114 from U.S. Appl. No. 11/437,428, filed Apr. 25, 2008.
Non-Final Office Action from U.S. Appl. No. 11/437,428, mailed on Jun. 11, 2008.
Non-Final Office Action from U.S. Appl. No. 10/760,091, mailed on Aug. 19, 2008.
Notice of Appeal, filed Aug. 4, 2008.
Notice of Docketing, filed Aug. 22, 2008.
Court Docket From Pacer for *Scantibodies Laboratory, Inc.* v. *Immutopics, Inc.*, The United States District Court for the Central District of California (Western Division), Case No. CV 04-08871 MRP (MANx), docket accessed Aug. 26, 2008.
Amended Notice of Appeal, filed Aug. 28, 2008.
Court Docket From Pacer for *Scantibodies Laboratory, Inc.* v. *Immutopics, Inc.*, currently pending at the United States Court of Appeals for the Federal Circuit, Case No. 2008-1522, docket accessed Aug. 29, 2008.
Petition Decision from U.S. Appl. No. 10/945,608, mailed on Sep. 26, 2008.
Amendment in Response to Non-Final Office Action from U.S. Appl. No. 11/799,726, filed Sep. 29, 2008.
Notice of Allowance from U.S. Appl. No. 10/617,489, mailed on Oct. 2, 2008.
Petition Decision from U.S. Appl. No. 10/617,489, mailed on Oct. 22, 2008.
Transcript of Oral Hearing Held on Wednesday, Jul. 23, 2008 in Patent Interference 105,575 (MPT) Before the Board of Patent Appeals and Interferences.
Amendment and Reply Under 37 CFR 1.111 from U.S. Appl. No. 11/437,428, filed Nov. 12, 2008.
Amendment Accompanying a Request for Continued Examination from U.S. Appl. No. 10/168,185, filed Aug. 22, 2008.
Non-Final Office Action from U.S. Appl. No. 10/168,185, mailed on Nov. 17, 2008.
Notice of Allowance from U.S. Appl. No. 10/674,294, mailed on Aug. 7, 2008.
Final Office Action from U.S. Appl. No. 11/516,912, mailed on Sep. 4, 2008.
Amendment After Final Action Under 37 C.F.R. 1.116 from U.S. Appl. No. 11/516,912, filed Oct. 21, 2008.
Advisory Action from U.S. Appl. No. 11/516,912, mailed on Nov. 10, 2008.
Memorandum of Points and Authorities in Support of Defendants' and Counterclaimants' Motion for Summary Judgment for Failing to Disclose the Best Mode, filed Nov. 13, 2007.
Declaration of Matthew A. Newboles in Support of Defendants' and Counterclaimants' Motion for Summary Judgment for Failing to Disclose the Best Mode, filed Nov. 13, 2007.

Memorandum of Points and Authorities in Support of Defendants' and Counterclaimants' Motion for Summary Judgment of Patent Invalidity for Violation of On Sale Bar and for Obviousness over the Prior Art, filed Nov. 13, 2007.
Declaration of Matthew A. Newboles in Support of Defendants' and Counterclaimants' Motion for Summary Judgment of Patent Invalidity for Violation of On Sale Bar and for Obviousness over the Prior Art, filed Nov. 13, 2007.
Memorandum of Points and Authorities in Support of Defendants' and Counterclaimants' Motion for Summary Judgment of Patent Invalidity for Lack of Enablement, filed Nov. 13, 2007.
Declaration of Matthew A. Newboles in Support of Defendants' and Counterclaimants' Motion for Summary Judgment of Patent Invalidity for Lack of Enablement, filed Nov. 13, 2007.
Memorandum of Points and Authorities in Support of Defendants' and Counterclaimants' Motion for Summary Judgment of Non-Infringement of the '566 Patent, filed Nov. 13, 2007.
Declaration of Jeffrey Lavigne in Support of Defendants' and Counterclaimants' Motion for Summary Judgment Based on Non-Infringement of the '566 Patent, filed Nov. 13, 2007.
Declaration of John W. Colford, M.D. In Opposition to Plaintiff's Motion for Partial Summary Judgment on Defendants' Counterclaim of Patent Invalidity Under 35 U.S.C. §§ 102 and 103, filed Dec. 17, 2007.
Defendants and Counterclaimants' Memorandum of Points and Authorities in Opposition to Plaintiff's Motion for Partial Summary Judgment on Defendants' Counterclaim of Patent Invalidity Under 35 U.S.C. §§ 102 and 103, filed Dec. 17, 2007.
U.S. Appl. No. 10/956,760, filed by Cantor on Oct. 1, 2004.
Restriction Requirement from U.S. Appl. No. 10/956,760, mailed on Mar. 29, 2007.
Response to Restriction Requirement from U.S. Appl. No. 10/956,760, filed Apr. 23, 2007.
Non-Final Office Action from U.S. Appl. No. 10/956,760, mailed on Jul. 16, 2007.
Amendment in Response to Non-Final Office Action from U.S. Appl. No. 10/956,760, filed on Oct. 16, 2007.
Office Communication from U.S. Appl. No. 10/956,760, mailed on Apr. 2, 2008.
Amendment in Response to Office Communication from U.S. Appl. No. 10/956,760, filed Apr. 29, 2008.
Declaration of Matthew A. Newboles in Opposition to Plaintiff's Motion for Partial Summary Judgment on Defendants' Counterclaim of Patent Invalidity Under 35 U.S.C. §§ 102 and 103, filed Dec. 14, 2007.
Defendant and Counterclaimants Immutopics, Inc.'s and Immutopics International, LLC's Statement of Genuine Issues in Opposition to Plaintiff's Motion for Partial Summary Judgment on Defendants' Counterclaim of Patent Invalidity Under 35 U.S.C. §§ 102 and 103, filed Dec. 14, 2007.
Confidential Declaration of Brian W. Kasell in Support of Plaintiff's Opposition to Defendant's Motion for Summary Judgment Based on Non-Infringement, filed Dec. 18, 2007.
Defendants and Counterclaimants Immutopics, Inc. and Immutopics International, LLC's Objections to the Declaration of Brian W. Kasell, filed Jan. 18, 2008.
Defendant's and Counterclaimant's Immutopics, Inc. and Immutopics International, LLC's Objections to the Declaration of Thomas L. Cantor, filed Jan. 18, 2008.
[Proposed] Statement of Uncontroverted Facts and Conclusion of Law in Support of Defendants' and Counterclaimants' Motion for Summary Judgment for Failing to Disclose the Best Mode, filed Jan. 18, 2008.
Immutopics' Reply Memorandum of Points and Authorities in Support of its Motion for Summary Judgment for Failure to Disclose the Best Mode, filed Jan. 18, 2008.
Supplemental Declaration of Matthew A. Newboles in Support of Defendants' and Counterclaimants' Reply for Motion for Summary Judgment of Patent Invalidity for Violation of Best Mode, filed Jan. 18, 2008.

Immutopics' Reply to Plaintiff's Statement of Genuine Issues of Material Fact in Support of its Opposition to Defendants' Motion for Summary Judgment for Failing to Disclose the Best Mode, filed Jan. 18, 2008.
Immutopics' Response to Plaintiff's Objections to the Declaration of Matthew A. Newboles in Support of Defendants' Motion for Summary Judgment of Patent Invalidity for Violation of Best Mode, filed Jan. 18, 2008.
Statement of Uncontroverted Facts and Conclusions of Law in Support of Defendants' and Counterclaimants' Motion for Summary Judgment of Patent Invalidity for Lack of Enablement, filed Jan. 18, 2008.
Immutopics Reply Memorandum of Points and Authorities in Support of its Motion for Summary Judgment of Patent Invalidity for Lack of Enablement, filed Jan. 18, 2008.
Supplemental Declaration of Matthew A. Newboles in Support of Defendants' and Counterclaimants' Reply for Motion for Summary Judgment of Patent Invalidity for Lack of Enablement, filed Jan. 18, 2008.
Immutopics' Reply to Plaintiff's Statement of Genuine Issues of Material Fact in Support of its Opposition to Defendants' Motion for Summary Judgment of Patent Invalidity for Lack of Enablement, filed Jan. 18, 2008.
Immutopics' Response to Plaintiff's Objections to the Declaration of Matthew A. Newboles in Support of Defendants' Motion for Summary Judgment of Patent Invalidity for Lack of Enablement, filed Jan. 18, 2008.
Declaration of Matthew A. Newboles in Support of Immutopics, Inc.'s Motion for Summary Judgment of Non-Infringement, filed Nov. 12, 2007.
[Proposed] Statement of Uncontroverted Facts and Conclusions of Law in Support of Defendants' Motion for Summary Judgment Based on Non-Infringement of the '566 Patent, filed Nov. 12, 2007.
Memorandum of Points and Authorities in Support of Plaintiff's Opposition to Defendants' Motion for Summary Judgment of Non-Infringement of the '566 Patent, filed Dec. 18, 2007.
Plaintiff's Statement of Genuine Issues of Material Fact in Support of Its Opposition to Defendants' Motion for Summary Judgment Based on Non-Infringement of the '566 Patent, filed Dec. 18, 2007.
Immutopics Reply Memorandum of Points and Authorities in Support of Its Motion for Summary Judgment of Non-Infringement of the '566 Patent, filed Jan. 18, 2008.
Supplemental Declaration of Matthew A. Newboles in Support of Reply for Defendants' Motion for Summary Judgment of Non-Infringement, filed Jan. 18, 2008.
Immutopics' Response to Plaintiff's Objections to the Declaration of Matthew A. Newboles in Support of Defendants' Motion for Summary Judgment of Non-Infringement of the '566 Patent, filed Jan. 18, 2008.
Immutopics' Reply to Plaintiff's Statement of Genuine Issues of Material Fact in Support of Its Motion for Summary Judgment Based on Non-Infringement of the '566 Patent, filed Jan. 18, 2008.
[Proposed] Statement of Uncontroverted Facts and Conclusions of Law in Support of Defendants' and Counterclaimants' Motion for Summary Judgment of Patent Invalidity for Violation of On Sale Bar and Obviousness Over the Prior Art, filed Nov. 13, 2007.
Immutopics Reply Memorandum of Points and Authorities in Support of Its Motion for Summary Judgment of Patent Invalidity for Violation of the of On Sale Bar and Obviousness Over the Prior Art, filed Jan. 18, 2008.
Supplemental Declaration of Matthew A. Newboles in Support of Defendants' and Counterclaimants' Reply for Motion for Summary Judgment of Patent Invalidity for Violation of On Sale Bar and Obviousness Over the Prior Art, filed Jan. 18, 2008.
Immutopics' Reply to Plaintiff's Statement of Genuine Issues of Material in Support of Its Opposition to Defendants' Motion for Summary Judgement of Patent Invalidity for Violation of On Sale Bar and Obviousness Over the Prior Art, filed Jan. 18, 2008.
Immutopics' Response to Plaintiff's Objections to the Declaratation of Matthew A. Newboles in Support of Defendant's Motion for Summary Judgement of Patent Invalidity for Violation of On Sale Bar and Obviousness Over the Priort Art, filed Jan. 18, 2008.

Stipulation Regarding Amendment of Judgment Nunc Pro Tunc to Include Determination of "No Just Reason for Delay" Pursuant to Rule 54(b), filed Nov. 5, 2008.
Amended Claim Construction Order, filed Nov. 26, 2008.
Court Docket From Pacer for *Scantibodies Laboratory, Inc.* v. *Immutopics, Inc.*, The United States District Court for the Central District of California (Western Division), Case No. CV 04-08871 MRP (MANx), docket accessed Dec. 1, 2008.
Court Docket From Pacer for *Scantibodies Laboratory, Inc.* v. *Immutopics, Inc.*, currently pending at the United States Court of Appeals for the Federal Circuit, Case No. 2008-1522, docket accessed Dec. 1, 2008.
Petition Decision from U.S. Appl. No. 10/945,608, mailed on Nov. 19, 2008.
Record of Oral Hearing from Reexamination Control No. 90/007,412, dated Oct. 1, 2008.
Notice of Allowance from U.S. Appl. No. 10/956,760, mailed on Aug. 14, 2008.
Court Docket From Pacer for *Scantibodies Laboratory, Inc.* v. *Immutopics, Inc.*, The United States District Court for the Central District of California (Western Division), Case No. CV 0408871 MRP (MANx), docket accessed Jan. 20, 2009.
Court Docket From Pacer for *Scantibodies Laboratory, Inc.* v. *Immutopics, Inc.*, currently pending at the United States Court of Appeals for the Federal Circuit, Case No. 2008-1522, docket accessed Jan. 7, 2009.
Appeal Brief from Japanese Application No. 2000-593958 (in Japanese only), filed on Dec. 7, 2005.
Claims Allowed by the Appeal Board from Japanese Application No. 2000-593958, Feb. 8, 2008.
Amendment from Japanese Application No. 2000-593958 (in Japanese only), filed on Mar. 28, 2008.
Decision on Appeal (Notice of Allowance) from Japanese Application No. 2000-593958, mailed on May 2, 2008.
Amendment from Canadian Application No. 2,360,020, filed Sep. 12, 2007.
Office Action from Canadian Application No. 2,360,020, dated Sep. 30, 2008.
Petition Decision from U.S. Appl. No. 10/617,489, mailed on Dec. 15, 2008.
Petition Decision from U.S. Appl. No. 10/617,489, mailed on Dec. 22, 2008.
RCE and Interview Summary from U.S. Appl. No. 10/617,489, filed Jan. 2, 2009.
Immutopics, Inc. and Immutopics International, LLC's Comments to Amended Claim Construction Order, filed Jan. 16, 2009.
Declaration of Matthew A. Newboles in Support of Immutopics, Inc. and Immutopics International, LLC's Comments to Amended Claim Construction Order, filed Jan. 16, 2009.
Plaintiff's Memorandum on its Positions Concerning the Nov. 26, 2008 Amended Claim Construction Order, filed Jan. 16, 2009.
Notice of Allowance from U.S. Appl. No. 10/945,608, mailed on Jan. 28, 2009.
Final Office Action from U.S. Appl. No. 11/799,726, mailed on Dec. 31, 2008.
Second Amended Claim Construction Order, filed Feb. 9, 2009.
Amendment in Response to Non-Final Office Action from U.S. Appl. No. 10/760,091, filed Feb. 19, 2009.
Final Office Action from U.S. Appl. No. 11/437,428, mailed on Feb. 5, 2009.
Notice of Allowance from U.S. Appl. No. 10/617,489, mailed on Mar. 23, 2009.
Petition Decision from U.S. Appl. No. 10/617,489, mailed on Apr. 3, 2009.
First Preliminary Amendment and Request for Continued Examination from U.S. Appl. No. 11/799,726, filed Mar. 31, 2009.
Office Action from EP Application No. 06008181.7, dated Feb. 9, 2009.
Decision on Appeal from Control No. 90/007,412, decided Mar. 30, 2009.
Interview Summary from U.S. Appl. No. 10/168,185, mailed on Mar. 9, 2009.
Amendment in Response to Non-Final Office Action from U.S. Appl. No. 10/168,185, filed on Apr. 13, 2009.
Declaration of Thomas L. Cantor in Support of Plaintiff's Opposition to Defendants' Motion for Summary Judgment of Non-Infringement in View of the Court's Second Amended Claim Construction Order, filed Mar. 30, 2009.
Notice of Errata Regarding Declaration of Thomas L. Cantor in Support of Plaintiff's Opposition to Defendants' Motion for Summary Judgment of Non-Infringement in View of the Court's Second Amended Claim Construction Order, filed Apr. 1, 2009.
Immutopics' Objections to the Declaration of Thomas L. Cantor in Support of Plaintiff's Opposition to Defendants' Motion for Summary Judgment of Non-Infringement in View of the Court's Second Amended Claim Construction Order, filed Apr. 13, 2009.
Court Docket From Pacer for *Scantibodies Laboratory, Inc.* v. *Immutopics, Inc.*, The United States District Court for the Central District of California (Western Division), Case No. CV 04-08871 MRP (MANx), docket accessed Apr. 21, 2009.
Memorandum of Points and Authorities in Support of Immutopics' Motion for Summary Judgment of Non-Infringement of the '566 Patent in View of the Court's Second Amended Claim Construction Order, dated Mar. 6, 2009.
Declaration of Matthew A. Newboles in Support of Immutopics' Motion for Summary Judgment Based on Non-Infringement of the '566 Patent in View of the Court's Second Amended Claim Construction Order, dated Mar. 6, 2009.
Declaration of Jeffrey Lavigne in Support of Immutopics' Motion for Summary Judgment Based on Non-Infringement of the '566 Patent in View of the Court's Second Amended Claim Construction Order, dated Mar. 6, 2009.
Decision Returning Improper Papers from Control No. 90/007,685 and 90/007,732, mailed on Apr. 21, 2009.
Petition Decision from U.S. Appl. No. 10/641,780, mailed on May 8, 2009.
Final Office Action from U.S. Appl. No. 10/760,091, mailed on May 7, 2009.
Petition Decision from U.S. Appl. No. 10/760,091, mailed on May 8, 2009.
Notice of Non-Compliant Information Disclosure Statement from U.S. Appl. No. 10/945,608, mailed on May 7, 2009.
Petition Decision from U.S. Appl. No. 10/945,608, mailed on May 8, 2009.
Opposition Decision (with English summary) from Opposition against JP patent No. 3457004, dated Sep. 8, 2008.
Revised Order for Summary Judgment of Non-Infringement, filed Apr. 23, 2009.
Court Docket From Pacer for *Scantibodies Laboratory, Inc.* v. *Immutopics, Inc.*, The United States District Court for the Central District of California (Western Division), Case No. CV 04-08871 MRP (MANx), docket accessed Jun. 11, 2009.
Order—Bd.R. 104(a), filed Jun. 9, 2009, Patent Interference No. 105,575 (MPT).
Non-Final Office Action from U.S. Appl. No. 11/799,726, mailed on Jun. 11, 2009.
Barbier et al., J. Med. Chem. (1997) 40:1373-1380.
Nussbaum et al., J. Biol. Chem. (1980) 255:10183-10187.
Jameson and Wolf, The Antigenic Index: A Novel Algorithm for Predicting Antigenic Determinants, Cabios 4, 1988, pp. 181-186.
Communication pursuant to Article 94(3) EPC for European Patent Application No. 06008181.7, mailed on Feb. 9, 2009, 1 page.
Response to Communication pursuant to Article 94(3) EPC for European Patent Application No. 06008181.7, dated Jun. 18, 2009, 20 pages.
Zahradnik Notification of Court Decision in Related Litigation, filed Jun. 16, 2009, from Patent Interference No. 105,575 (MPT).
Letter from Leonard Svensson regarding Patent Interference No. 105,575 (MPT), dated Jun. 17, 2009.
Restriction Requirement for U.S. Appl. No. 11/894,367, mailed on Jun. 12, 2009, 7 pages.
Declaration of Brian W. Kasell in Support of Plaintiff's Opposition to Immutopics' Motion to Declare Case Exceptional Pursuant to 35 U.S.C. § 285 and for Leave to Submit Detailed Description of Attorney Fees, filed on Jun. 15, 2009.

Memorandum of Points and Authorities in Opposition to Immutopics' Motion to Declare Case Exceptional Pursuant to 35 U.S.C. § 285 and for Leave to Submit Detailed Description of Attorney Fees, filed on Jun. 15, 2009.
Cantor Response to Zahradnik Notification of Court Decision in Related Litigation, from Patent Interference No. 105,575 (MPT), filed Jun. 23, 2009.
Summons to Attend Oral Proceedings, from an Opposition Against EP Patent No. 1 151 307, dated Jun. 29, 2009.
Final Judgment of Non-Infringement of the '566 Patent in View of the Court's Second Amended Claim Construction Order, filed Jul. 9, 2009.
Court Docket From Pacer for *Scantibodies Laboratory, Inc.* v. *Immutopics, Inc.*, The United States District Court for the Central District of California (Western Division), Case No. CV 04-08871 MRP (MANx), docket accessed Jul. 15, 2009.
Petition Decision from U.S. Appl. No. 11/799,726, mailed on Jun. 26, 2009.
Petition Decision from U.S. Appl. No. 11/894,367, mailed on Jun. 29, 2009.
Response to Restriction Requirement and Amendment from U.S. Appl. No. 11/894,367, filed Jul. 13, 2009.
Statement of Substance of Interview from U.S. Appl. No. 10/617,489, filed Jul. 15, 2009.
Statement of Substance of Interview from U.S. Appl. No. 10/945,608, filed Jul. 15, 2009.
Non-Final Office Action from U.S. Appl. No. 12/286,620, mailed on May 1, 2009.
Response to Office Action from U.S. Appl. No. 12/286,620, filed Jul. 1, 2009.
Supplementary European Search Report for EP Application No. 04786049.9-2402, mailed on May 11, 2009, 5 pages.
Statement of Substance of Interview from U.S. Appl. No. 10/945,608, filed Aug. 13, 2009.
Response to Summons to Attend Oral Proceedings from an Opposition Against EP Patent No. 1 151 307, dated Jul. 8, 2009 (with English translation).
Notice of Intent to Issue Ex Parte Reexamination Certificate from Control No. 90/007,412, mailed on Aug. 14, 2009.
Office Action from Canadian Patent Application No. 2,360,020, dated Jul. 16, 2009.
Amendment in Response to Non-Final Office Action from U.S. Appl. No. 11/799,729, filed Aug. 31, 2009.
Memorandum Opinion and Order, Decision on Motions, from Patent Interference No. 105,575 (MPT), filed Sep. 30, 2009.
Judgment—Bd. R. 127, from Patent Interference No. 105,575 (MPT), filed Sep. 30, 2009.
Petition Decision from U.S. Appl. No. 10/617,489, mailed on Aug. 28, 2009.
Non-Final Office Action from U.S. Appl. No. 11/894,367, mailed on Sep. 25, 2009.
Veprek et al., J. Peptide Research (1999) 5:203-220.
Written Submissions of the Patentee in Respect of Opposition Against EP-B-1151307, filed Oct. 7, 2009, European Patent Office.
Communication to the European Patent Office from Opposition Against EP-B-1151307, dated Oct. 14, 2009.
Petition to Withdraw Application From Issue Pursuant to 37 CFR 1.313(c)(2) from U.S. Appl. No. 10/945,608, filed Oct. 1, 2009.
Decision on Petition from U.S. Appl. No. 10/945,608, mailed on Oct. 5, 2009.
Petition to Withdraw Application From Issue Pursuant to 37 CFR 1.313(c)(2) from U.S. Appl. No. 10/617,489, filed Oct. 1, 2009.
Decision on Petition from U.S. Appl. No. 10/617,489, mailed on Oct. 5, 2009.
Brief Communication from EP Opposition Against EP-B-1151307, dated Oct. 14, 2009.
Brief Communication from EP Opposition Against EP-B-1151307, dated Oct. 15, 2009.
NonConfidential Brief of Plaintiff-Appellant Scantibodies Laboratory, Inc., filed Oct. 26, 2009, United States Court of Appeals for the Federal Circuit, Case No. 2009-1481.

Court Docket from Pacer for *Scantibodies Laboratory, Inc.* v. *Immutopics, Inc.*, currently pending at the United States Court of Appeals for the Federal Circuit, Case No. 2009-1481, docket accessed Oct. 28, 2009.
Preliminary Amendment from U.S. Appl. No. 10/617,489, filed Oct. 27, 2009.
Confidential Brief of Plaintiff-Appellant Scantibodies Laboratory, Inc., filed October 26, 2009, United States Court of Appeals for the Federal Circuit, Case No. 2009-1481.
Office Action from Australian patent application No. 2004266128, dated Sep. 10, 2009.
Request for Continued Examination and Preliminary Amendment from U.S. Appl. No. 10/760,091, filed on Nov. 5, 2009.
Final Office Action from U.S. Appl. No. 11/799,726, mailed on Nov. 2, 2009.
Communication to the European Patent Office from Opposition Against EP-B-1151307, dated Nov. 26, 2009 (with English Translation).
John et al., Journal of Clinical Endocrinology and Metabolism (1999) 84(11):4287-4290.
Slatopolsky et al., Journal of the American Society of Nephrology (1999) 10:625A.
Gao et al., J. Bone Miner. Res. (1999) 14:SU057, S446.
Decision Revoking European Patent No. 1 151 307, dated Jan. 14, 2010.
Notice of Allowance from U.S. Appl. No. 10/617,489, mailed on Nov. 30, 2009.
Notice of Allowance from U.S. Appl. No. 10/945,608, mailed on Dec. 1, 2009.
Statement of Substance of Interview from U.S. Appl. No. 10/945,608, filed Feb. 2, 2010.
Amendment After Final Action Under 37 CFR 1.116 from U.S. Appl. No. 11/799,726, filed Dec. 30, 2009.
Advisory Action from U.S. Appl. No. 11/799,726, mailed on Jan. 21, 2010.
Amendment in Response to Official Action from Canadian Patent Application No. 2,360,020, filed Jan. 14, 2010.
Non-Final Office Action from U.S. Appl. No. 10/760,091, mailed on Jan. 15, 2010.
Office Action from EP Patent Application No. 04786049.9 dated Dec. 30, 2009.
Non-Confidential Brief for Defendants-Appellees, filed Dec. 22, 2009, United States Court of Appeals for the Federal Circuit, Case No. 2009-1481.
Corrected Non-Confidential Brief for Defendants-Appellees, filed Jan. 8, 2010, United States Court of Appeals for the Federal Circuit, Case No. 2009-1481.
Reply Brief of Plaintiff-Appellant Scantibodies Laboratory, Inc., filed Jan. 12, 2010, United States Court of Appeals of Court for the Federal Circuit, Case No. 2009-1481.
Non-Confidential Joint Appendix, vol. 1, filed Jan. 22, 2010, United States Court of Appeals for the Federal Circuit, Case No. 2009-1481.
Non-Confidential Joint Appendix, vol. 2, filed Jan. 22, 2010, United States Court of Appeals for the Federal Circuit, Case No. 2009-1481.
Amendment in Response to Non-Final Office Action from U.S. Appl. No. 11/894,367, filed Jan. 21, 2010.
Bailie et al., Pharmacotherapy (2005) 25(12):1687-1707.
Request for Continued Examination and Amendment Under 37 C.F.R. § 1.116 from U.S. Appl. No. 11/799,726, filed Mar. 2, 2010.
Notice of Appeal of Decision Revoking European Patent No. 1 151 307, dated Mar. 8, 2010.
Commencement of Proceedings Before the Board of Appeal for EP Patent No. 1 151 307, dated Mar. 30, 2010.
Recording of Oral Arguments on Apr. 7, 2010 from *Scantibodies* v. *Immutopics*, United States Court of Appeals for the Federal Circuit, Case No. 2009-1481, available online at: http://oralarguments.cafc.uscourts.gov/mp3/2009-1481.mp3.
Decision on Appeal of Summary Judgment, dated May 6, 2010, United States Court of Appeals for the Federal Circuit, Case No. 2009-1481.
Non-Final Office Action from U.S. Appl. No. 11/799,726, mailed on Apr. 22, 2010.

Statement of Substance of Interview from U.S. Appl. No. 11/894,367, filed May 14, 2010.

Statement of Grounds of Appeal under Article 108 EPC, filed May 21, 2010, from Opposition proceedings against EP Patent No. 1 151 307.

Confidential Brief for Defendants-Appellees, filed Dec. 22, 2009, United States Court of Appeals for the Federal Circuit, Case No. 2009-1481.

Corrected Confidential Brief for Defendants-Appellees, filed Jan. 8, 2010, United States Court of Appeals for the Federal Circuit, Case No. 2009-1481.

Confidential Joint Appendix, vol. 1, filed Jan. 22, 2010, United States Court of Appeals for the Federal Circuit, Case No. 2009-1481.

Confidential Joint Appendix, vol. 2, filed Jan. 22, 2010, United States Court of Appeals for the Federal Circuit, Case No. 2009-1481.

Response to Office Action from European Patent Application No. 04786049.9, filed Jul. 8, 2010, 29 pages.

Final Office Action from U.S. Appl. No. 11/894,367, mailed on Jul. 2, 2010.

Amendment in Response to Non-Final Office Action from U.S. Appl. No. 11/799,726, filed Aug. 23, 2010.

Amendment in Response to Non-Final Office Action from U.S. Appl. No. 10/760,091, filed Jun. 14, 2010.

Standard Curve for Whole PTH Assay

Whole PTH

Big PTH 7-84 Fragment

METHODS FOR DIFFERENTIATING AND MONITORING PARATHYROID AND BONE STATUS RELATED DISEASES

RELATED APPLICATIONS

The present application is a continuation-in-part of a non-provisional utility patent application filed in the United States Patent and Trademark Office, Ser. No. 08/231,422.

The present application is a continuation of U.S. patent application Ser. No. 09/344,639, filed on Jun. 26, 1999, now U.S. Pat. No. 6,743,590; which is a continuation-in-part of U.S. patent application Ser. No. 09/231,422, filed on Jan. 14, 1999, now U.S. Pat. No. 6,689,566.

TECHNICAL FIELD

The present invention relates to novel methods and devices for differentiating in a patient parathyroid diseases, such as hyperparathyroidism, from normal or non-disease states. One detects whole or non-fragmented (1 to 84) parathyroid hormone in a biological sample and also a large non-whole parathyroid hormone peptide fragment that can function as a parathyroid hormone antagonist. By either comparing values or using independently the value of either the large non-whole parathyroid hormone peptide fragment, the whole parathyroid hormone, or the combination of these values one can differentiate parathyroid and bone related disease states, as well as differentiate such states from normal states.

BACKGROUND ART

Calcium plays an indispensable role in cell permeability, the formation of bones and teeth, blood coagulation, transmission of nerve impulse, and normal muscle contraction. The concentration of calcium ions in the blood is, along with calcitrol and calcitonin, regulated mainly by parathyroid hormone (PTH). Although calcium intake and excretion may vary, PTH serves through a feedback mechanism to maintain a steady concentration of calcium in cells and surrounding fluids. When serum calcium lowers, the parathyroid glands secrete PTH, affecting the release of stored calcium. When serum calcium increases, stored calcium release is retarded through lowered secretions of PTH.

The complete form of human PTH, sometimes referred to in the art as hPTH but referred to in the present invention either as whole PTH or wPTH, is a unique 84 amino acid peptide (SEQ ID NO. 1), as is shown in FIG. 1. Researchers have found that this peptide has an anabolic effect on bone that involves a domain for protein kinase C activation (amino acid residues 28 to 34) as well as a domain for adenylate cyclase activation (amino acid residues 1 to 7). However, various catabolic forms of clipped or fragmented PTH peptides also are found in circulation, most likely formed by intraglandular or peripheral metabolism. For example, whole PTH can be cleaved between amino acids 34 and 35 to produce a (1-34) PTH N-terminal fragment and a (35-84) PTH C-terminal fragment. Likewise, clipping can occur between either amino acids 36 and 37 or 37 and 38. Recently, a large PTH fragment referred to as "non-(1-84) PTH" has been disclosed which is clipped closer to the N-terminal end of PTH. (See R. LePage et alia, "*A non-(1-84) circulating parathyroid hormone (PTH) fragment interferes significantly with intact PTH commercial assay measurements in uremic samples*" Clin Chem (1998); 44: 805-810.)

The clinical need for accurate measurement of PTH is well demonstrated. Serum PTH level is one of the most important indices for patients with the following diseases: familial hypocalciuria, hypercalcemia; multiple endocrine neoplasia types I and II; osteoporosis; Paget's bone disease; primary hyperparathyroidism—caused by primary hyperplasia or adenoma of the parathyroid glands; pseudohypoparathyroidism; and renal failure, which can cause secondary hyperparathyroidism.

PTH plays a role in the course of disease in a patient with chronic renal failure. Renal osteodystrophy (RO) is a complex skeletal disease comprising osteitis fibrosa cystica (caused by PTH excess), osteomalacia—unmineralized bone matrix (caused by vitamin D deficiency), extraskeletal calcification/ossification (caused by abnormal calcium and phosphorus metabolism), and adynamic bone disease (contributed to by PTH suppression). Chronic renal failure patients can develop RO. Failing kidneys increase serum phosphorus (hyperphosphoremia) and decrease 1,25-dihydroxyvitamin D (1,25-D) production by the kidney. The former results in secondary hyperparathyroidism from decreased gastrointestinal calcium absorption and osteitis fibrosa cystica from increased PTH in response to an increase in serum phosphorus. The later causes hypocalcemia and osteomalacia. With the onset of secondary hyperparathyroidism, the parathyroid gland becomes less responsive to its hormonal regulators because of decreased expression of its calcium and vitamin D receptors. Serum calcium drops. RO can lead to digital gangrene, bone pain, bone fractures, and muscle weakness.

Determining circulating biologically active PTH levels in humans has been challenging. One major problem is that PTH is found at low levels, normally 10 pg/mL to 65 pg/mL. Coupled with extremely low circulating levels is the problem of the heterogeneity of PTH and its many circulating fragments. In many cases, immunoassays have faced substantial and significant interference from circulating PTH fragments. For example, some commercially available PTH kits have almost 100% cross-reactivity with the non-(1-84) PTH fragment, (see the LePage article).

PTH immunoassays have varied over the years. One early approach is a double antibody precipitation immunoassay found in U.S. Pat. No. 4,369,138 to Arnold W. Lindall et alia. A first antibody has a high affinity for a (65-84) PTH fragment. A radioactive labeled (65-84) PTH peptide is added to the sample with the first antibody to compete for the endogenous unlabeled peptide. A second antibody is added which binds to any first antibody and radioactive labeled PTH fragment complex, thereby forming a precipitate. Both precipitate and supernatant can be measured for radioactive activity, and endogenous PTH levels can be calculated therefrom.

In an effort to overcome PTH fragment interference, immunoradiometric two-site assays for intact PTH (I-PTH) have been introduced, such as Allegro® Intact PTH assay by the Nichol's Institute of San Juan Capistrano, Calif. In one version, a capture antibody specifically binds to the C-terminal portion of hPTH while a labeled antibody specifically binds to the N-terminal portion of the captured hPTH. In another, two monoclonal antibodies were used, both of which attached to the N-terminal portion of hPTH. Unfortunately, these assays have problems in that they measure but do not discriminate between wPTH and non-whole PTH peptide fragments. This inability comes to the fore in hyperparathyroid patients and renal failure patients who have significant endogenous concentrations of large, non-whole PTH fragments.

Recently, researchers have made a specific binding assay directed to the large N-terminal PTH fragments. (See. Gao, Ping et alia "*Immuochemicalluminometric assay with two monoclonal antibodies against the N-terminal sequence of* human parathyroid hormone", Clinica Chimica Acta 245 (1996) 39-59.) This immunochemiluminometric assay uses two monoclonal antibodies to detect N-terminal (1-34) PTH fragments but not mid-portion PTH fragments or C-terminal PTH fragments. A key factor in the design of these assays is to eliminate any reaction with C-terminal PTH fragments.

DISCLOSURE OF THE INVENTION

The present invention relates to novel methods and devices for differentiating in a patient parathyroid diseases, (such as primary hyperparathyroidism, secondary hyperparathyroidism, and stages thereof), from normal or non-disease states; for monitoring the function of parathyroid glands either during or after treatment, i.e., intra-operation and after operation parathyroid function monitoring as well as therapeutic treatment; and also for monitoring the effects of therapeutic treatments for parathyroid related bone diseases and hyperparathyroidism. One detects the level in the serum or blood of at least one of three different parameters, namely, whole or non-fragmented parathyroid hormone in a biological sample, a large non-whole parathyroid hormone peptide fragment that can function as a parathyroid hormone antagonist, or the combination of the two values. By comparing the two values or by examining independently one of the above three values, one can differentiate parathyroid and bone disease states, as well as differentiate such states from normal states, as the relationship between these values, as well as the values themselves, change significantly between a normal person and a patient with a parathyroid disease.

The present invention incorporates a discovery that a large, non-whole PTH peptide fragment, a peptide having an amino acid sequence from between (SEQ ID No.2 [$PTH_{3-84}$]) and (SEQ ID No. 3 [$PTH_{34-84}$]), functions in vivo as a wPTH antagonist or inhibitor (PIN), (see FIG. 12). In other words, the binding of wPTH to PTH receptors and the subsequent biological activity are affected by the presence of this PIN peptide fragment. The PTH receptors can be tied up with respect to PTH or PTH analogs in that the PTH binding site is blocked. The relationship between the concentrations of wPTH and PIN vary with PTH related disease states, and thus, are indicative of such states. Equally useful in view of the discovery of the antagonist nature of PIN, the present invention relates to novel methods and devices for monitoring parathyroid related bone diseases, and resultant bone loss or build-up. Increased amounts of PIN can inhibit the calcium releasing activity of PTH.

In making a measurement of wPTH, one does not want to detect PIN. The method for measuring the amount of wPTH in a sample such as serum, plasma, or blood comprises four general steps which can vary depending upon whether one uses a first antibody or antibody fragment specific for the PTH peptide SER-VAL-SER-GLU-ILE-GLN-LEU-MET (SEQ ID No. 4), wherein at least four amino acids are part of the antibody reactive portion of the peptide either as a signal antibody or a capture antibody in conventional immunoassay formats. (One can also use an analogous peptide present in other species, such as a rat peptide in which the first amino acid serine is substituted with an alanine). Used either as a signal antibody or as a capture antibody, enough antibody is added to bind all wPTH present. Next, one allows the first antibody to bind to any wPTH present, thereby forming a complex. A specific binding label comprised of a second antibody and a conventional immunoassay label, such as chemiluminescent agents, calorimetric agents, energy transfer agents, enzymes, fluorescent agents, and radioisotopes, is used to label the complex, preferably at the C-terminal end of wPTH, and can be added either substantially simultaneously with the first antibody or subsequent thereto. Finally, one uses conventional techniques to measure the amount of labeled complex, and thereby calculate wPTH levels in the sample. If used as a signal antibody, then the first antibody still attaches at the N-terminal end, but the second antibody would serve as a capture antibody that attaches at the C-terminal end.

In making a measurement of PIN, one can either measure it directly, or indirectly. An indirect measurement can be made by first measuring wPTH and then measuring total PTH. Subtracting the wPTH value from the total PTH value, one derives the PIN value. (For the purposes of the present invention, "total PTH" refers to the sum of wPTH, the naturally occurring predominant PTH receptor binding agonist, and PIN, the naturally occurring predominant PTH receptor binding antagonist.) A total PTH assay detects both PIN and wPTH by detecting the N-terminal end of PTH not at SEQ ID No. 4, the very end of the N-terminal. By detecting between about amino acids 7 to 38 of PTH, the assay can detect both. A commercially available assay for total PTH is available from Scantibodies Laboratory, Inc. of Santee, Calif. A direct measurement of total PTH can be made by using an antibody or antibody fragment specific for a portion of the PTH peptide LEU-MET-HIS-ASN-LEU-GLY-LYS-HIS-LEU-ALA-SER-VAL-GLU-ARG-MET-GLN-TRP-LEU-ARG-LYS-LYS-LEU-GLN-ASP-VAL-HIS-ASN-PHE-VAL-ALA-LEU-GLY (SEQ ID No. 5), which comprises amino acids 7 to 38 of PTH, (preferably between amino acids 9 to 34), wherein at least four amino acids are part of the antibody reactive portion of the peptide. Such an antibody or antibody fragment can be used in conventional immunoassay formats either as a signal antibody or a capture antibody.

To differentiate between parathyroid disease states and the normal state or to monitor the effects of therapeutic treatment for parathyroid disease states, one can compare the relationship between the values of wPTH, PIN, or total PTH, (the combination of wPTH and PIN), in other words, the relationship between the values of PIN and total PTH, between PIN and whole PTH, or between whole PTH and total PTH. For example, one can use a proportion between wPTH and total PTH, between PIN and total PTH, or between PIN and wPTH. (Comparisons can even take the form of a neural network of all these factors.) Regardless of the comparative method chosen, these values change significantly between a normal person and a patient with a parathyroid disease and between various stages of parathyroid diseases.

Alternatively, one can either differentiate between parathyroid disease states and the normal state or monitor the effects of therapeutic treatment for parathyroid disease states by examining independently the value of either wPTH, PIN, or total PTH alone.

BEST MODES FOR CARRYING OUT THE INVENTION

Figure 1:
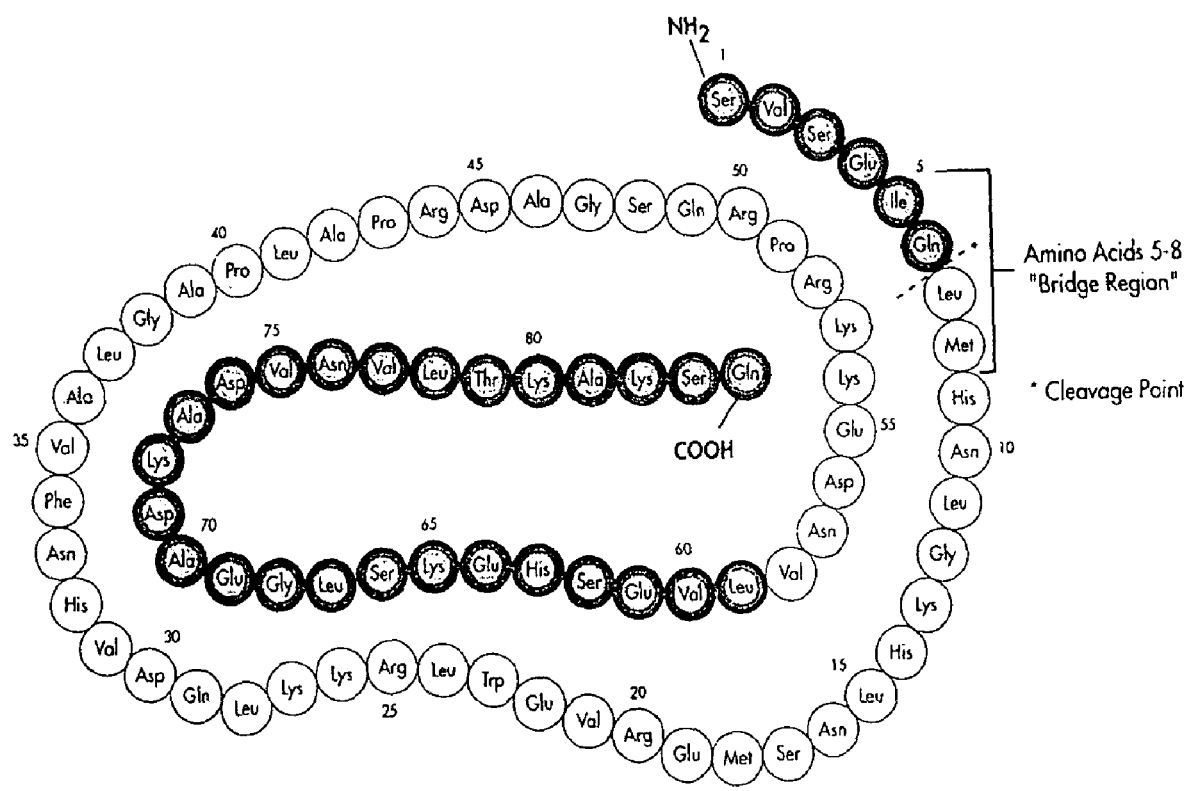
FIG. 1 is a diagrammatic view of human wPTH.

In disclosing the present invention, one should remember that there are a number of closely analogous, species dependent forms of PTH. The amino acid sequence of hPTH is shown in FIG. 1. However, for rat PTH, bovine PTH, or porcine PTH, for example, one finds the substitutions at some of the amino acids in the hPTH sequence. For the purposes of the present invention, one can use interchangeably antibodies or antibody fragments to forms of these PTHs, although it is preferred to use an antibody with specificity for PTH having a sequence matching the species in which the PTH measurements are made.

Whole PTH Immunoassay

Figure 2:
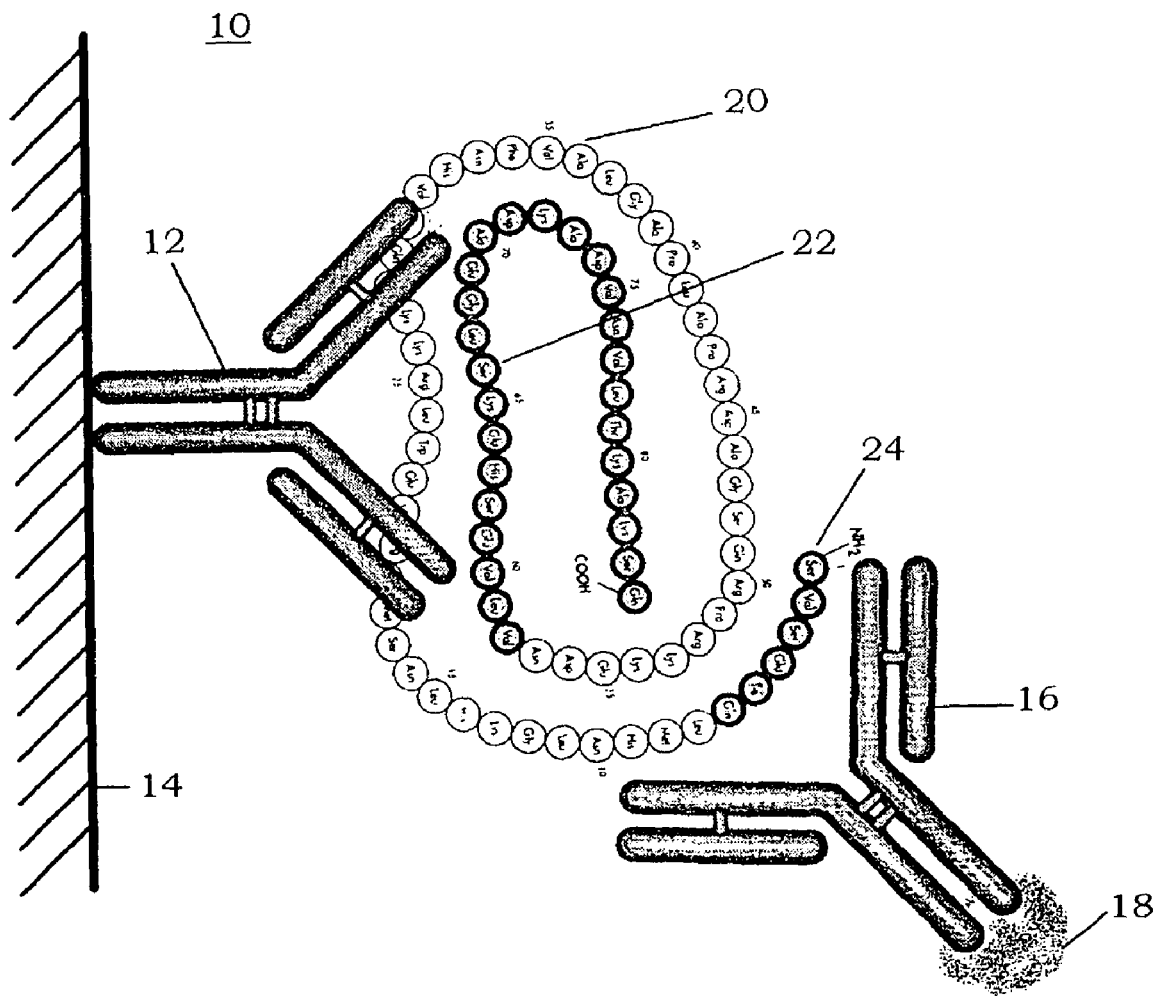
FIG. 2 is a diagrammatic view of a wPTH assay using the present antibody as a tracer element.
Figure 3:
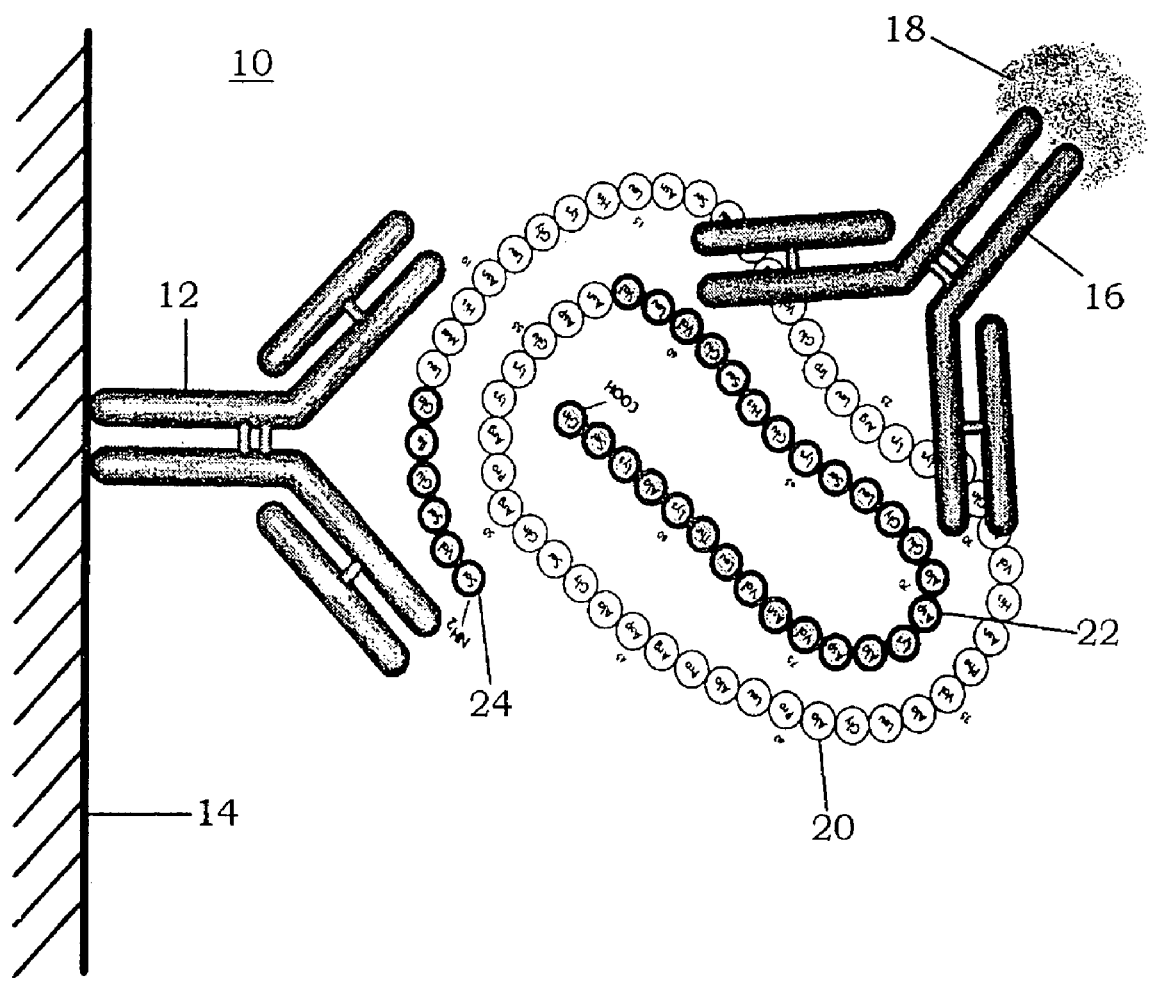
FIG. 3 is a diagrammatic view of a wPTH assay using the present antibody as a capture element.

A preferred embodiment of the present invention is an immunoradiometric assay (IRMA), often referred to as a sandwich assay, as shown FIGS. 2 and 3. Elements employed in such an assay (10) include a capture antibody (12) attached to a solid support (14) and a signal antibody (16) having a label (18), attached thereto (20). Typically, one selects a capture antibody that is specific for C-terminal PTH fragments (22), while the label antibody is specific for the initial wPTH peptide sequence which comprises a domain for adenylate cyclase activation (24), as shown in FIG. 2. However, one could reverse the specificity of these antibodies, as is shown in FIG. 3.

Alternatively, one could create an immunoassay in which wPTH is either precipitated from solution or otherwise differentiated in a solution, as in conventional precipitating assays or turbidometric assays. For example, one can use at least three antibodies to form a precipitating mass. In addition to the initial wPTH sequence antibody and a C-terminal antibody, one can use at least a third antibody which attaches to the mid portion of PTH. The combined mass of wPTH and the at least three antibodies would form a labeled precipitating mass which can be measured by conventional techniques. Another method would be to couple the initial wPTH sequence antibody to colloidal solid supports, such as latex particles.

More specifically, one can create a signal antibody by iodinating 50 micrograms of affinity purified goat anti-(1-6) PTH antibody (Scantibodies Laboratory, Inc., Santee Calif., U.S.A.) by oxidation with chloramine T, incubation for 25 seconds at room temperature with 1 millicurie of 125-I radioisotope and reduction with sodium metabisulfate. Unincorporated 125-I radioisotope is separated from the 125-1-Goat anti-(1-6) PTH signal antibody by, passing the iodination mixture over a PD-10 desalting column (Pharmacia, Uppsala, Sweden) and following the manufacturers instructions. The fractions collected from the desalting column are measured in a gamma counter and those fractions representing the 125-1-goat anti-(1-6) PTH antibody are pooled and diluted to approximately 300,000 DPM (disintegrations per minute) per 100 microliters. This solution is the tracer solution to be used in the whole PTH IRMA.

Capture antibody coated tubes can be created by attaching affinity purified goat anti PTH 39-84 antibody, (Scantibodies Laboratory, Inc., Santee, Calif., U.S.A.), to 12×75 mm polystyrene tubes (Nunc, Denmark) by means of passive absorption techniques which are known to those of skill in the art. The tubes are emptied and dried, creating solid phase antibody coated tubes.

Figure 4:
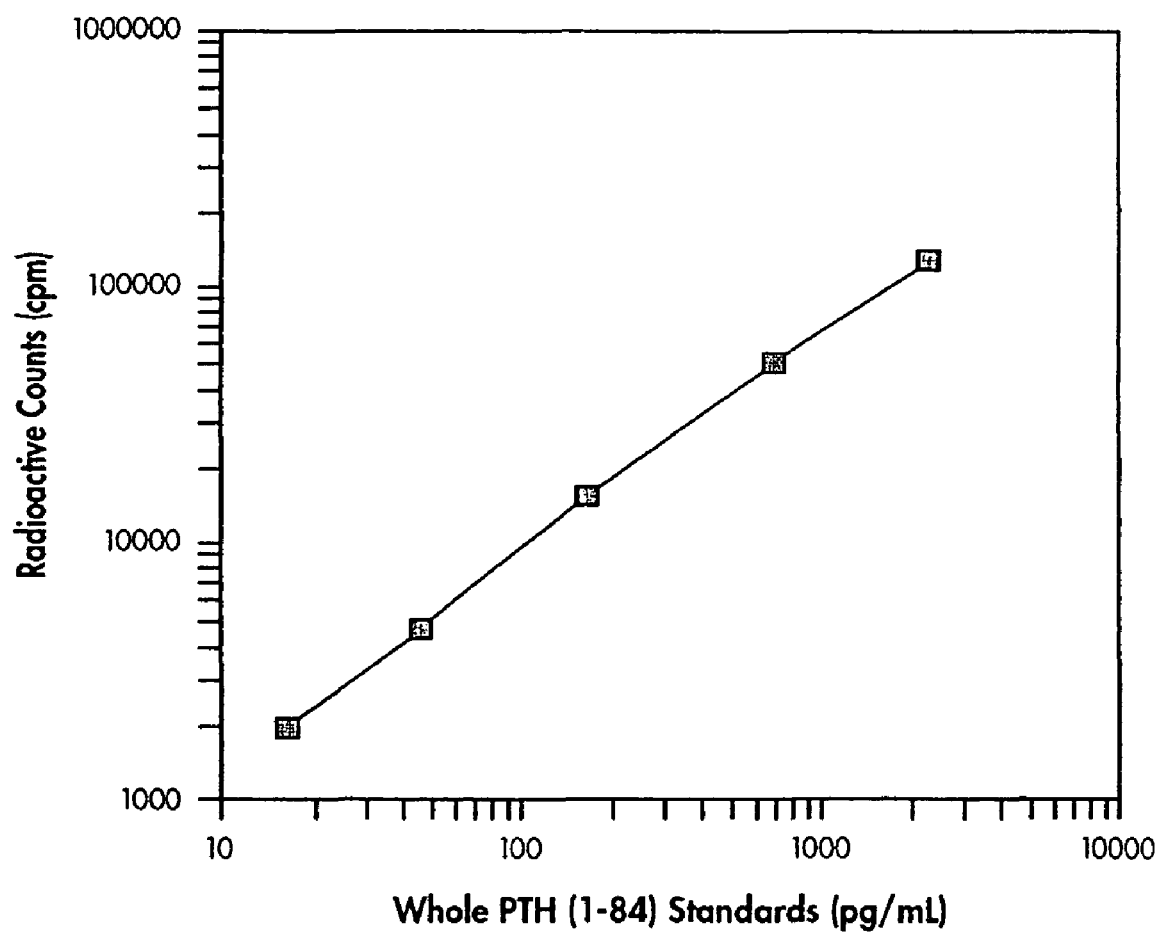
FIG. 4 is a graph showing a standard curve for a wPTH assay.

To conduct a whole PTH assay of a sample, 200 microliter samples of human serum are added to the solid phase antibody coated tubes. To each tube is added 100 microliters of the tracer solution (labeled goat anti-(1-6) PTH signal antibody). The tubes are incubated at room temperature with shaking at 170 rpm for 20-22 hours. During this time the immunochemical reaction of forming the sandwich of {solid phase goat anti-(39-84) PTH antibody}—{whole PTH}—{125-1-goat anti-(1-6) PTH antibody} takes place. Following this incubation, the test tubes are washed with distilled water. Radioactivity on the solid phase, which amount corresponds to the quantity of wPTH present, is measured using a gamma counter. The radioactivity data for the samples is processed by conventional analysis with use of the results from standards and controls and a computer software in order that the concentration of whole PTH in the samples may be ascertained. FIG. 4 shows a standard curve for such an assay.

Initial Whole PTH Sequence Peptide

In order to make the signal antibody in the above assay, first one makes a synthetic PTH peptide corresponding either to hPTH (Ser-Val-Ser-Glu-Ile-Gln-Leu-Met) (SEQ ID NO:4), rat PTH (Ala-Val-Ser-Glu-Ile-Gln-Leu-Met) (SEQ ID NO:7), or at least four amino acids in the common sequence. The selected peptide can play two roles in making an assay, first as a specific source for creating a polyclonal antibody or monoclonal antibody source for signal antibody or capture antibody, and second as part of an affinity purification means for isolating the desired signal antibody or capture antibody.

Briefly, such a peptide can be synthesized on an Applied Biosystems, Inc. (Foster City, Calif., U.S.A.) Model 431 automated peptide synthesizer employing Fmoc (9-fluoronylmethoxycarbonyl) as the alpha-amino protecting group. All amino acids and solvents are from Applied Biosystems and are of synthesis grade. Following synthesis, the peptide is cleaved from the resin, and side chains are de-blocked, using a cleavage cocktail containing 6.67% phenol, 4.4% (v/v) thioanisole and 8.8% ethanedithiol in trifluoroacetic acid (TFA). The cleaved peptide is precipitated and washed several times in cold diethyl ether. It is then dissolved in water and lyophilized. The crude peptide is subjected to amino acid analysis (Waters PICO-TAG System, Boston, Mass., U.S.A.) and reversed-phase HPLC using a VYDAC (TM) C8 column with 0.1% TFA in water and 99.9% acetonitrile in 0.1% TFA as the mobile buffers. The presence of a single major peak along with the appropriate amino acid composition is taken as evidence that the peptide is suitable for further use.

The resulting peptide is then attached to cross linked agarose beads (activated Sepharose 4B from Pharmacia, Uppsala, Sweden) according to instructions from the manufacturer. Armed with the initial peptide sequence on a bead, one can affinity purify a polyclonal antibody serum source to isolate the initial sequence antibody for the wPTH immunoassay.

Initial Sequence Whole PTH Antibody

To create an affinity-purified anti-(1-6) PTH antibody, one first uses a selected initial PTH sequence peptide as described above as part of an immunogen for injection into a goat. The peptide can be used either by itself as an injectable immunogen, incorporated into a non PTH peptide having a molecular weight, typically, of between about 5,000 and 10,000,000, or as part of the wPTH complete sequence. The immunogen is mixed with an equal volume of Freunds complete adjuvant which is a mixture of light mineral oil, Arlacel detergent, and inactivated mycobacterium tuberculosis bacilli. The resulting mixture is homogenized to produce an aqueous/oil emulsion which is injected into the animal (typically a goat) for the primary immunization. The immunogen dose is approximately 50-400 micrograms. The goats are injected monthly with the same dose of immunogen complex except no mycobacterium tuberculosis bacilli is used in these subsequent injections. The goats are bled monthly, approximately three months after the 20 primary immunization. The serum (or antiserum) is derived from each bleeding by separating the red blood cells from the blood by centrifugation and removing the antiserum which is rich in (1-6) PTH antibodies.

To purify the antiserum for the desired (1-6) PTH antibody, one packs a separation column with the initial PTH sequence peptide bound beads described above, washes the column and equilibrates it with 0.01 M phosphate buffered saline (PBS). The antiserum is loaded onto the column and washed with 0.01 M PBS in order to remove antibodies without the (1-6) PTH specificity. The bound specific goat anti-(1-6) PTH polyclonal antibody is eluted from the solid phase PTH 1-6 in the column by passing an elution solution of 0.1 M glycine hydrochloride buffer, pH 2.5 through the column. The eluted polyclonal antibody is neutralized after it leaves the column with either the addition of 1.0 M phosphate buffer, pH 7.5 or by a buffer exchange with 0.01 M PBS, as is known to those of skill in the art. The polyclonal antibody is stored at 2-8 degrees centigrade.

Comparison Between Whole PTH and Total PTH Assays

Figure 10:
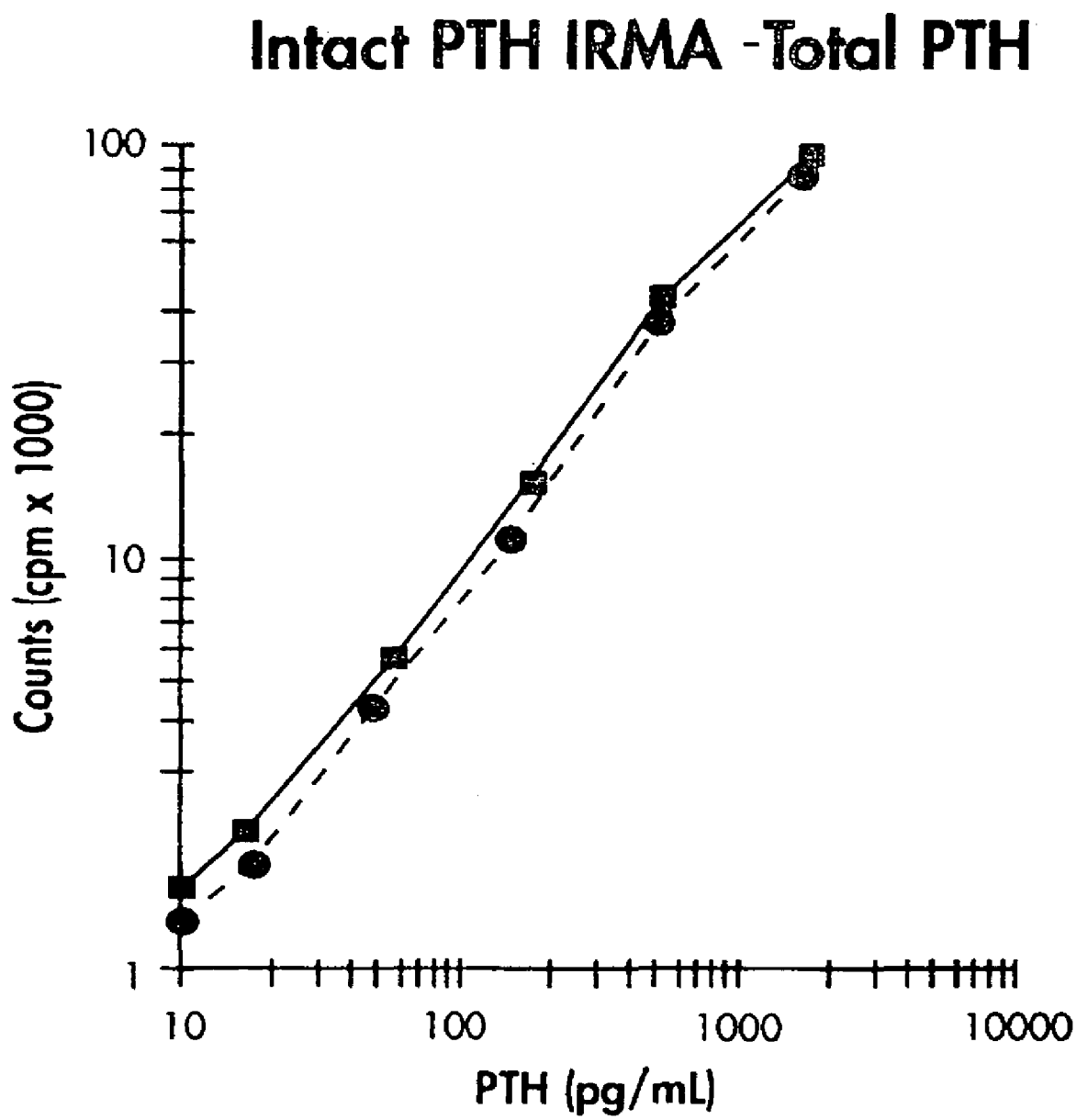
FIG. 10 is a graph demonstrating complete cross-reactivity of wPTH and PIN in a total PTH assay used in the present invention.
Figure 11:
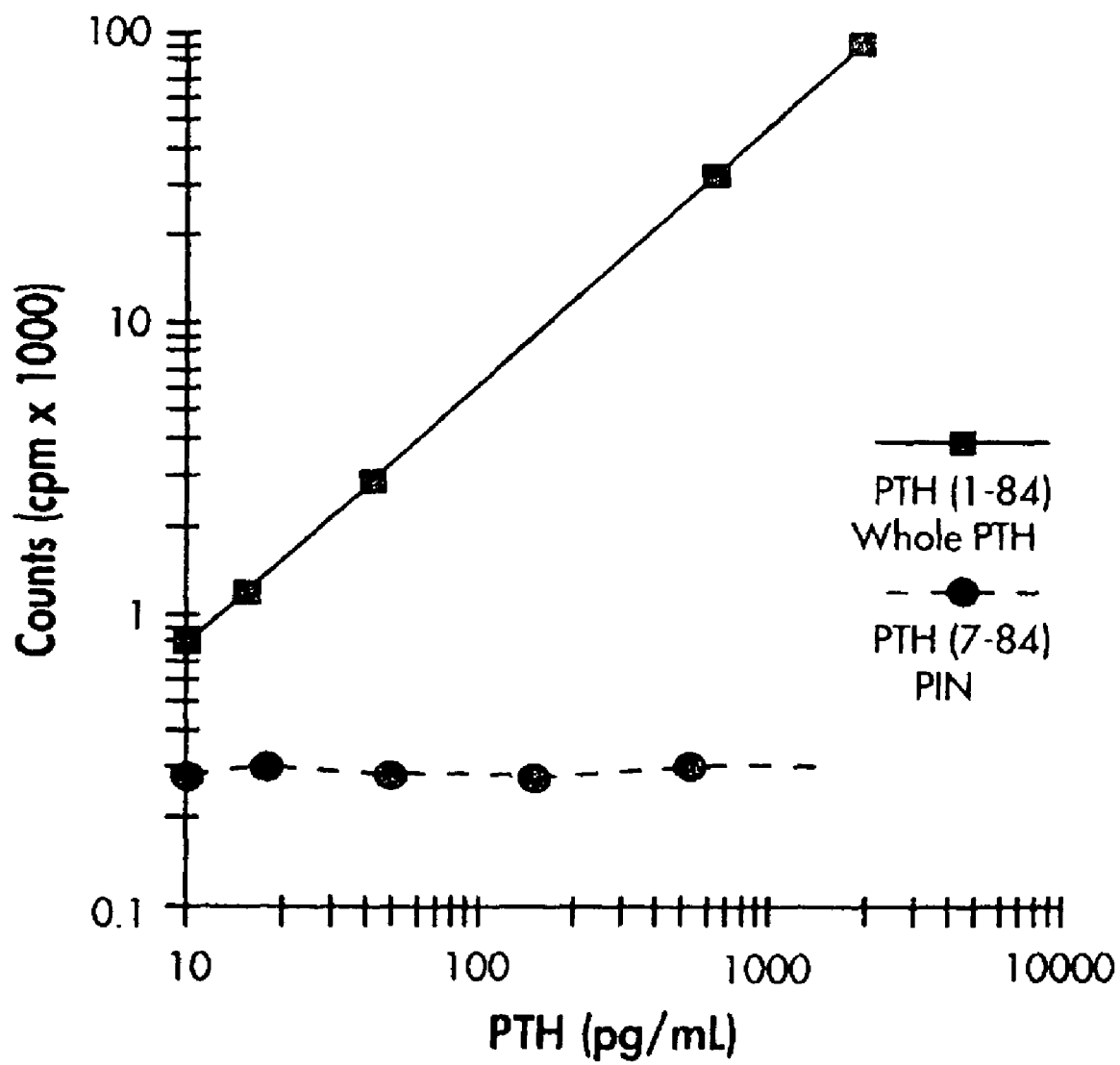
FIG. 11 is a graph demonstrating how the whole PTH assay used in the present invention does not detect to PIN.
Figure 12:
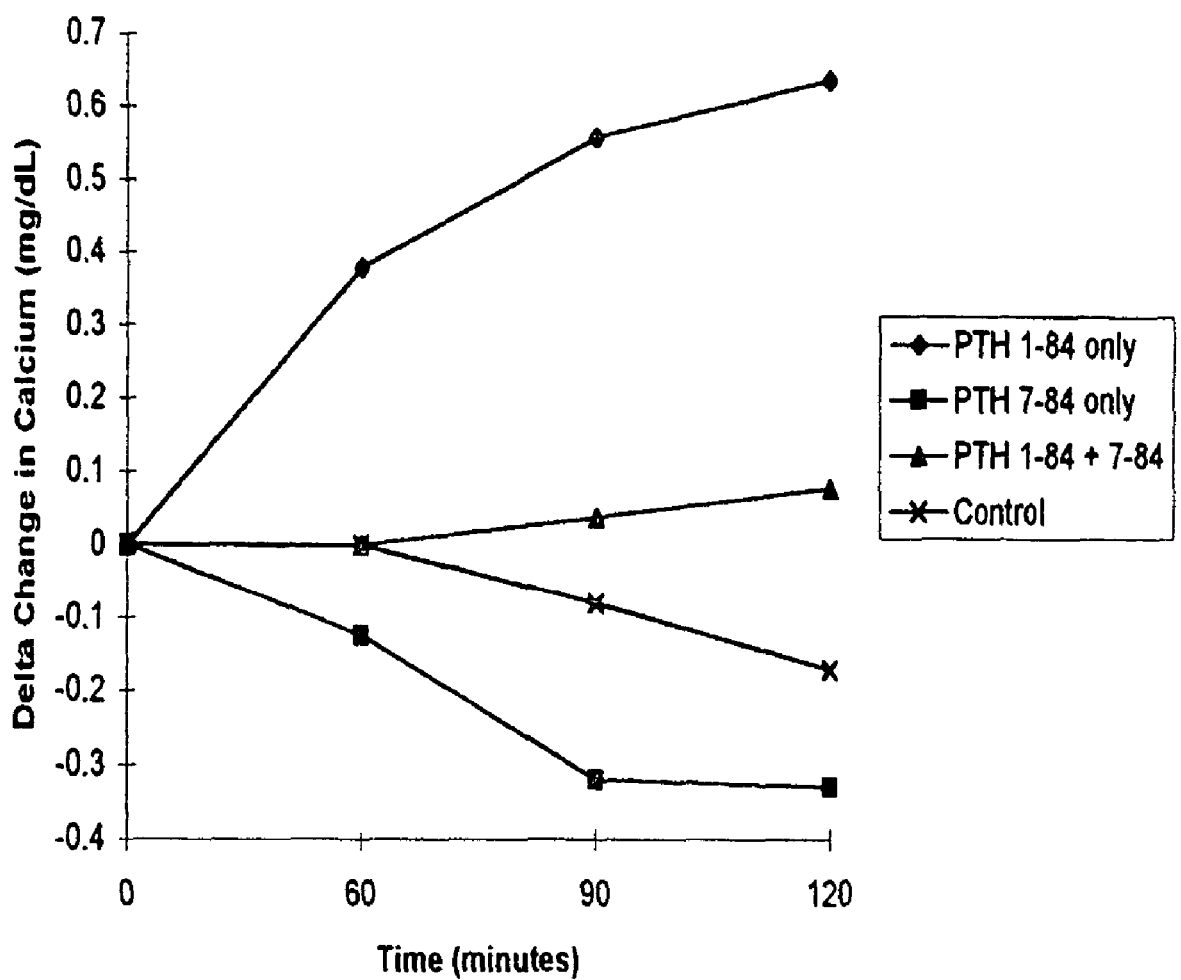
FIG. 12 is a graph demonstrating how PIN is an in vivo inhibitor of wPTH.

The present w PTH IRMA assay was compared to a conventional intact PTH or I-PTH immunoassay, the Allegro Nichols Intact-PTH assay, (which is commercially available and made by Nichols Institute Diagnostics of San Juan Capistrano, Calif., U.S.A.), in both PTH normal persons and those suffering from chronic uremia. This I-PTH immunoassay, due to its 100% cross reactivity between PIN and wPTH, is in actuality a total PTH assay, (see FIG. 10).

Figure 5:
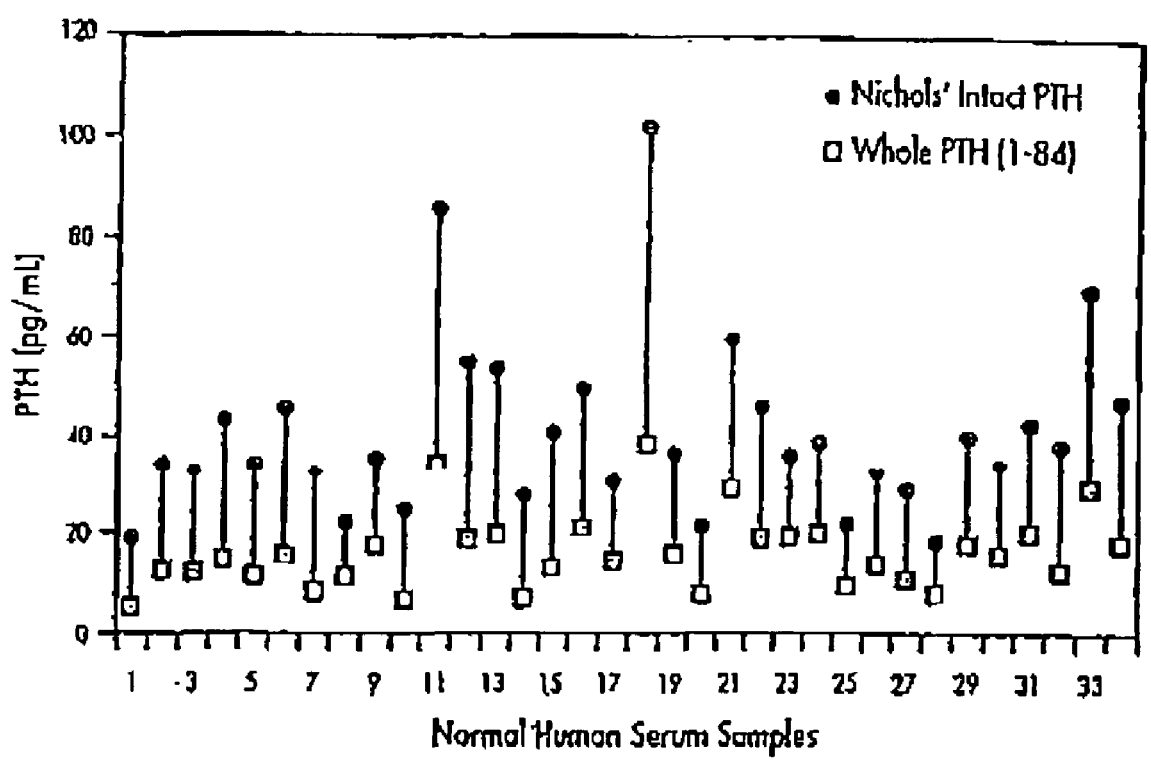
FIG. 5 is a graph comparing a conventional I-PTH assay with the present wPTH assay for healthy normal persons with "normal" PTH values.
Figure 6A:
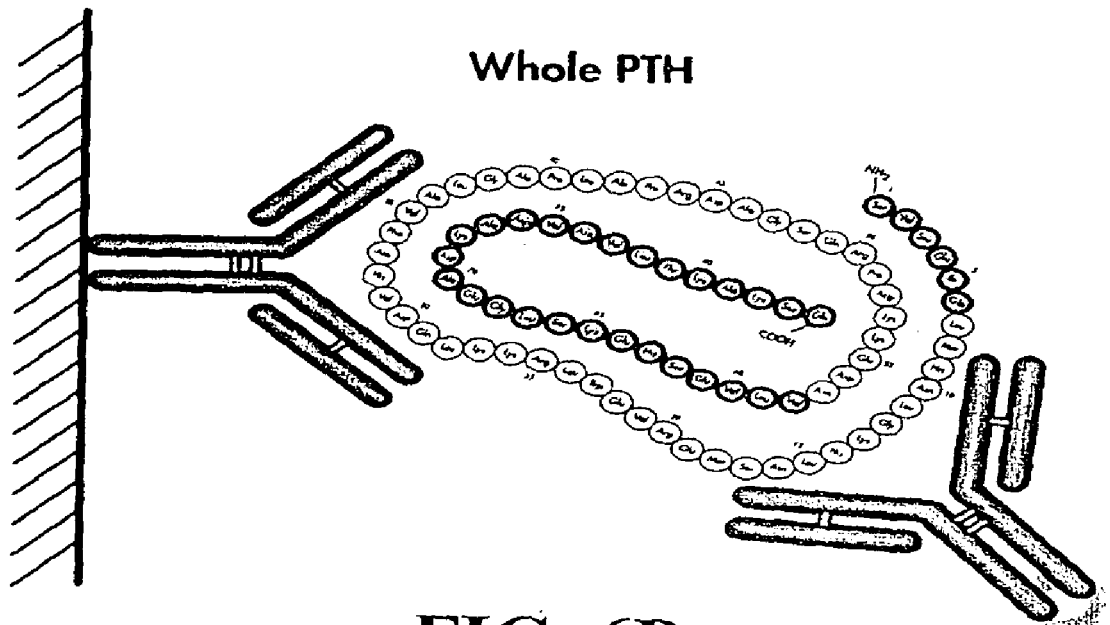
FIGS. 6A and 6B are diagrammatic views showing binding of whole (1-84) PTH compared with interference from non (1-84) PTH fragments (e.g., (7-84) PTH (SEQ ID NO:6)) in conventional I-PTH assays.
Figure 6B:
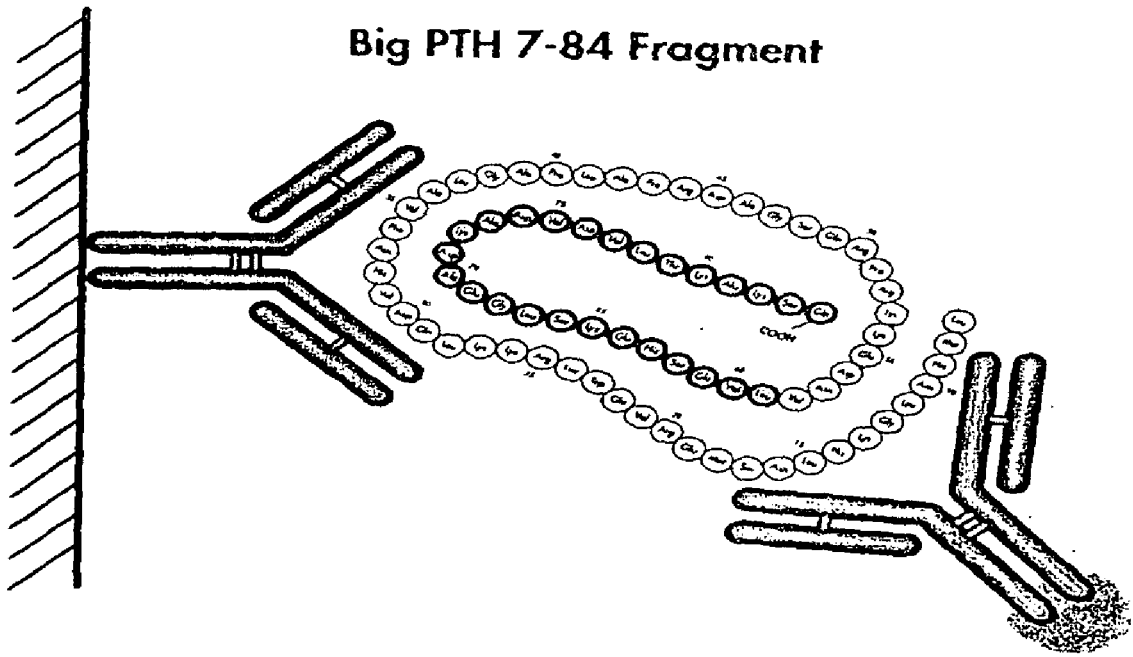

FIG. 5 shows the results for 34 normal human serum samples from healthy subjects which were assayed both by the present wPTH IRMA and the above I-PTH assay. In every case, the level of wPTH detected by the IRMA is lower than that reported by the I-PTH assay, demonstrating the ability of the present IRMA to avoid detecting the interfering large, non (1-84) PTH fragments detected by the I-PTH assay. FIGS. 6A and 6B illustrate how such interference can occur. An N-terminal PTH specific signal antibody which is not specific to the initial PTH peptide sequence, as in the present invention, can detect not only wPTH (as in FIG. 6A), but also can detect large, non (1-84) PTH fragments (as in FIG. 6B).

Figure 7:
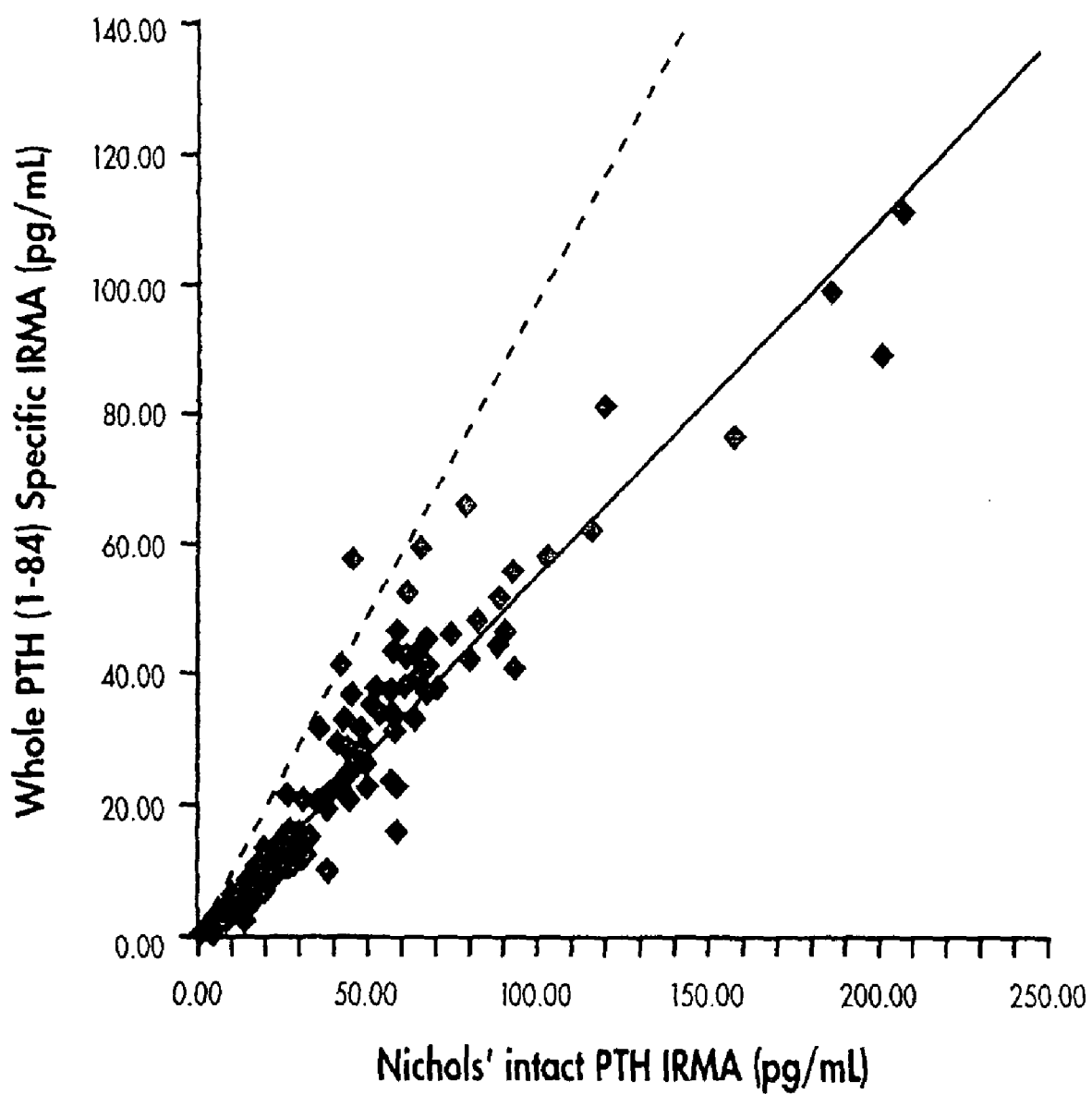
FIG. 7 is a graph comparing a conventional I-PTH assay with the present wPTH assay for patients with chronic uremia.
Figure 8:
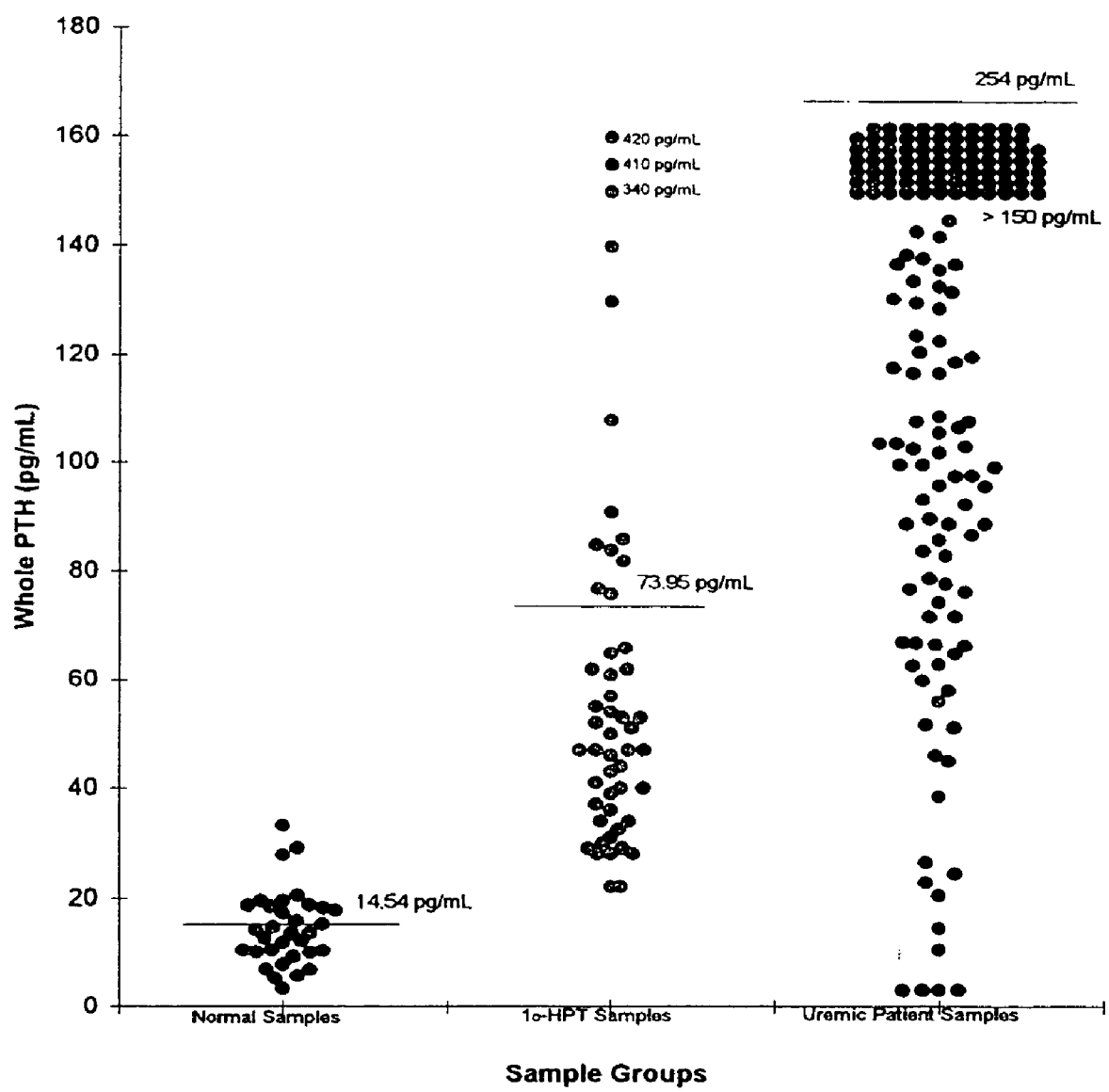
FIG. 8 is a graph showing the distribution of wPTH values for healthy normal persons, patients with primary hyperparathyroidism, and patients with chronic uremia.
Figure 9:
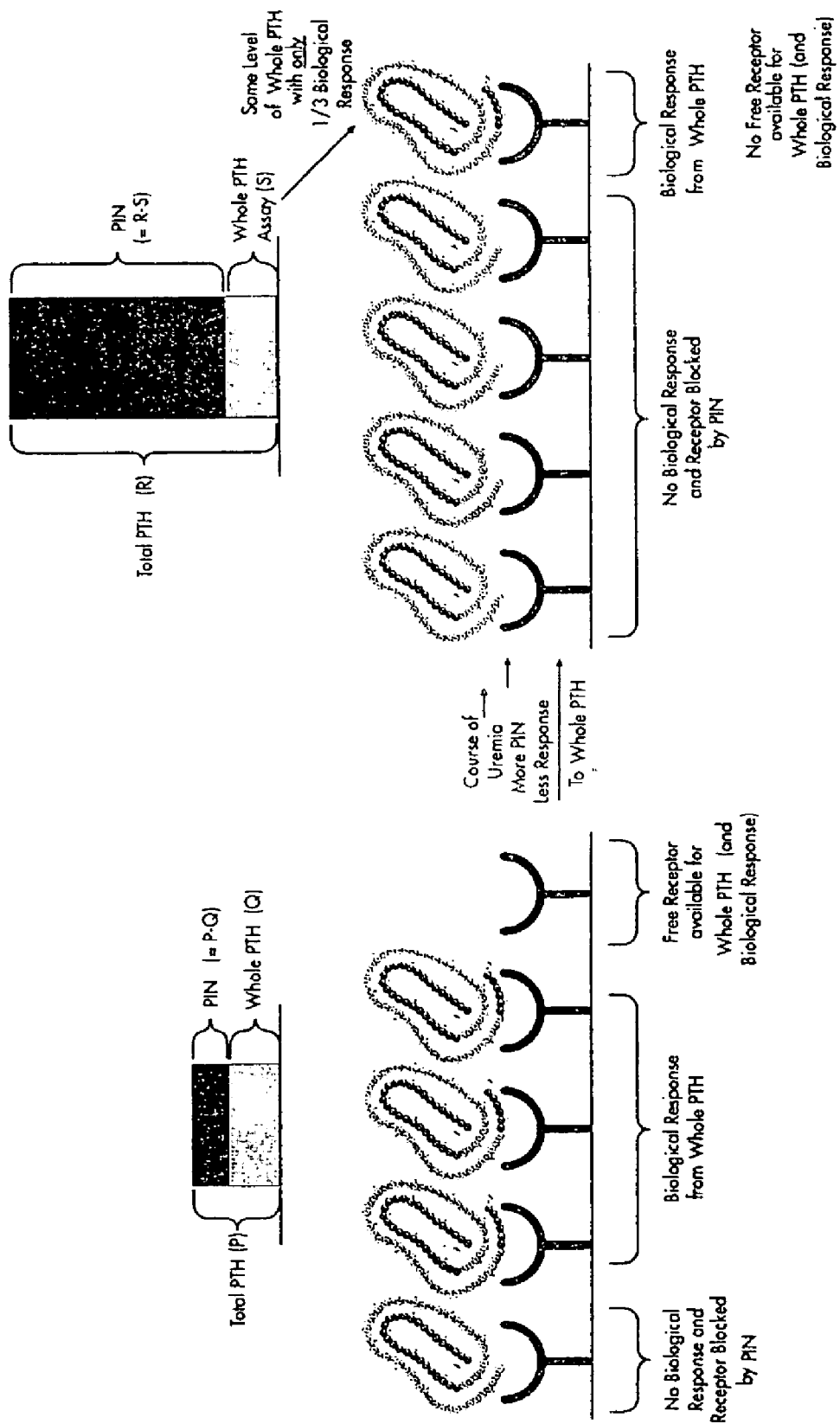
FIG. 9 is a diagrammatic view showing how PIN blocks the action of wPTH at the receptor level, thereby making the person insensitive to the biological effects of wPTH.

A comparison of assay results for 157 chronic uremic patients is shown in FIG. 7. Serum samples from these patients were measured using the wPTH IRMA and the above I-PTH assay. In every case the wPTH levels are lower than I-PTH values.

Clinical Use

The present wPTH and PIN assays have been used in a clinical setting involving 188 persons. The group included 31 persons having normal healthy parathyroid glands and 157 patients with chronic uremia who are undergoing dialysis on a continuous basis. Each person had a blood sample drawn which was assayed using a wPTH assay from Scantibodies Laboratory, Inc. as well as an I-PTH assay from Nichols Institute which gave total PTH values.

Table 1 shows the results individually and comparatively, of the wPTH, PIN, and total PTH assays from chronic uremic patients on dialysis.

TABLE 1

| Patient No. | Total PTH pg/ml | Whole PTH pg/ml | PIN pg/ml | PIN to Total PTH | PIN to Whole PTH | Whole PTH to Total PTH |
|---|---|---|---|---|---|---|
| 1 | 1410 | 740 | 670 | 48% | 91% | 52% |
| 2 | 185 | 89 | 96 | 52% | 108% | 48% |
| 3 | 231 | 104 | 127 | 55% | 122% | 45% |
| 4 | 1020 | 590 | 430 | 42% | 73% | 53% |
| 5 | 270 | 159 | 111 | 41% | 70% | 59% |
| 6 | 201 | 100 | 101 | 50% | 101% | 50% |
| 7 | 380 | 100 | 280 | 74% | 280% | 26% |
| 8 | 460 | 277 | 183 | 40% | 66% | 60% |
| 9 | 380 | 197 | 183 | 48% | 93% | 52% |
| 10 | 880 | 522 | 358 | 41% | 69% | 59% |
| 11 | 310 | 154 | 156 | 50% | 101% | 50% |
| 12 | 880 | 451 | 429 | 49% | 95% | 51% |
| 13 | 670 | 418 | 252 | 38% | 60% | 63% |
| 14 | 390 | 221 | 169 | 43% | 76% | 57% |
| 15 | 170 | 108 | 62 | 36% | 57% | 64% |
| 16 | 510 | 381 | 129 | 25% | 34% | 75% |
| 17 | 200 | 67 | 133 | 67% | 199% | 34% |
| 18 | 170 | 109 | 61 | 36% | 56% | 64% |
| 19 | 360 | 199 | 161 | 45% | 81% | 55% |
| 20 | 260 | 164 | 96 | 37% | 59% | 63% |
| 21 | 440 | 372 | 68 | 15% | 18% | 85% |
| 22 | 120 | 51.7 | 68.3 | 57% | 132% | 43% |
| 23 | 600 | 527 | 73 | 12% | 14% | 83% |
| 24 | 220 | 130 | 90 | 41% | 69% | 59% |
| 25 | 190 | 136 | 54 | 28% | 40% | 72% |
| 26 | 220 | 118 | 102 | 46% | 86% | 54% |
| 27 | 630 | 334 | 296 | 47% | 89% | 53% |
| 28 | 150 | 90 | 60 | 40% | 67% | 60% |
| 29 | 170 | 106 | 64 | 38% | 60% | 62% |
| 30 | 810 | 489 | 321 | 40% | 66% | 60% |
| 31 | 570 | 319 | 251 | 44% | 79% | 56% |
| 32 | 570 | 467 | 103 | 18% | 22% | 82% |
| 33 | 400 | 300 | 100 | 25% | 33% | 75% |
| 34 | 560 | 378 | 182 | 33% | 48% | 68% |
| 35 | 310 | 121 | 189 | 61% | 156% | 39% |
| 36 | 240 | 98 | 142 | 59% | 145% | 41% |
| 37 | 280 | 133 | 157 | 54% | 118% | 48% |
| 38 | 230 | 124 | 106 | 46% | 85% | 54% |
| 39 | 350 | 319 | 31 | 9% | 10% | 91% |
| 40 | 200 | 133 | 67 | 34% | 50% | 67% |
| 41 | 920 | 564 | 356 | 39% | 63% | 61% |
| 42 | 210 | 89 | 121 | 58% | 136% | 42% |
| 43 | 1990 | 904 | 1086 | 55% | 120% | 45% |
| 44 | 300 | 212 | 88 | 29% | 42% | 71% |
| 45 | 260 | 132 | 128 | 49% | 97% | 51% |
| 46 | 140 | 72 | 68 | 49% | 94% | 51% |
| 47 | 250 | 129 | 121 | 48% | 94% | 52% |
| 48 | 130 | 72 | 58 | 45% | 81% | 56% |
| 49 | 1840 | 1000 | 840 | 46% | 84% | 54% |
| 50 | 280 | 167 | 113 | 40% | 68% | 60% |
| 51 | 490 | 268 | 222 | 45% | 83% | 55% |
| 52 | 150 | 77.1 | 72.9 | 49% | 95% | 51% |
| 53 | 140 | 58.1 | 81.9 | 59% | 141% | 42% |
| 54 | 210 | 92.7 | 117.3 | 56% | 127% | 44% |
| 55 | 160 | 79 | 81 | 51% | 103% | 49% |
| 56 | 480 | 296 | 184 | 38% | 62% | 62% |
| 57 | 480 | 281 | 199 | 41% | 71% | 59% |
| 58 | 270 | 120 | 150 | 56% | 125% | 44% |
| 59 | 97 | 45 | 52 | 54% | 116% | 46% |
| 60 | 330 | 154 | 176 | 53% | 114% | 47% |
| 61 | 110 | 56 | 54 | 49% | 96% | 51% |
| 62 | 660 | 456 | 204 | 31% | 45% | 69% |
| 63 | 300 | 137 | 163 | 54% | 119% | 46% |
| 64 | 240 | 145 | 95 | 40% | 66% | 60% |

TABLE 1-continued

| Patient No. | Total PTH pg/ml | Whole PTH pg/ml | PIN pg/ml | PIN to Total PTH | PIN to Whole PTH | Whole PTH to Total PTH |
|---|---|---|---|---|---|---|
| 65 | 100 | 66.5 | 33.5 | 34% | 50% | 67% |
| 66 | 410 | 416.3 | −6.3 | −2% | −2% | 102% |
| 67 | 410 | 235.7 | 174.3 | 43% | 74% | 57% |
| 68 | 45 | 14.4 | 30.6 | 68% | 213% | 32% |
| 69 | 200 | 102.3 | 97.7 | 49% | 96% | 51% |
| 70 | 300 | 134 | 166 | 55% | 124% | 45% |
| 71 | 320 | 202 | 118 | 37% | 58% | 63% |
| 72 | 440 | 254 | 186 | 42% | 73% | 58% |
| 73 | 190 | 99.6 | 90.4 | 48% | 91% | 52% |
| 74 | 160 | 74.6 | 85.4 | 53% | 114% | 47% |
| 75 | 600 | 429.8 | 170.2 | 28% | 40% | 72% |
| 76 | 1140 | 632 | 508 | 45% | 80% | 55% |
| 77 | 440 | 211 | 229 | 52% | 109% | 48% |
| 78 | 450 | 276 | 174 | 39% | 63% | 61% |
| 79 | 510 | 344 | 166 | 33% | 48% | 67% |
| 80 | 190 | 62.8 | 127.2 | 67% | 203% | 33% |
| 81 | 170 | 86 | 84 | 49% | 98% | 51% |
| 82 | 180 | 103.4 | 76.6 | 43% | 74% | 57% |
| 83 | 78 | 22.7 | 55.3 | 71% | 244% | 29% |
| 84 | 230 | 117 | 113 | 49% | 97% | 51% |
| 85 | 160 | 96 | 64 | 40% | 67% | 60% |
| 86 | 220 | 89 | 131 | 60% | 147% | 40% |
| 87 | 470 | 321.5 | 148.5 | 32% | 46% | 68% |
| 88 | 310 | 137 | 173 | 56% | 126% | 44% |
| 89 | 2050 | 1127 | 923 | 45% | 82% | 55% |
| 90 | 930 | 414 | 516 | 55% | 125% | 45% |
| 91 | 180 | 65 | 115 | 64% | 177% | 36% |
| 92 | 560 | 238 | 322 | 58% | 135% | 43% |
| 93 | 640 | 597 | 43 | 7% | 7% | 93% |
| 94 | 590 | 382 | 208 | 35% | 54% | 65% |
| 95 | 270 | 103 | 167 | 62% | 162% | 38% |
| 96 | 560 | 349 | 211 | 38% | 60% | 62% |
| 97 | 180 | 78 | 102 | 57% | 131% | 43% |
| 98 | 790 | 429 | 361 | 46% | 84% | 54% |
| 99 | 670 | 372 | 298 | 44% | 80% | 56% |
| 100 | 140 | 20.4 | 119.6 | 85% | 586% | 15% |
| 101 | 190 | 117 | 73 | 38% | 62% | 62% |
| 102 | 190 | 108 | 82 | 43% | 76% | 57% |
| 103 | 430 | 217 | 213 | 50% | 98% | 50% |
| 104 | 560 | 439 | 121 | 22% | 28% | 78% |
| 105 | 500 | 357.7 | 142.3 | 28% | 40% | 72% |
| 106 | 1560 | 777 | 783 | 50% | 101% | 50% |
| 107 | 62 | 24.3 | 37.7 | 61% | 155% | 39% |
| 108 | 430 | 226 | 204 | 47% | 90% | 53% |
| 109 | 160 | 67.2 | 92.8 | 58% | 138% | 42% |
| 110 | 530 | 346 | 184 | 35% | 53% | 65% |
| 111 | 260 | 142 | 118 | 45% | 83% | 55% |
| 112 | 580 | 163 | 417 | 72% | 256% | 28% |
| 113 | 440 | 579 | −139 | −32% | −24% | 132% |
| 114 | 500 | 232.3 | 267.7 | 54% | 115% | 46% |
| 115 | 160 | 60 | 100 | 63% | 167% | 38% |
| 116 | 340 | 202 | 138 | 41% | 68% | 59% |
| 117 | 260 | 138 | 122 | 47% | 88% | 53% |
| 118 | 260 | 119 | 141 | 54% | 118% | 46% |
| 119 | 160 | 84 | 76 | 48% | 90% | 53% |
| 120 | 130 | 46 | 84 | 65% | 183% | 35% |
| 121 | 190 | 104 | 86 | 45% | 83% | 55% |
| 122 | 420 | 334 | 86 | 20% | 26% | 80% |
| 123 | 630 | 440 | 190 | 30% | 43% | 70% |
| 124 | 75 | 26.4 | 48.6 | 65% | 184% | 35% |
| 125 | 260 | 143 | 117 | 45% | 82% | 55% |
| 126 | 640 | 409 | 231 | 36% | 56% | 64% |
| 127 | 130 | 66.7 | 63.3 | 49% | 95% | 51% |
| 128 | 700 | 381 | 319 | 46% | 84% | 54% |
| 129 | 560 | 376 | 184 | 33% | 49% | 67% |
| 130 | 240 | 107 | 133 | 55% | 124% | 45% |
| 131 | 110 | 63 | 47 | 43% | 75% | 57% |
| 132 | 420 | 297 | 123 | 29% | 41% | 71% |
| 133 | 580 | 229 | 351 | 61% | 153% | 39% |
| 134 | 310 | 201.2 | 108.8 | 35% | 54% | 65% |
| 135 | 160 | 97.9 | 62.1 | 39% | 63% | 61% |
| 136 | 290 | 138.7 | 151.3 | 52% | 109% | 48% |
| 137 | 200 | 96.2 | 103.8 | 52% | 108% | 48% |
| 138 | 770 | 662.7 | 107.3 | 14% | 16% | 86% |
| 139 | 290 | 130.7 | 159.3 | 55% | 122% | 45% |
| 140 | 260 | 219 | 41 | 16% | 19% | 84% |
| 141 | 350 | 211 | 139 | 40% | 66% | 60% |
| 142 | 730 | 463.5 | 266.5 | 37% | 57% | 63% |
| 143 | 490 | 231 | 259 | 53% | 112% | 47% |
| 144 | 160 | 87 | 73 | 46% | 84% | 54% |
| 145 | 380 | 222 | 158 | 42% | 71% | 58% |
| 146 | 210 | 93.5 | 116.5 | 55% | 125% | 45% |
| 147 | 630 | 383.4 | 246.6 | 39% | 64% | 61% |
| 148 | 150 | 83.2 | 66.8 | 45% | 80% | 55% |
| 149 | 320 | 152.5 | 167.5 | 52% | 110% | 48% |
| 150 | 900 | 467.6 | 432.4 | 48% | 92% | 52% |
| 151 | 1180 | 818.6 | 361.4 | 31% | 44% | 69% |
| 152 | 120 | 38.4 | 81.6 | 68% | 213% | 32% |
| 153 | 5230 | 1388 | 3842 | 73% | 277% | 27% |
| 154 | 34 | 10.5 | 23.5 | 69% | 224% | 31% |
| 155 | 1020 | 590.6 | 429.4 | 42% | 73% | 58% |
| 156 | 180 | 76.6 | 103.4 | 57% | 135% | 43% |
| 157 | 120 | 51.1 | 68.9 | 57% | 135% | 43% |
| Median | 300 | 154 | 127 | 46% | 84% | 54% |

TABLE 2 shows the results, individually and comparatively, of the wPTH, PIN, and total PTH assays from the normals.

TABLE 2

| Patient No. | Total PTH pg/ml | Whole PTH pg/ml | PIN pg/ml | PIN to Total PTH | PIN to Whole PTH | Whole PTH to Total PTH |
|---|---|---|---|---|---|---|
| 1 | 17.13 | 3.32 | 13.81 | 81% | 416% | 19% |
| 2 | 32.92 | 10.49 | 22.43 | 68% | 214% | 32% |
| 3 | 31.32 | 10.31 | 21.01 | 67% | 204% | 33% |
| 4 | 41.84 | 12.72 | 29.12 | 70% | 229% | 30% |
| 5 | 33.03 | 10.09 | 22.94 | 69% | 227% | 31% |
| 6 | 44.32 | 14.23 | 30.09 | 68% | 211% | 32% |
| 7 | 31.47 | 6.8 | 24.67 | 78% | 363% | 22% |
| 8 | 20.82 | 10.03 | 10.79 | 52% | 108% | 48% |
| 9 | 34.64 | 15.95 | 18.69 | 54% | 117% | 46% |
| 10 | 23.69 | 5.25 | 18.44 | 78% | 351% | 22% |
| 11 | 53.98 | 17.82 | 36.16 | 67% | 203% | 33% |
| 12 | 52.71 | 18.83 | 33.88 | 64% | 180% | 36% |
| 13 | 26.92 | 5.63 | 21.29 | 79% | 378% | 21% |
| 14 | 39.93 | 11.86 | 28.07 | 70% | 237% | 30% |
| 15 | 48.84 | 20.47 | 28.37 | 58% | 139% | 42% |
| 16 | 29.56 | 13.68 | 15.88 | 54% | 116% | 46% |
| 17 | 36.19 | 14.69 | 21.5 | 59% | 146% | 41% |
| 18 | 20.96 | 6.99 | 13.97 | 67% | 200% | 33% |
| 19 | 59.29 | 27.89 | 31.4 | 53% | 113% | 47% |
| 20 | 45.57 | 18.23 | 27.34 | 60% | 150% | 40% |
| 21 | 35.64 | 18.72 | 16.92 | 47% | 90% | 53% |
| 22 | 38.53 | 19.56 | 18.97 | 49% | 97% | 51% |
| 23 | 21.71 | 9.34 | 12.37 | 57% | 132% | 43% |
| 24 | 32.42 | 13.51 | 18.91 | 58% | 140% | 42% |
| 25 | 28.5 | 10.41 | 18.09 | 63% | 174% | 37% |
| 26 | 18.17 | 7.8 | 10.37 | 57% | 133% | 43% |
| 27 | 39.96 | 17.29 | 22.67 | 57% | 131% | 43% |
| 28 | 34.08 | 15.24 | 18.84 | 55% | 124% | 45% |
| 29 | 42.95 | 19.59 | 23.36 | 54% | 119% | 46% |
| 30 | 38.4 | 12.16 | 26.24 | 68% | 216% | 32% |
| 31 | 47.57 | 18.45 | 29.12 | 61% | 158% | 39% |
| Median | 34.64 | 13.51 | 21.5 | 61% | 158% | 39% |

Clearly, the statistically significant differences in the medians of these two groups demonstrates that one can differentiate between the two by using these assays alone or by comparing their respective values.

TABLE 3

| Sample Type | Total PTH (pg/mL) | Whole PTH (pg/mL) | PIN (pg/mL) | PIN to Total PTH | PIN to Whole PTH | Whole PTH to Total PTH |
|---|---|---|---|---|---|---|
| Chronic Uremia (n = 157) Medians | 300 | 154 | 127 | 46% | 84% | 55% |
| Normal (n = 31) Medians | 34.64 | 13.51 | 21.5 | 61% | 158% | 37% |
| P-Value | <0.0001 | <0.0001 | <0.0001 | <0.0001 | <0.0001 | <0.0001 |

The ordinarily skilled artisan can appreciate that the present invention can incorporate any number of the preferred features described above.

All publications or unpublished patent applications mentioned herein are hereby incorporated by reference thereto.

Other embodiments of the present invention are not presented here which are obvious to those of ordinary skill in the art, now or during the term of any patent issuing from this patent specification, and thus, are within the spirit and scope of the present invention.

We claim:

1. A method for producing an antibody for specifically detecting whole $PTH_{1-84}$ while avoiding detecting an interfering non-(1-84) parathyroid hormone fragment in a biological sample, which method comprises:
   a) administering a first peptide or protein immunogen to a host animal to induce antibody production against said first peptide or protein immunogen in said host animal, said first peptide or protein immunogen being human, rat, bovine, or porcine $PTH_{1-84}$;
   b) monitoring antibody titer produced by said administration of said first peptide or protein immunogen to said host animal;
   c) extracting antiserum produced in said host animal by said administration of said first peptide or protein immunogen; and
   d) purifying said antiserum and selecting an antibody from said antiserum extracted in step c) by affinity chromatography utilizing a second peptide or protein immunogen, which is human $PTH_{1-8}$, rat $PTH_{1-8}$, or a peptide having at least four amino acids in the common sequence of human and rat $PTH_{1-8}$.

2. The method of claim 1, wherein in step a), the host animal is a goat.

3. The method of claim 1, wherein the interfering non-(1-84) parathyroid hormone fragment is $PTH_{7-84}$.

4. The method of claim 1, wherein the first peptide or protein immunogen is human $PTH_{1-84}$.

5. The method of claim 1, wherein the first peptide or protein immunogen is rat $PTH_{1-84}$.

6. The method of claim 1, wherein the first peptide or protein immunogen is bovine $PTH_{1-84}$.

7. The method of claim 1, wherein the first peptide or protein immunogen is porcine $PTH_{1-84}$.

8. The method of claim 1, wherein the first peptide or protein immunogen is human $PTH_{1-84}$, the second peptide or protein immunogen is human $PTH_{1-8}$, and the interfering non-(1-84) parathyroid hormone fragment is $PTH_{7-84}$.

9. The method of claim 1, wherein the first peptide or protein immunogen is rat $PTH_{1-84}$, the second peptide or protein immunogen is rat $PTH_{1-8}$, and the interfering non-(1-84) parathyroid hormone fragment is $PTH_{7-84}$.

10. The method of claim 1, wherein the interfering non-(1-84) parathyroid hormone fragment is a peptide having an amino acid sequence from between $PTH_{3-84}$ and $PTH_{34-84}$ and functions in vivo as a wPTH antagonist or inhibitor.

11. The antibody produced by the method of claim 1.

12. The antibody of claim 11, wherein the antibody is a polyclonal antibody.

13. The antibody of claim 11, wherein the antibody is a monoclonal antibody.

14. The antibody of claim 11, wherein the antibody further comprises a label.

15. The antibody of claim 14, wherein the label is selected from the group consisting of a chemiluminescent agent, a colorimetric agent, an energy transfer agent, an enzyme, a fluorescent agent and a radioisotope.

16. The antibody of claim 11, wherein the antibody is bound to a solid support.

17. The antibody of claim 16, wherein the solid support is a colloidal solid support or a latex particle.

18. A method for producing an antibody for specifically detecting whole $PTH_{1-84}$ while avoiding detecting an interfering non-(1-84) parathyroid hormone fragment in a biological sample, which method comprises:
   a) administering human, rat, bovine, or porcine $PTH_{1-84}$ to a host animal to induce antibody production against said human, rat, bovine, or porcine $PTH_{1-84}$;
   b) recovering antiserum produced in said host animal by said administration of said human, rat, bovine, or porcine $PTH_{1-84}$; and
   c) purifying an antibody that specifically binds to whole $PTH_{1-84}$ while avoiding detecting an interfering non-(1-84) parathyroid hormone fragment in a biological sample from said antiserum using human $PTH_{1-8}$, rat $PTH_{1-8}$, or a peptide having at least four amino acids in the common sequence of human and rat $PTH_{1-8}$.

19. The antibody produced by the method of claim 18.

* * * * *

```
                        SEQUENCE LISTING

<160> NUMBER OF SEQ ID NOS: 7

<210> SEQ ID NO 1
<211> LENGTH: 84
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asn Lys Ala Asp Val Asn Val Leu Thr Lys
65                  70                  75                  80

Ala Lys Ser Gln

<210> SEQ ID NO 2
<211> LENGTH: 82
<212> TYPE: PRT
<213> ORGANISM: Homo sapiens

<400> SEQUENCE: 2

Ser Glu Ile Gln Leu Met His Asn Leu Gly Lys His Leu Asn Ser Met
1               5                   10                  15

Glu Arg Val Glu Trp Leu Arg Lys Lys Leu Gln Asp Val His Asn Phe
            20                  25                  30

Val Ala Leu Gly Ala Pro Leu Ala Pro Arg Asp Ala Gly Ser Gln Arg
        35                  40                  45

Pro Arg Lys Lys Glu Asp Asn Val Leu Val Glu Ser His Glu Lys Ser
    50                  55                  60

Leu Gly Glu Ala Asn Lys Ala Asp Val Asn Val Leu Thr Lys Ala Lys
65                  70                  75                  80

Ser Gln
```

```
<210> SEQ ID NO 3
<211> LENGTH: 51
<212> TYPE: PRT
<213> ORGANISM: Homo sapiens

<400> SEQUENCE: 3

Phe Val Ala Leu Gly Ala Pro Leu Ala Pro Arg Asp Ala Gly Ser Gln
 1               5                  10                  15

Arg Pro Arg Lys Lys Glu Asp Asn Val Leu Val Glu Ser His Glu Lys
             20                  25                  30

Ser Leu Gly Glu Ala Asn Lys Ala Asp Val Asn Val Leu Thr Lys Ala
         35                  40                  45

Lys Ser Gln
     50

<210> SEQ ID NO 4
<211> LENGTH: 8
<212> TYPE: PRT
<213> ORGANISM: Homo saiens

<400> SEQUENCE: 4

Ser Val Ser Glu Ile Gln Leu Met
 1               5

<210> SEQ ID NO 5
<211> LENGTH: 32
<212> TYPE: PRT
<213> ORGANISM: Homo sapiens

<400> SEQUENCE: 5

Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
             20                  25                  30

<210> SEQ ID NO 6
<211> LENGTH: 78
<212> TYPE: PRT
<213> ORGANISM: Homo sapiens

<400> SEQUENCE: 6

Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
             20                  25                  30

Ala Pro Leu Ala Pro Arg Asp Ala Gly Ser Gln Arg Pro Arg Lys Lys
         35                  40                  45

Glu Asp Asn Val Leu Val Glu Ser His Glu Lys Ser Leu Gly Glu Ala
     50                  55                  60

Asn Lys Ala Asp Val Asn Val Leu Thr Lys Ala Lys Ser Gln
 65                  70                  75

<210> SEQ ID NO 7
<211> LENGTH: 8
<212> TYPE: PRT
<213> ORGANISM: Rat

<400> SEQUENCE: 7

Ala Val Ser Glu Ile Gln Leu Met
 1               5
```